United States Patent [19]
Yother et al.

[11] Patent Number: 5,948,900
[45] Date of Patent: Sep. 7, 1999

[54] STREPTOCOCCUS PNEUMONIAE CAPSULAR POLYSACCHARIDE GENES AND FLANKING REGIONS

[75] Inventors: Janet Yother, Birmingham, Ala.; Joseph Dillard, Hinsdale, Ill.

[73] Assignee: UAB Research Foundation, Birmingham, Ala.

[21] Appl. No.: 08/867,030

[22] Filed: Jun. 2, 1997

Related U.S. Application Data

[63] Continuation-in-part of application No. 08/243,546, May 16, 1994, abandoned.

[51] Int. Cl.[6] ............................ C07H 21/04; C07H 21/02
[52] U.S. Cl. ...................... 536/24.32; 536/23.1; 536/23.7
[58] Field of Search .................................. 536/23.1, 23.7, 536/24.32; 436/94; 435/91.1, 882, 6

[56] References Cited

PUBLICATIONS

Sigma Molecular Biology a New Dimension 1989 p. 54.

*Primary Examiner*—Bradley L. Sisson
*Attorney, Agent, or Firm*—Benjamin Aaron Adler

[57] ABSTRACT

Disclosed is the identification, cloning and sequencing of flanking DNA regions common to all polysaccharide capsule types in *Streptococcus pneumoniae*. Also disclosed are particular type-specific genes and gene products that direct the formation of the *Streptococcus pneumoniae* serotype-specific polysaccharide capsule. Methods are provided for detecting *Streptococcus pneumoniae*. and for constructin gene cassettes that may be transferred as a unit during transformation and used to direct the expression of specific serotyes of *Streptococcus pneumoniae* capsules.

8 Claims, 39 Drawing Sheets

```
SacI    Cps3B
GAGCT CGG TAT TTT TTG GAA CGT GAT TTA GTT CAT GTA GTT GCA AGT GAC ATG CAC
      ala arg tyr phe leu glu arg asp leu val his val val ala ser asp met his AaT TTA GAC AGT AGA CCT CCA TAT ATg CAA CAG GCA TAT gAT ATc ATT GCT AAG
asn leu asp ser arg pro pro tyr met gln gln ala tyr asp ile ile ala lys AAA TAT AGA GCG AAA AAA GCG AAA GAA CTT TTT GTA GAT AAT CCC AGA AAA ATT
lys tyr arg ala lys lys ala lys glu leu phe val asp asn pro arg lys ile stop Cps3B           start Cps3C
ATA ATG GAT CAT TAA TTA GGA GAA AAT ATG AAG GAA CAA AAC ACT TTG GAA aTC
ile met asp his ***  leu gly glu asn met lys glu gln asn thr leu glu ile GAT GTA TTG CAG TAT Tca gaG CTT aTT GGa aGa aGT GtC aTT TTa TTa GTG GCa
asp val leu gln tyr ser glu leu ile gly arg ser val ile leu leu val ala TTa TaC TTC TTC aGT TGC TTT TTc CTa C
leu tyr phe phe ser cys phe phe leu ~200 nt gap in cps3C
```

FIG. 6A cps3C (continued to PstI site. ~45 nt expected beyond PstI to Cps3C stop)

ctt ccg tat gcc gcG TTC CTg caa gac ccc aTC GGC Tgg CTC TTT Gat aga GTa
leu pro tyr ala ala phe leu gln asp pro ile gly trp leu phe asp arg val GCT gcc caa aaa aTT aTC AGT ATT ACT CGT GCT GAT GTg gca CAC TGG AGG Agc
ala ala gln lys ile ile ser ile thr arg ala asp val ala his trp arg ser aag acc gcc GAT ATC ACC gCT TcG CCA AAT aaT AAA cGC AAT ACA CTA ATT GGT
lys thr ala asp ile thr ala ser pro asn asn lys arg asn thr leu ile gly TTT TTG Gca TTT TTT ATT GGA ACT AGT GTc ATA GTT CTT CTT CTT GAA CTT TTG
phe leu ala phe phe ile gly thr ser val ile val leu leu leu glu leu leu PstI
GAC ACT CAT GTG AAA cGT CCG GAA GAT ATC GAA GAT ACA CTG CAG
asp thr his val lys arg pro glu asp ile glu asp thr leu gln ~360 nt gap

FIG. 6B

```
                                            PvuII
Cps3E
CAG CAC ttc tCA TCT GGC ACA GCT GAt ttA TCT CAC GGc ttA TGT GAt ACA AAT
gln his phe ser ser gly thr ala asp leu ser his gly leu cys asp thr asn ATT gAA AAT TTA TTT GTA GTT CAA TCG GGA TCT GTA TCA CCA AAC CCT ACA GCC
ile glu asn leu phe val val gln ser gly ser val ser pro asn pro thr ala End homology
      with Cps19fD Repeat
TTG Tca cAA AGc AAA AAT TTT GTG GTT ATG GTA AAG CTT TTT TCA AAA GAG GTC
leu ser gln ser lys asn phe AGT ATA TTG AGT TGG TGG AAA CGA TAA AAT ACA TAA TAT TTT ATT CCT TTG GTT
                                                              SacI
ATC AAA TTA GCC CCT CCT GAA GCT CCC CAA TTG ACG GCT TGA GCT C
```

FIG. 6C

SacI
GAGCTCCAATCAAAGGGTGTGTTTGTACACTTTTTGACAGAGGGTAATCGCTAGAGGACAGC  60

AAACGGCCATAGTAGTGAAAAATCCAGCACCTAAAGCAGACAAAAGGGTTGCCATCAGGT  120

ATAAAAATCATGTAGAGGGCGTTAGGGTAGGTGCGTGTGCGGTAGAGAATGTGTTGAGCCA  180

AAACATCAAGAGTACCGTTAGTTATTGCAAAGTTATAAAGAGAGGAGACGCTAAAAATGG  240

TAAAAAAGAGTGAGGTTGGCCAAAATGAAGAAGTTCTTTGGGGCTTAATCCCATGAGAGT  300

GGTTGCGATGAGGTAAGAAAAAGCAATAGCCAGCAGGTCAATATTGATTTTGGTGCGGTA  360

ACCAATTCCAATGGCCTAGAGCAATGGCGCTAATCATTATTAAATGAATCATTGAATTGTC  420

CTTTAGTTAGAATATAGAAAGAGGATAGATTGAAGTTCGAGAATACTGGGTGTCTTCTGA  480

TGTTAAGTGGTTGTGTCAAAACCATCCCAAATGGCATAAATTGCGTGGAATTGGAATGAC  540

TCGTAATACTATTGATAGAGATGGTATTACAAGTCAAGACGTTCGCTATTTTATCTTTAA  600

FIG. 6Di

```
                                                                            HindIII
CTTTAAGCTTAGTGTGTAGTAGCCTTTTGCCATAGTGTTCGAGGTCATTGGTCAGCAGAAAG    660

TATGCATTGGTTATTGGATGTGGTTTATCGTGAAGACCATCATCAGACCCTGGATAAACG     720

AGCTGCTTTAACCTTAATCTTATCGAAAAATGTGTTTATATTTTCTAAAAGTGATGGTA      780

TTTTCTAAAAAGACCTCAGCTATCGATGCAAACAACGGTATATCTCTGTACATTTGGAA      840

EcoRV
GATTATTTGGAAAACAGAGGTTAGGAAAGTAATCAGTTAACGGGATATCTTTTCAAAGCTG    900

-35                        -10
ATACTAAGGCACAAAAAAAAGTTTGATATTCCCCTTGACAATAGATAAAATTATTATATA     960
```

FIG. 6Dii

```
AITAAACTATTGCTTTTTAAATAAAGTGAGAATATTAATAATGCAGAGAAAGAGGACTGT        1020
                                           start cps3D
AGTAAAAATGAAAATTGCCATTGCAGGAAGTGGTTATGTAGGTCTGTCTTTAGCGGTGCTA       1080
         M   K   I   A   I   A   G   S   G   Y   V   G   L   S   L   A   V   L
CTAGCTCAGCATCATGAAGTTAAGGTCATTGATGTTATAAAGGATAAGGTAGAGTCGATA        1140
 L   A   Q   H   H   E   V   K   V   I   D   V   I   K   D   K   V   E   S   I
AACAATAGAAAAATCTCCAATTAAGGATGAGGCGATTGAGAAATACTTAGTTGAAAAAGAG       1200
 N   N   R   K   S   P   I   K   D   E   A   I   E   K   Y   L   V   E   K   E
TTGAATCTTGAAGCCTCCTTAGATCCTGCACACGTTTATAAAGACGTGGAGTATGCTATT        1260
 L   N   L   E   A   S   L   D   P   A   H   V   Y   K   D   V   E   Y   A   I
                                                JD619               TAA
ATTGCTACTCCGACTAATTATGATGTAGACTTAAATCAGTTTGATACATCTTCAGTTGAA        1320
 I   A   T   P   T   N   Y   D   V   D   L   N   Q   F   D   T   S   S   V   E
                                                            ScaI
GCTGCTATCAAGACTTGTATGGAATATAATGATACTTGTACAATCGTAATCAAAAGTACT        1380
 A   A   I   K   T   C   M   E   Y   N   D   T   C   T   I   V   I   K   S   T
```

FIG. 6Ei

```
ATTCCTGAAGGGTATACTAAAGAAGTGAGGAGAAAGTTTAATACAGATCGTATTATTTT      1440
 I  P  E  G  Y  T  K  E  V  R  E  K  F  N  T  D  R  I  I  F
            HindIII
TCTCCAGAGTTTCTACGTGAATCCAAAGCTTTATATGATAATTTGTATCCATCTAGAATT     1500
 S  P  E  F  L  R  E  S  K  A  L  Y  D  N  L  Y  P  S  R  I
                            ▲ JD982
GTTGTAGGAACTGATTTGGATGATTCTGAGTTAACAAAAAGAGCATGGCAGTTTGCAGAT     1560
 V  V  G  T  D  L  D  D  S  E  L  T  K  R  A  W  Q  F  A  D
CTACTTAAAGGTGGAGCTATTAAGGAAGAGGTTCCGATACTGGTTGTTGCTTTTAATGAA     1620
 L  L  K  G  G  A  I  K  E  E  V  P  I  L  V  V  A  F  N  E
GCAGAGGTTGCAAAATTGTTTAGTAACACTTACTTGGCAACTCGCGTAGCTTATTTTAAT     1680
 A  E  V  A  K  L  F  S  N  T  Y  L  A  T  R  V  A  Y  F  N
GAGATAGATACATATAGCGAGGTAAAAGGGCTTAATCCCAAGACAATTATTGATATTGTT     1740
 E  I  D  T  Y  S  E  V  K  G  L  N  P  K  T  I  I  D  I  V
```

FIG. 6Eii

```
TGTTATGATCCTAGAATTGGATCAGACTATAATAACCCTAGCTTTGGTTACGGAGGGTAT    1800
 C  Y  D  P  R  I  G  S  D  Y  N  N  P  S  F  G  Y  G  G  Y

TGCTTACCAAAAGACACAAAGCAATTGAAAGCAAGTTTTAGGGATGTTCCTGAAAATCTG    1860
 C  L  P  K  D  T  K  Q  L  K  A  S  F  R  D  V  P  E  N  L
        PvuII
ATTACAGCTGTGGTGCAATCTAATAAAACAAGATTATATAGCTGGAGCTATTCTA        1920
 I  T  A  V  V  Q  S  N  K  T  R  K  D  Y  I  A  G  A  I  L
                                           TGA JD611    A66R2 AAA
GCTAAACAACCTAGTGTTGTAGGTATTTATAGATTAATTATGAAAATCTGATTCTGATAAT  1980
 A  K  Q  P  S  V  V  G  I  Y  R  L  I  M  K  S  D  S  D  N
                                                             K
  TGT Rx1
TTTCGTTCTAGTGCTGTTAAGGGAGTTATGGAACGTTTGGACAATTATGGTAAAGAAATT   2040
 F  R  S  S  A  V  K  G  V  M  E  R  L  D  N  Y  G  K  E  I
 C

GTTATTTACGAACCTACTATTGAGTGTGATACTTTTATGGGATACAGAGTAATTAAATCT   2100
 V  I  Y  E  P  T  I  E  C  D  T  F  M  G  Y  R  V  I  K  S
```

FIG. 6Eiii

```
                  SspI                                                      2160
TTAGATGAATTTAAGAATATTTCTGACATTGTTGTAGCGAATCGTATGAACGATGATTTA
 L  D  E  F  K  N  I  S  D  I  V  V  A  N  R  M  N  D  D  L
                   ▲ JD983 end cps3D          2220
AGGGATATACAAGAAAAACTCTATACACGGCGATTTATTGGCAGAGAGAATAAGGGGAAATA
 R  D  I  Q  E  K  L  Y  T  R  D  L  F  G  R  E  *
```

FIG. 6Eiv

```
start cps3S                                                         2280
ATTTTTATGTATACATTATTTAATGTTGTTGGATTTTTTCAGAATCATGATTTTCAT
      M  Y  T  F  I  L  M  L  L  D  F  F  Q  N  H  D  F  H 2340
TTCTTTATGTTGTTTTTGTCTTATTCTTATTCGTTGGGCGGTTATATATTTCATGCT
 F  F  M  L  F  F  V  F  I  L  I  R  W  A  V  I  Y  F  H  A 2400
GTCAGATATAAGTCCTACAGTTGTAGTGTAAGTGATGAGAAGTTATTAGTTCTGTAATT
 V  R  Y  K  S  Y  S  C  S  V  S  D  E  K  L  F  S  S  V  I 2460
ATCCCTGTCGTGGATGAACCACTTAATCTTTTTGAAAGTGTACTGAATAGAATTTCCAGA
 I  P  V  V  D  E  P  L  N  L  F  E  S  V  L  N  R  I  S  R
                                                   ▲ JD908

2520
CATAAAACCATCCGAAATTATTGTGGTTATTAACGGCCCCAAAAAAACGAGAGACTTGTAAAA
 H  K  P  S  E  I  I  V  V  I  N  G  P  K  N  E  R  L  V  K
                                     ▲ JD846

2580
CTTTGTCATGATTTTAATGAAAAATTAGAAAATAATGACTCCAATTCAATGTTATTAC
 L  C  H  D  F  N  E  K  L  E  N  N  M  T  P  I  Q  C  Y  Y
```

FIG. 6Fi

```
ACTCCTGTTCCTGGCAAGAGAAATGCTATCCGCGTTGGGCTGGAGCATGTGGATTCGCAG    2640
 T  P  V  P  G  K  R  N  A  I  R  V  G  L  E  H  V  D  S  Q

AGTGATATTACAGTTCTAGTAGATAGTGATACAGTATGGACGCCTAGAACCTTGAGTGAG    2700
 S  D  I  T  V  L  V  D  S  D  T  V  W  T  P  R  T  L  S  E

TTGCTGAAGCCTTTTGTTTGCGATAAAAAAATAGGTGGGTAACGACAAGACAAAAAATT    2760
 L  L  K  P  F  V  C  D  K  K  I  G  G  V  T  T  R  Q  K  I

CTTGACCCTGAGCGTAATCTCGTGACAATGTTTGCTAACTTGTTAGAGGAAATTAGGGCA    2820
 L  D  P  E  R  N  L  V  T  M  F  A  N  L  E  E  I  R  A

GAAGGAACTATGAAAGCAATGAGTGTGACTGGTAAAGTAGGGTGCTTACCTGGTCGAACA    2880
 E  G  T  M  K  A  M  S  V  T  G  K  V  G  C  L  P  G  R  T

ATTGCTTTTAGAAATATAGTGGAGAGAGTGTATACAAAGTTTATAGAAGAGACTTTCATG    2940
 I  A  F  R  N  I  V  E  R  V  Y  T  K  F  I  E  E  T  F  M
 ▲ JD902

GGATTTCATAAGGAAGTTTCTGATGATAGAAGTCTTACAAATTTGACTTTAAAAAAAGGC    3000
 G  F  H  K  E  V  S  D  D  R  S  L  T  N  L  T  L  K  K  G
```

FIG. 6Fii

```
TATAAAACTGTTATGCAGGATACTTCTGTTGTGTATACAGATGCTCCTACAAGTTGGAAA      3060
 Y  K  T  V  M  Q  D  T  S  V  V  Y  T  D  A  P  T  S  W  K

AAGTTCATTAGACAGCAACTAAGGTGGGCAGAAGGTTCTCAGTATAACAATCTAAAGATG      3120
 K  F  I  R  Q  Q  L  R  W  A  E  G  S  Q  Y  N  N  L  K  M

ACTCCTTGGATGATTAGAAATGCCCCTCTTATGTTTTTTATTTATTTTACAGATATGATT      3180
 T  P  W  M  I  R  N  A  P  L  M  F  F  I  Y  F  T  D  M  I

TTACCTATGCTACTTATTAGCTTTGGTGTGAATATATTCCTGTTGAAAATATTAAATATA      3240
 L  P  M  L  L  I  S  F  G  V  N  I  F  L  L  K  I  L  N  I

ACTACAATTGTTTATACAGCTTCATGGTGGGAAATTATTTTATATGTTCTAGAATGAAGT      3300
 T  T  I  V  Y  T  A  S  W  W  E  I  I  L  Y  V  L  L  G  M

ATTTTAGCTTTTGGAGGAAGAAACTTTAAAGCTATGTCTAGAATGAAGTGGTATTATGTA      3360
 I  F  S  F  G  G  R  N  F  K  A  M  S  R  M  K  W  Y  Y  V
                                         ▲ JD897

TTCTTATTCCTGTTTTTATAATCGTTTTGAGTATAATTATGTGCCCTATTAGGCTATTA       3420
 F  L  I  P  V  F  I  I  V  L  S  I  I  M  C  P  I  R  L  L
```

FIG. 6Fiii

```
GGACTTATGAGATGTTCTGATGATTTAGGGTGGGGAACTAGGAATTTAACAGAGTGAGAT    3480
 G  L  M  R  C  S  D  D  L  G  W  G  T  R  N  L  T  E  *        end cps3S

AAATAGTAGTGCGTATATAGAGTATTTACTCAGAGTATTAATTGATTTTTGAAAAGGAAA    3540

AGTGTTTTTTAATGTTAAGAAAGAACTTGAAATATCAGATTATGACACGAGCTGGAACAA    3600
```

FIG. 6Fiv

```
                                                                                            -35
TTTTAGCTATCTTGTTTTTCATTATATTAGGGATTATTGTTGAAGTTTTGTTTTAAGGCT                               3660
       -10
CATTGTCATCTGTAGTGGCTCACTTCAGACGTAAGGGTCATATTTTAATGTGAAAAGAGT                               3720
                                                           start cps3U
GTTAAAAGATTAATCACTTATATTATTTAATAGAAATAGTGTAAGGAATTGTTATGAAA                                3780
                                                              M  K
AAAGTAAAAAAAAAGCTGTTATTCCTGCTGCAGGGCTGGGCACACGATTTTTGCCTGCCACT                             3840
 K  V  K  K  A  V  I  P  A  A  G  L  G  T  R  F  L  P  A  T
 HindIII
AAAGCTTTGGCAAAAGAAATGCTTCCAATTGTAGACCGCCCCACAATTCATTTGTCATT                                3900
 K  A  L  A  K  E  M  L  P  I  V  D  R  P  T  I  H  F  V  I
              HindIII
GAAGAAGCTTTACGTTCGGGTATTGAAGATATTCTAGTAGTTACTGGAAAGAGTAAACGT                               3960
 E  E  A  L  R  S  G  I  E  D  I  L  V  V  T  G  K  S  K  R
```

FIG. 6Gi

```
TCTATTGAAGATTATTTGATTCAACTTTTGAATTGGAATATAGTCTTAGAAAACAAGGA    4020
 S  I  E  D  Y  F  D  S  T  F  E  L  E  Y  S  L  R  K  Q  G

AAGATGGAACTTCTTAAGTCAGTTAACGAATCGACTGATATTAAAGTACATTTCGTTCGT    4080
 K  M  E  L  L  K  S  V  N  E  S  T  D  I  K  V  H  F  V  R

CAAAGTTCACCAGTGGTCTTGGTGACGCTGTTCTCCAAGGCGAAGTCTTTTGTTGGTGAC    4140
 Q  S  S  P  R  G  L  G  D  A  V  L  Q  A  K  S  F  V  G  D
                                            EcoRV
GATCCCTTTGTTGTAATGCTTGGTGATGACCTTATGGATATCACCGACTCAACTGCTGTA    4200
 D  P  F  V  V  M  L  G  D  D  L  M  D  I  T  D  S  T  A  V
                                  Δ JD900

CCTTTAACAAGACAATTGATGGATGATTACAACGCAACACAGGCTTCAACTATCGCAGTA    4260
 P  L  T  R  Q  L  M  D  D  Y  N  A  T  Q  A  S  T  I  A  V

ATGCCTGTTAGATATGAAGATGTTTCTTCTTATGGTGTGATTTCTCCTAGATTGGAAAGT    4320
 M  P  V  R  Y  E  D  V  S  S  Y  G  V  I  S  P  R  L  E  S
```

FIG. 6Gii

```
AGTAATGGCCTCTATAGTGTTGATGCTTTTGTAGAGAAACCAAAACCAGAAGAAGCGCCT    4380
 S  N  G  L  Y  S  V  D  A  F  V  E  K  P  K  P  E  E  A  P

AGCCATTTAGCTATTATTGGACGTTATCTACTACTCCTGAGATTTTCTATATTAGAA       4440
 S  H  L  A  I  I  G  R  Y  L  L  T  P  E  I  F  S  I  L  E

ACCCAAAAGCCAGGAGCAGGTAATGAAATTCAATTGACAGATGCTATTGATACATTGAAT    4500
 T  Q  K  P  G  A  G  N  E  I  Q  L  T  D  A  I  D  T  L  N

AAGACACAGAGTGTTTTTGCGCGTGAATTTGTGGGCAAACGTTACGATGTTGGTGATAAG    4560
 K  T  Q  S  V  F  A  R  E  F  V  G  K  R  Y  D  V  G  D  K

TTTAATTTTATGAAAACATCAATTGATTATGCTCTTCAACATCCTCAGATTAAAGAGAGT    4620
 F  N  F  M  K  T  S  I  D  Y  A  L  Q  H  P  Q  I  K  E  S

TTAAAAAATTACGTTATTGCACTTGGTAAGCAATTGGAGAAGCTAGATGACTGTTCGTCA    4680
 L  K  N  Y  V  I  A  L  G  K  Q  L  E  K  L  D  D  C  S  S

AGTGGACACCTATGAATTGTATAGAAAAGTTATCAAAAATGGCTAAATGTCCCTGATCTTC   4740
 S  G  H  L  *
       end cps3U
```

FIG. 6Giii

```
                start cps3M
AGTGGACACCTATGATGAATTGTATAGAAAAGTTATCAAAAATGGCTAAATGTCCCTGATCTTC    4740
                  M  N  C  I  E  S  Y  Q  K  W  L  N  V  P  D  L  P CAGCTTATTTAAAAGATGAATTGCTCAGCATGGATGACAAAACAAAAGAAGACGCCTTT         4800
 A  Y  L  K  D  E  L  L  S  M  D  D  K  T  K  E  D  A  F  Y ACACAAACCTTGAATTCGGAACAGCTGGTATGCGTGGTTATATTGGTGCTGGGACAAACC        4860
 T  N  L  E  F  G  T  A  G  M  R  G  Y  I  G  A  G  T  N  R GTATTAATATCTATGTGGTGCGTCaagCACACAGAAGGCCTTGCAAATTAGTTGAATCAA        4920
 I  N  I  Y  V  V  R  Q  A  H  R  R  P  C  K  L  V  E  S  K AAGGCGAAACCGCCAAAAAAGCTGGGGTTGCTATTGCCTATGACTCGGACAtTTTTCAC         4980
 G  E  T  A  K  K  A  G  V  A  I  A  Y  D  S  R  H  F  S  P CAGAATTCGCTTTTGAATCTGCCCAAGTATTAGCGGCCCATGGCATTAAATCTTATGTTT       5040
 E  F  A  F  E  S  A  Q  V  L  A  A  H  G  I  K  S  Y  V  F TTGAAAGCCTACGCCCTACTCCTGAGCTGTCTTTTGCTGTTCGTCATCTCGGAGCATTTG       5100
 E  S  L  R  P  T  P  E  L  S  F  A  V  R  H  L  G  A  F  A
```

FIG. 6Hi

```
CTGGTATTATGGTAACCGCCAGTCATACCCCTGCTCCTTTTAATGGTTATAAAGTTTACG    5160
 G  I  M  V  T  A  S  H  T  P  A  P  F  N  G  Y  K  V  Y  G

GTTCTGATGGTGGGCAAATGCTTCCAGCTGACTATATTCGTGCGATTGATAACCCATTTG    5220
 S  D  G  G  Q  M  L  P  A  D  Y  I  R  A  I  D  N  P  F  A

CTGTAGTCCTTGCTGACTTAGAAGAAGCTAAATCAACTGGTCTTATTGAAGTAATTGGTG    5280
 V  V  L  A  D  L  E  E  A  K  S  T  G  L  I  E  V  I  G  E

AAACTCTCGATGCTGCCTACCTTGAAGAGGGTTAAAAGCGTTAATATCAATCAAGATTTGA    5340
 T  L  D  A  A  Y  L  E  E  V  K  S  V  N  I  N  Q  D  L  I

TTGACCAATACGGTCGCGATATGCAAATTGTCTACACACCTCTTCATGGTACTGGAGAAA    5400
 D  Q  Y  G  R  D  M  Q  I  V  Y  T  P  L  H  G  T  G  E  M

TGCTAGCACGTCGAGCTTTAGCACAAGCTGGTTTCGAATCTGTTCAAGTTGTCGAAGCTC    5460
 L  A  R  R  A  L  A  Q  A  G  F  E  S  V  Q  V  V  E  A  Q

AAGCAAAAACCAGACCCAGACTTCTCAACAGTTGCATCACCAAACCCTGAAAGTCAAGCCG    5520
 A  K  P  D  P  D  F  S  T  V  A  S  P  N  P  E  S  Q  A  A
```

FIG. 6Hii

```
CCTTTGCCTTAGCTGAAGAACTAGGGCGTCAAGTCGATGCTGATGTATTAGTGGCGACTG  5580
 F   A   L   A   E   E   L   G   R   Q   V   D   A   D   V   L   V   A   T   D

ACCCTGATGCTGACCGTCTCGGTGTTGAAATTCGTCAAGCTGATGGCAGTTATTGGAACC  5640
 P   D   A   D   R   L   G   V   E   I   R   Q   A   D   G   S   Y   W   N   L

TTTCTGGTAACCAAATCGGTGCTCTTATCGCCAAATACATTTTAGAAGCTCACAAACAAG  5700
 S   G   N   Q   I   G   A   L   I   A   K   Y   I   L   E   A   H   K   Q   A

CTGGGACACTCCCAAAGAATGCTGCATTGGCAAAATCAATAGTATCAACTGAATTAGTCA  5760
 G   T   L   P   K   N   A   A   L   A   K   S   I   V   S   T   E   L   V   T

CCAAAATTGCGGAAAGCTATGGCGAACCATGTTTAACGTCATTACAGGTTTCAAATTCAT  5820
 K   I   A   E   S   Y   G   E   P   C   L   T   S   L   Q   V   S   N   S   S

CGCTGAGAAAATTCAAGAATTTGAAGAAAAACATAACCTACATGTTTGGGTTTGAAGAAA  5880
 L   R   K   F   K   N   L   K   K   N   I   T   Y   M   F   G   F   E   E   S end cps3M
GCTGATGAGTTTATTGATTGCCTCCAGCTTGGAGTTAGAATAGGGCATCTGGATGGCATT  5940
 *
```

FIG. 6Hiii

```
TGTCACGTATTTCTGTAGGCGCACCAGGCGTGCTAAGAGCAGTTCTAAAGGCTTGATTGAG      6000
TTGGGGAAAGCCTCAGTTAACAAGTCAAAGAAATGGTCGGCATTCTTTCTTGCAGGTG        6060
GAAAAGCAGGAGCTGGTAAAGATCGTCATAATAGTGGGAGCTCATCTGAGAAAGCTAAGGT     6120
TTTATTGACGATTTCTCGAGGTGTCAGTGTCTGTGTCTAAAAGTTCTTGAGTAGAGAAGGCCTT  6180
ATCAGACAGTTTTCGGCTATCCTTTTGGAAAATTCGCCAGTGATTTTTCATGGGCGATA       6240
GGAAAGTGATTGCTTGTCAAAATTCTTCATGATGACAATTCTGGTTGTCATCATCTCACG     6300
GCTTAGGGTGCTGgATGATATGAAATCTATCAAGGACGATTTGTGCATTGGAAATAGGC      6360
        start 'plpA
ATTTAATCACAGACTCTATTACGTATCTAGTTGGTCAAATATTCGACCGTCAGTCCTAT      6430
         Q D S I T Y L V G Q I F D R Q S Y
AAATATACATCTAAGACCAGAGAAGAACAAAAAACATCTACGAAAAAGGCTCTCTTAAAC    6480
 K Y T S K T R E E Q K T S T K K A L L N
```

FIG. 6Ii

```
AAGGATTCCGTCAagCTATTGCATTTGGATTTGACCGtATGCCTCTCAGTTGAATGGA    6540
 K  D  F  R  Q  A  I  A  F  G  F  D  R  Y  A  S  Q  L  N  G

CAAACTGGAGCAAGCAAAATCTTACGTAATCTCTTTGTCCCACCAACATTGTTCAAGCA    6600
 Q  T  G  A  S  K  I  L  R  N  L  F  V  P  P  T  F  V  Q  A

GATGGCAAAAACTTTGGCGATATGGCCAAAGAGAAATTGGTCACTTATGGGGATGAATGG    6660
 D  G  K  N  F  G  D  M  A  K  E  K  L  V  T  Y  G  D  E  W

AAGGATGTTAATCTTGCAGATTCTCAGGATGGTCTTTACAATCCAGAAAAAGCACGGgCT    6720
 K  D  V  N  L  A  D  S  Q  D  G  L  Y  N  P  E  K  A  R  A

GAATTTCGTAAAGCTAAATTAGCCTTACAAGCAGAAGGAGTCCAATTCCCAATTCATTTA    6780
 E  F  R  K  A  K  L  A  L  Q  A  E  G  V  Q  F  P  I  H  L

GATATGCCAGTTGACCAGACAGCAACTACAAAAGTTCAGCGGGTCGTCCAATCTATGAAACAA    6840
 D  M  P  V  D  Q  T  A  T  T  K  V  Q  R  V  Q  S  M  K  Q

TCCTTGGAAGTAACTTTAGGAGCTGATAATGTCATTATTGATATCCAACAACTACAAAAA    6900
 S  L  E  V  T  L  G  A  D  N  V  I  I  D  I  Q  Q  L  Q  K
```

FIG. 6Iii

```
GACGAAGTAAACAATATTACATATTTGCTGAAAAATGCTGCTGGCGAAGACTGGGATTTA    6960
 D  E  V  N  N  I  T  Y  F  A  E  N  A  A  G  E  D  W  D  L

TCAGATAATGTCGGTTGGGGTCCAGACTTTGCCGATCCATCAACCTACCTTGATATCATC    7020
 S  D  N  V  G  W  G  P  D  F  A  D  P  S  T  Y  L  D  I  I

AAACCATCTCTGTAGGAGAAAGTACTAAAACATATTTAGGGTTTGACTCAGGGAAGATAAT    7080
 K  P  S  V  G  E  S  T  K  T  Y  L  G  F  D  S  G  E  D  N

GTAGCTGCTAAAAAAGTAGGTCTATATGACTACGAAAAATTGGTTACTGAGGCTGGTGAT    7140
 V  A  A  K  K  V  G  L  Y  D  Y  E  K  L  V  T  E  A  G  D

GAGGCTACAGATGTTCGTAAACGCTATGATAAATACGCTGCAGCCCAAGCTT            7192
 E  A  T  D  V  R  K  R  Y  D  K  Y  A  A  A  Q  A
```

FIG. 6Iiii transposase - nt 6366 to 5836, opposite orientation

```
TTAAATGCCTATTTCCAAATGCACAAATCGTCCTTGATAGATTTCATATCATCCAGCACC
 L  N  A  Y  F  Q  M  H  K  S  S  L  I  D  F  I  S  S  S  T

CTAAGCCGTGAGATGATGACAACCAGAATTGTCATCATGAAGAATTTTGACAAGCAATCA
 L  S  R  E  M  M  T  T  R  I  V  I  M  K  N  F  D  K  Q  S

CTTTCCTATCGCGCCATGAAAAATCACTGGGCGAATTTTCCAAAAGGATAGCCGAAAACTG
 L  S  Y  R  A  M  K  N  H  W  R  I  F  Q  K  D  S  R  K  L

TCTGATAAGGCCTTCTACTCAAGAACTTTTAGACAGACACCTGACACCTGAGAAATCGTC
 S  D  K  A  F  Y  S  R  T  F  R  Q  T  L  T  P  R  E  I  V

AATAAAACCCTTAGCTTTCTCAGATGAGCTCCACTATTATGACGATCTTTACCAGTCCTG
 N  K  T  L  A  F  S  D  E  L  H  Y  Y  D  D  L  Y  Q  L  L

CTTTTCCACCTGCAAGAAAAGAATGCCGACCATTTCTTTGACTTGTTAACTGAGGCTTTT
 L  F  H  L  Q  E  K  N  A  D  H  F  F  D  L  L  T  E  A  F
```

FIG. 6Ji

```
CCCAACTCAATCAAGCCTTTAGAACTGCTCTTAGCACGCTGGTGCGCTACAGAAAATAC
 P  Q  L  N  Q  A  F  R  T  A  L  S  T  L  V  R  Y  R  K  Y

GTGACAAATGCCATCCAGATGCCCTATTCTAACTCCAAGCTGGAGGCAATCAATAAACTC
 V  T  N  A  I  Q  M  P  Y  S  N  S  K  L  E  A  I  N  K  L

ATCAGCTTTCTTCAAACCCAAACATGTAGGTTATGTTTTCTTCAAATTCT
 I  S  F  L  Q  T  Q  T  C  R  L  C  F  S  S  N  S
```

FIG. 6Jii

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 300 bp
      (B) TYPE: nucleic acid
      (C) STRANDEDNESS: single-stranded
      (D) TOPOLOGY: linear (ii) MOLECULE TYPE:
      (A) DESCRIPTION: other nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO: 1:

```
GAGCTCGGTA TTTTTTGGAA CGTGATTTAG TTCATGTAGT TGCAAGTGAC ATGCACAATT    60

TAGACAGTAG ACCTCCATAT ATGCAACAGG CATATGATAT CATTGCTAAG AAATATAGAG   120

CGAAAAAAGC GAAAGAACTT TTTGTAGATA ATCCCAGAAA AATTATAATG GATCATTAAT   180

TAGGAGAAAA TATGAAGGAA CAAAACACTT TGGAAATCGA TGTATTGCAG TATTCAGAGC   240

TTATTGGAAG AAGTGTCATT TTATTAGTGG CATTATACTT CTTCAGTTGC TTTTTCCTAC   300
```

(2) INFORMATION FOR SEQ ID NO:2:

(i) SEQUENCE CHARACTERISTICS:
        (A) LENGTH:  261 bp
        (B) TYPE:  nucleic acid
        (C) STRANDEDNESS:  single-stranded
        (D) TOPOLOGY:  linear (ii) MOLECULE TYPE:
        (A) DESCRIPTION:  other nucleic acid (iii) HYPOTHETICAL:  no (iv) ANTI-SENSE:  no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO:   2:

```
CTTCCGTATG CCGCGTTCCT GCAAGACCCC ATCGGCTGGC TCTTTGATAG AGTAGCTGCC      60

CAAAAAATTA TCAGTATTAC TCGTGCTGAT GTGGCACACT GGAGGAGCAA GACCGCCGAT     120

ATCACCGCTT CGCCAAATAA TAAACGCAAT ACACTAATTG GTTTTTTGGC ATTTTTTATT     180

GGAACTAGTG TCATAGTTCT TCTTCTTGAA CTTTTGGACA CTCATGTGAA ACGTCCGGAA     240

GATATCGAAG ATACACTGCA G                                               261
```

(2) INFORMATION FOR SEQ ID NO:3:

(i) SEQUENCE CHARACTERISTICS:
        (A) LENGTH:  262 bp
        (B) TYPE:  nucleic acid
        (C) STRANDEDNESS:  single-stranded
        (D) TOPOLOGY:  linear (ii) MOLECULE TYPE:
        (A) DESCRIPTION:  other nucleic acid (iii) HYPOTHETICAL:  no (iv) ANTI-SENSE:  no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO:   3:

```
CAGCACTTCT CATCTGGCAC AGCTGATTTA TCTCACGGCT TATGTGATAC AAATATTGAA      60

AATTTATTTG TAGTTCAATC GGGATCTGTA TCACCAAACC CTACAGCCTT GTCACAAAGC     120

AAAAATTTTG TGGTTATGGT AAAGCTTTTT TCAAAAGAGG TCAGTATATT GAGTTGGTGG     180

AAACGATAAA ATACATAATA TTTTATTCCT TTGGTTATCA AATTAGCCCC TCCTGAAGCT     240

CCCCAATTGA CGGCTTGAGC TC                                              262
```

(2) INFORMATION FOR SEQ ID NO:4:

(i) SEQUENCE CHARACTERISTICS:
        (A) LENGTH:  934 bp
        (B) TYPE:  nucleic acid
        (C) STRANDEDNESS:  single-stranded
        (D) TOPOLOGY:  linear (ii) MOLECULE TYPE:
    (A) DESCRIPTION: other nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO:   4:

```
GAGCTCCAAT CAAAGGGTGT TTGTACACTT TTTGACAGAG GGTAATCGCT AGAGGACAGC      60
AAACAGCCAT AGTAGTGAAA AATCCAGACA CCTAAAGCAG ACAAAAGGGT TGCCATCAGG     120
TATAAAATCA TGTAGAGGGC GTTAGGGTAG GTGCGTGTGC GGTAGAGAAT GTGTTGAGCC     180
AAAACATCAA GAGTACCGTT AGTTATTGCA AAGTTATAAA AGAGAGAGAC GCTAAAAATG     240
GTAAAAAGAG TGAGTTGGCC AAAATGAAGA AGTTCTTTGG GGCTTAATCC CATGAGAGTG     300
GTTGCGATGA GGTAAGAAAA AGCAATAGCC AGCAGGTCAA TATTGATTTT GGTGCGGTAA     360
CCAATTCCAA TGGCTAGAGC AATGGCGCTA ATCATTATTA AATGAATCAT TGAATTGTCC     420
TTTAGTTAGA ATATAGAAAG AGGATAGATT GAAGTTCGAG AATACTGGGT GTCTTCTGAT     480
GTTAAGTGGT TGTGTCAAAA CCATCCCAAA TGGCATAAAT TGCAGTGGAA TTGGAATGAC     540
TCGTAATACT ATTGATAGAG ATGGTATTAC AAGTCAAGAC GTTCGCTATT TTATCTTTAA     600
CTTTAAGCTT AGTGTAGTAG CCTTTTGCCA TAGTGTTCGA GGTCATTGGT CAGCAGAAAG     660
TATGCATTGG TTATTGGATG TGGTTTATCG TGAAGACCAT CATCAGACCC TGGATAAACG     720
AGCTGCTTTT AACCTTAATC TTATCGAAAA ATGTGTTTAT ATTTTCTAAA AGTGATGGTA     780
TTTTCTAAAA AAGACCTCAG CTATCGATGC AAACAACGGT ATATCTCTGT ACATTTGGAA     840
GATTATTTGG AAACAGAGGT TAGGAAAGTA ATCAGTTAAC GGGATATCTT TTCAAAGCTG     900
ATACTAAGGC ACAAAAAAAA GTTTGATATT CCCC                                 934
```

(2) INFORMATION FOR SEQ ID NO:5:

(i) SEQUENCE CHARACTERISTICS:
        (A) LENGTH: 4951 bp
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO:   5:

```
TTGACAATAG ATAAAATTAT TATATAATTA AACTATTGCT TTTTAAATAA AGTGAGAATA      60
TTAATAATGC AGAGAAAGAG GACTGTAGTA AAATGAAAAT TGCCATTGCA GGAAGTGGTT     120
```

```
ATGTAGGTCT GTCTTTAGCG GTGCTACTAG CTCAGCATCA TGAAGTTAAG GTCATTGATG    180

TTATAAGGA TAAGGTAGAG TCGATAAACA ATAGAAAATC TCCAATTAAG GATGAGGCGA    240

TTGAGAAATA CTTAGTTGAA AAAGAGTTGA ATCTTGAAGC CTCCTTAGAT CCTGCACACG    300

TTTATAAAGA CGTGGAGTAT GCTATTATTG CTACTCCGAC TAATTATGAT GTAGACTTAA    360

ATCAGTTTGA TACATCTTCA GTTGAAGCTG CTATCAAGAC TTGTATGGAA TATAATGATA    420

CTTGTACAAT CGTAATCAAA AGTACTATTC CTGAAGGGTA TACTAAAGAA GTGAGGGAAA    480

AGTTTAATAC AGATCGTATT ATTTTTTCTC CAGAGTTTCT ACGTGAATCC AAAGCTTTAT    540

ATGATAATTT GTATCCATCT AGAATTGTTG TAGGAACTGA TTTGGATGAT TCTGAGTTAA    600

CAAAAAGAGC ATGGCAGTTT GCAGATCTAC TTAAAGGTGG AGCTATTAAG GAAGAGGTTC    660

CGATACTGGT TGTTGCTTTT AATGAAGCAG AGGTTGCAAA ATTGTTTAGT AACACTTACT    720

TGGCAACTCG CGTAGCTTAT TTTAATGAGA TAGATACATA TAGCGAGGTA AAAGGGCTTA    780

ATCCCAAGAC AATTATTGAT ATTGTTTGTT ATGATCCTAG AATTGGATCA GACTATAATA    840

ACCCTAGCTT TGGTTACGGA GGGTATTGCT TACCAAAAGA CACAAAGCAA TTGAAAGCAA    900

GTTTTAGGGA TGTTCCTGAA AATCTGATTA CAGCTGTGGT GCAATCTAAT AAAACAAGAA    960

AAGATTATAT AGCTGGAGCT ATTCTAGCTA ACAACCTAG TGTTGTAGGT ATTTATAGAT   1020

TAATTATGAA ATCTGATTCT GATAATTTTC GTTCTAGTGC TGTTAAGGGA GTTATGGAAC   1080

GTTTGGACAA TTATGGTAAA GAAATTGTTA TTTACGAACC TACTATTGAG TGTGATACTT   1140

TTATGGGATA CAGAGTAATT AAATCTTTAG ATGAATTTAA GAATATTTCT GACATTGTTG   1200

TAGCGAATCG TATGAACGAT GATTTAAGGG ATATACAAGA AAAACTCTAT ACACGCGATT   1260

TATTTGGCAG AGAATAAGGG GAAATAATTT TTATGTATAC ATTTATTTTA ATGTTGTTGG   1320

ATTTTTTTCA GAATCATGAT TTTCATTTCT TTATGTTGTT TTTTGTCTTT ATTCTTATTC   1380

GTTGGGCGGT TATATATTTT CATGCTGTCA GATATAAGTC CTACAGTTGT AGTGTAAGTG   1440

ATGAGAAGTT ATTTAGTTCT GTAATTATCC CTGTCGTGGA TGAACCACTT AATCTTTTTG   1500

AAAGTGTACT GAATAGAATT TCCAGACATA AACCATCCGA AATTATTGTG GTTATTAACG   1560

GCCCAAAAAA CGAGAGACTT GTAAAACTTT GTCATGATTT TAATGAAAAA TTAGAAAATA   1620

ATATGACTCC AATTCAATGT TATTACACTC CTGTTCCTGG CAAGAGAAAT GCTATCCGCG   1680

TTGGGCTGGA GCATGTGGAT TCGCAGAGTG ATATTACAGT TCTAGTAGAT AGTGATACAG   1740

TATGGACGCC TAGAACCTTG AGTGAGTTGC TGAAGCCTTT TGTTTGCGAT AAAAAAATAG   1800

GTGGGGTAAC GACAAGACAA AAAATTCTTG ACCCTGAGCG TAATCTCGTG ACAATGTTTG   1860

CTAACTTGTT AGAGGAAATT AGGGCAGAAG GAACTATGAA AGCAATGAGT GTGACTGGTA   1920

AAGTAGGGTG CTTACCTGGT CGAACAATTG CTTTTAGAAA TATAGTGGAG AGAGTGTATA   1980

CAAAGTTTAT AAAAGAGACTT TCATGGGATT TCATAAGGAA GTTTCTGATG ATAGAACGTC   2040

TTACAAATTT GACTTTAAAA AAAGGCTATA AAACTGTTAT GCAGGATACT TCTGTTGTGT   2100

ATACAGATGC TCCTACAAGT TGGAAAAAGT TCATTAGACA GCAACTAAGG TGGGCAGAAG   2160

GTTCTCAGTA TAACAATCTA AAGATGACTC CTTGGATGAT TAGAAATGCC CCTCTTATGT   2220

TTTTTATTTA TTTTACAGAT ATGATTTTAC CTATGCTACT TATTAGCTTT GGTGTGAATA   2280

TATTCCTGTT GAAAATATTA AATATAACTA CAATTGTTTA TACAGCTTCA TGGTGGGAAA   2340

TTATTTTATA TGTTCTTTTG GGAATGATTT TTAGCTTTGG AGGAAGAAAC TTTAAAGCTA   2400

TGTCTAGAAT GAAGTGGTAT TATGTATTTC TTATTCCTGT TTTTATAATC GTTTTGAGTA   2460

TAATTATGTG CCCTATTAGG CTATTAGGAC TTATGAGATG TTCTGATGAT TTAGGGTGGG   2520
```

```
GAACTAGGAA TTTAACAGAG TGAGATAAAT AGTAGTGCGT ATATAGAGTA TTTACTCAGA    2580

GTATTAATTG ATTTTTGAAA AGGAAAAGTG TTTTTTAATG TTAAGAAAGA ACTTGAAATA    2640

TCAGATTATG ACACGAGCTG GAACAATTTT AGCTATCTTG TTTTTCATTA TATTAGGGAT    2700

TATTGTTGAA GTTTTGTTTT AAGGCTCATT GTCATCTGTA GTGGCTCACT TCAGACGTAA    2760

GGGTCATATT TTAATGTGAA AAGAGTGTTA AAAGATTAAT CACTTATATT ATTTTAATAG    2820

AAATAGTGTA AGGAATTGTT ATGAAAAAAG TAAAAAAAGC TGTTATTCCT GCTGCAGGGC    2880

TGGGCACACG ATTTTTGCCT GCCACTAAAG CTTTGGCAAA AGAAATGCTT CCAATTGTAG    2940

ACCGCCCCAC AATTCATTTT GTCATTGAAG AAGCTTTACG TTCGGGTATT GAAGATATTC    3000

TAGTAGTTAC TGGAAAGAGT AAACGTTCTA TTGAAGATTA TTTTGATTCA ACTTTTGAAT    3060

TGGAATATAG TCTTAGAAAA CAAGGAAAGA TGGAACTTCT TAAGTCAGTT AACGAATCGA    3120

CTGATATTAA AGTACATTTC GTTCGTCAAA GTTCACCACG TGGTCTTGGT GACGCTGTTC    3180

TCCAAGCGAA GTCTTTTGTT GGTGACGATC CCTTTGTTGT AATGCTTGGT GATGACCTTA    3240

TGGATATCAC CGACTCAACT GCTGTACCTT TAACAAGACA ATTGATGGAT GATTACAACG    3300

CAACACAGGC TTCAACTATC GCAGTAATGC CTGTTAGATA TGAAGATGTT TCTTCTTATG    3360

GTGTGATTTC TCCTAGATTG GAAAGTAGTA ATGGCCTCTA TAGTGTTGAT GCTTTTGTAG    3420

AGAAACCAAA ACCAGAAGAA GCGCCTAGCC ATTTAGCTAT TATTGGACGT TATCTACTTA    3480

CTCCTGAGAT TTTTTCTATA TTAGAAACCC AAAAGCCAGG AGCAGGTAAT GAAATTCAAT    3540

TGACAGATGC TATTGATACA TTGAATAAGA CACAGAGTGT TTTTGCGCGT GAATTTGTGG    3600

GCAAACGTTA CGATGTTGGT GATAAGTTTA ATTTTATGAA AACATCAATT GATTATGCTC    3660

TTCAACATCC TCAGATTAAA GAGAGTTTAA AAAATTACGT TATTGCACTT GGTAAGCAAT    3720

TGGAGAAGCT AGATGACTGT TCGTCAAGTG GACACCTATG AATTGTATAG AAAGTTATCA    3780

AAAATGGCTA AATGTCCCTG ATCTTCCAGC TTATTTAAAA GATGAATTGC TCAGCATGGA    3840

TGACAAAACA AAAGAAGACG CCTTTTACAC AAACCTTGAA TTCGGAACAG CTGGTATGCG    3900

TGGTTATATT GGTGCTGGGA CAAACCGTAT TAATATCTAT GTGGTGCGTC AAGCACACAG    3960

AAGGCCTTGC AAATTAGTTG AATCAAAAGG CGAAACCGCC AAAAAAGCTG GGGTTGCTAT    4020

TGCCTATGAC TCGCGACATT TTTCACCAGA ATTCGCTTTT GAATCTGCCC AAGTATTAGC    4080

GGCCCATGGC ATTAAATCTT ATGTTTTTGA AAGCCTACGC CCTACTCCTG AGCTGTCTTT    4140

TGCTGTTCGT CATCTCGGAG CATTTGCTGG TATTATGGTA ACCGCCAGTC ATACCCCTGC    4200

TCCTTTTAAT GGTTATAAAG TTTACGGTTC TGATGGTGGG CAAATGCTTC CAGCTGACTA    4260

TATTCGTGCG ATTGATAACC CATTTGCTGT AGTCCTTGCT GACTTAGAAG AAGCTAAATC    4320

AACTGGTCTT ATTGAAGTAA TTGGTGAAAC TCTCGATGCT GCCTACCTTG AAGAGGTTAA    4380

AAGCGTTAAT ATCAATCAAG ATTTGATTGA CCAATACGGT CGCGATATGC AAATTGTCTA    4440

CACACCTCTT CATGGTACTG GAGAAATGCT AGCACGTCGA GCTTTAGCAC AAGCTGGTTT    4500

CGAATCTGTT CAAGTTGTCG AAGCTCAAGC AAAACCAGAC CCAGACTTCT CAACAGTTGC    4560

ATCACCAAAC CCTGAAAGTC AAGCCGCCTT TGCCTTAGCT GAAGAACTAG GGCGTCAAGT    4620

CGATGCTGAT GTATTAGTGG CGACTGACCC TGATGCTGAC CGTCTCGGTG TTGAAATTCG    4680

TCAAGCTGAT GGCAGTTATT GGAACCTTTC TGGTAACCAA ATCGGTGCTC TTATCGCCAA    4740

ATACATTTTA GAAGCTCACA AACAAGCTGG GACACTCCCA AAGAATGCTG CATTGGCAAA    4800

ATCAATAGTA TCAACTGAAT TAGTCACCAA AATTGCGGAA AGCTATGGCG AACCATGTTT    4860

AACGTCATTA CAGGTTTCAA ATTCATCGCT GAGAAAATTC AAGAATTTGA AGAAAAACAT    4920
```

AACCTACATG TTTGGGTTTG AAGAAAGCTG A                                    4951

(2) INFORMATION FOR SEQ ID NO:6:

(i) SEQUENCE CHARACTERISTICS:
        (A) LENGTH: 1307 bp
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO: 6:

```
TGAGTTTATT GATTGCCTCC AGCTTGGAGT TAGAATAGGG CATCTGGATG GCATTTGTCA      60

CGTATTTTCT GTAGCGCACC AGCGTGCTAA GAGCAGTTCT AAAGGCTTGA TTGAGTTGGG     120

GAAAAGCCTC AGTTAACAAG TCAAAGAAAT GGTCGGCATT CTTTTCTTGC AGGTGGAAAA     180

GCAGGAGCTG GTAAAGATCG TCATAATAGT GGAGCTCATC TGAGAAAGCT AAGGTTTTAT     240

TGACGATTTC TCGAGGTGTC AGTGTCTGTC TAAAAGTTCT TGAGTAGAAG GCCTTATCAG     300

ACAGTTTTCG GCTATCCTTT TGGAAAATTC GCCAGTGATT TTTCATGGCG CGATAGGAAA     360

GTGATTGCTT GTCAAAATTC TTCATGATGA CAATTCTGGT TGTCATCATC TCACGGCTTA     420

GGGTGCTGGA TGATATGAAA TCTATCAAGG ACGATTTGTG CATTTGGAAA TAGGCATTTA     480

ATCACAAGAC TCTATTACGT ATCTAGTTGG TCAAATATTC GACCGTCAGT CCTATAAATA     540

TACATCTAAG ACCAGAGAAG AACAAAAAAC ATCTACGAAA AAGGCTCTCT TAAACAAGGA     600

TTTCCGTCAA GCTATTGCAT TTGGATTTGA CCGTTATGCC TCTCAGTTGA ATGGACAAAC     660

TGGAGCAAGC AAAATCTTAC GTAATCTCTT TGTCCCACCA ACATTTGTTC AAGCAGATGG     720

CAAAAACTTT GGCGATATGG CCAAAGAGAA ATTGGTCACT TATGGGGATG AATGGAAGGA     780

TGTTAATCTT GCAGATTCTC AGGATGGTCT TTACAATCCA GAAAAAGCAC GGGCTGAATT     840

TCGTAAAGCT AAATTAGCCT TACAAGCAGA AGGAGTCCAA TTCCCAATTC ATTTAGATAT     900

GCCAGTTGAC CAGACAGCAA CTACAAAAGT TCAGCGCGTC CAATCTATGA AACAATCCTT     960

GGAAGTAACT TTAGGAGCTG ATAATGTCAT TATTGATATC CAACAACTAC AAAAAGACGA    1020

AGTAAACAAT ATTACATATT TGCTGAAAAA TGCTGCTGGC GAAGACTGGG ATTTATCAGA    1080

TAATGTCGGT TGGGGTCCAG ACTTTGCCGA TCCATCAACC TACCTTGATA TCATCAAACC    1140

ATCTGTAGGA GAAAGTACTA AAACATATTT AGGGTTTGAC TCAGGGGAAG ATAATGTAGC    1200

TGCTAAAAAA GTAGGTCTAT ATGACTACGA AAAATTGGTT ACTGAGGCTG GTGATGAGGC    1260

TACAGATGTT CGTAAACGCT ATGATAAATA CGCTGCAGCC CAAGCTT                 1307
```

(2) INFORMATION FOR SEQ ID NO:7:

(i) SEQUENCE CHARACTERISTICS:
        (A) LENGTH: 58 amino acids
        (B) TYPE: amino acid

```
        (C) STRANDEDNESS:
        (D) TOPOLOGY:  linear (ii) MOLECULE TYPE:
        (A) DESCRIPTION:  protein (iii) HYPOTHETICAL:  no (iv) ANTI-SENSE:  no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO:   7:

Ala Arg Tyr Phe Leu Glu Arg Asp Leu Val His Val Val Ala Ser Asp Met
 1               5                  10                  15

His Asn Leu Asp Ser Arg Pro Pro Tyr Met Gln Gln Ala Tyr Asp Ile Ile
            20                  25                  30

Ala Lys Lys Tyr Arg Ala Lys Lys Ala Lys Glu Leu Phe Val Asp Asn Pro
35                  40                  45                  50

Arg Lys Ile Ile Met Asp His
            55

(2) INFORMATION FOR SEQ ID NO:8:

(i) SEQUENCE CHARACTERISTICS:
        (A) LENGTH:  40 amino acids
        (B) TYPE:  amino acid
        (C) STRANDEDNESS:
        (D) TOPOLOGY:  linear (ii) MOLECULE TYPE:
        (A) DESCRIPTION:  protein (iii) HYPOTHETICAL:  no (iv) ANTI-SENSE:  no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO:   8:

Leu Gly Glu Asn Met Lys Glu Gln Asn Thr Leu Glu Ile Asp Val Leu Gln
 1               5                  10                  15

Tyr Ser Glu Leu Ile Gly Arg Ser Val Ile Leu Leu Val Ala Leu Tyr Phe
            20                  25                  30

Phe Ser Cys Phe Phe Leu
35                  40

(2) INFORMATION FOR SEQ ID NO:9:

(i) SEQUENCE CHARACTERISTICS:
        (A) LENGTH:  87 amino acids
        (B) TYPE:  amino acid
        (C) STRANDEDNESS:
        (D) TOPOLOGY:  linear (ii) MOLECULE TYPE:
        (A) DESCRIPTION:  protein (iii) HYPOTHETICAL:  no
```

(iv) ANTI-SENSE:  no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO:   9:

Leu Pro Tyr Ala Ala Phe Leu Gln Asp Pro Ile Gly Trp Leu Phe Asp Arg
  1               5                  10                  15

Val Ala Ala Gln Lys Ile Ile Ser Ile Thr Arg Ala Asp Val Ala His Trp
             20                  25                  30

Arg Ser Lys Thr Ala Asp Ile Thr Ala Ser Pro Asn Asn Lys Arg Asn Thr
 35                  40                  45                  50

Leu Ile Gly Phe Leu Ala Phe Phe Ile Gly Thr Ser Val Ile Val Leu Leu
                 55                  60                  65

Leu Glu Leu Leu Asp Thr His Val Lys Arg Pro Glu Asp Ile Glu Asp Thr
 70                  75                  80                  85

Leu Gln (2) INFORMATION FOR SEQ ID NO:10:

(i) SEQUENCE CHARACTERISTICS:
          (A) LENGTH:  43 amino acids
          (B) TYPE:  amino acid
          (C) STRANDEDNESS:
          (D) TOPOLOGY:  linear (ii) MOLECULE TYPE:
          (A) DESCRIPTION:  protein (iii) HYPOTHETICAL:  no (iv) ANTI-SENSE:  no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO:   10:

Gln His Phe Ser Ser Gly Thr Ala Asp Leu Ser His Gly Leu Cys Asp Thr
  1               5                  10                  15

Asn Ile Glu Asn Leu Phe Val Val Gln Ser Gly Ser Val Ser Pro Asn Pro
             20                  25                  30

Thr Ala Leu Ser Gln Ser Lys Asn Phe
 35                  40

(2) INFORMATION FOR SEQ ID NO:11:

(i) SEQUENCE CHARACTERISTICS:
          (A) LENGTH:  394 amino acids
          (B) TYPE:  amino acid
          (C) STRANDEDNESS:
          (D) TOPOLOGY:  linear (ii) MOLECULE TYPE:
          (A) DESCRIPTION:  protein (iii) HYPOTHETICAL:  no (iv) ANTI-SENSE:  no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO: 11:

```
Met Lys Ile Ala Ile Ala Gly Ser Gly Tyr Val Gly Leu Ser Leu Ala Val
1               5                   10                  15

Leu Leu Ala Gln His His Glu Val Lys Val Ile Asp Val Ile Lys Asp Lys
            20                  25                  30

Val Glu Ser Ile Asn Asn Arg Lys Ser Pro Ile Lys Asp Glu Ala Ile Glu
35              40                  45                  50

Lys Tyr Leu Val Glu Lys Glu Leu Asn Leu Glu Ala Ser Leu Asp Pro Ala
                55                  60                  65

His Val Tyr Lys Asp Val Glu Tyr Ala Ile Ile Ala Thr Pro Thr Asn Tyr
            70                  75                  80                  85

Asp Val Asp Leu Asn Gln Phe Asp Thr Ser Ser Val Glu Ala Ala Ile Lys
                90                  95                  100

Thr Cys Met Glu Tyr Asn Asp Thr Cys Thr Ile Val Ile Lys Ser Thr Ile
            105                 110                 115

Pro Glu Gly Tyr Thr Lys Glu Val Arg Glu Lys Phe Asn Thr Asp Arg Ile
120                 125                 130                 135

Ile Phe Ser Pro Glu Phe Leu Arg Glu Ser Lys Ala Leu Tyr Asp Asn Leu
            140                 145                 150

Tyr Pro Ser Arg Ile Val Val Gly Thr Asp Leu Asp Asp Ser Glu Leu Thr
155                 160                 165                 170

Lys Arg Ala Trp Gln Phe Ala Asp Leu Leu Lys Gly Gly Ala Ile Lys Glu
            175                 180                 185

Glu Val Pro Ile Leu Val Val Ala Phe Asn Glu Ala Glu Val Ala Lys Leu
            190                 195                 200

Phe Ser Asn Thr Tyr Leu Ala Thr Arg Val Ala Tyr Phe Asn Glu Ile Asp
205                 210                 215                 220

Thr Tyr Ser Glu Val Lys Gly Leu Asn Pro Lys Thr Ile Ile Asp Ile Val
            225                 230                 235

Cys Tyr Asp Pro Arg Ile Gly Ser Asp Tyr Asn Asn Pro Ser Phe Gly Tyr
240                 245                 250                 255

Gly Gly Tyr Cys Leu Pro Lys Asp Thr Lys Gln Leu Lys Ala Ser Phe Arg
            260                 265                 270

Asp Val Pro Glu Asn Leu Ile Thr Ala Val Val Gln Ser Asn Lys Thr Arg
            275                 280                 285

Lys Asp Tyr Ile Ala Gly Ala Ile Leu Ala Lys Gln Pro Ser Val Val Gly
290                 295                 300                 305

Ile Tyr Arg Leu Ile Met Lys Ser Asp Ser Asp Asn Phe Arg Ser Ser Ala
            310                 315                 320

Val Lys Gly Val Met Glu Arg Leu Asp Asn Tyr Gly Lys Glu Ile Val Ile
325                 330                 335                 340

Tyr Glu Pro Thr Ile Glu Cys Asp Thr Phe Met Gly Tyr Arg Val Ile Lys
            345                 350                 355

Ser Leu Asp Glu Phe Lys Asn Ile Ser Asp Ile Val Val Ala Asn Arg Met
            360                 365                 370

Asn Asp Asp Leu Arg Asp Ile Gln Glu Lys Leu Tyr Thr Arg Asp Leu Phe
            375                 380                 385                 390
```

Gly Arg Glu (2) INFORMATION FOR SEQ ID NO:12:

(i) SEQUENCE CHARACTERISTICS:
        (A) LENGTH: 416 amino acids
        (B) TYPE: amino acid
        (C) STRANDEDNESS:
        (D) TOPOLOGY: linear (ii) MOLECULE TYPE:
        (A) DESCRIPTION: protein (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO: 12:

```
Met Tyr Thr Phe Ile Leu Met Leu Leu Asp Phe Phe Gln Asn His Asp Phe
 1               5                  10                  15

His Phe Phe Met Leu Phe Phe Val Phe Ile Leu Ile Arg Trp Ala Val Ile
             20                  25                  30

Tyr Phe His Ala Val Arg Tyr Lys Ser Tyr Ser Cys Ser Val Ser Asp Glu
 35                  40                  45                  50

Lys Leu Phe Ser Ser Val Ile Ile Pro Val Val Asp Glu Pro Leu Asn Leu
                 55                  60                  65

Phe Glu Ser Val Leu Asn Arg Ile Ser Arg His Lys Pro Ser Glu Ile Ile
 70                  75                  80                      85

Val Val Ile Asn Gly Pro Lys Asn Glu Arg Leu Val Lys Leu Cys His Asp
                 90                  95                 100

Phe Asn Glu Lys Leu Glu Asn Asn Met Thr Pro Ile Gln Cys Tyr Tyr Thr
                105                 110                 115

Pro Val Pro Gly Lys Arg Asn Ala Ile Arg Val Gly Leu Glu His Val Asp
120                 125                 130                 135

Ser Gln Ser Asp Ile Thr Val Leu Val Asp Ser Asp Thr Val Trp Thr Pro
                140                 145                 150

Arg Thr Leu Ser Glu Leu Leu Lys Pro Phe Val Cys Asp Lys Lys Ile Gly
155                 160                 165                 170

Gly Val Thr Thr Arg Gln Lys Ile Leu Asp Pro Glu Arg Asn Leu Val Thr
                175                 180                 185

Met Phe Ala Asn Leu Leu Glu Glu Ile Arg Ala Glu Gly Thr Met Lys Ala
                190                 195                 200

Met Ser Val Thr Gly Lys Val Gly Cys Leu Pro Gly Arg Thr Ile Ala Phe
205                 210                 215                 220

Arg Asn Ile Val Glu Arg Val Tyr Thr Lys Phe Ile Glu Glu Thr Phe Met
                225                 230                 235

Gly Phe His Lys Glu Val Ser Asp Asp Arg Ser Leu Thr Asn Leu Thr Leu
240                 245                 250                 255

Lys Lys Gly Tyr Lys Thr Val Met Gln Asp Thr Ser Val Val Tyr Thr Asp
                260                 265                 270

Ala Pro Thr Ser Trp Lys Lys Phe Ile Arg Gln Gln Leu Arg Trp Ala Glu
                275                 280                 285

Gly Ser Gln Tyr Asn Asn Leu Lys Met Thr Pro Trp Met Ile Arg Asn Ala
```

```
                  290               295               300               305
     Pro Leu Met Phe Phe Ile Tyr Phe Thr Asp Met Ile Leu Pro Met Leu Leu
                     310               315               320

Ile Ser Phe Gly Val Asn Ile Phe Leu Leu Lys Ile Leu Asn Ile Thr Thr
     325               330               335               340

Ile Val Tyr Thr Ala Ser Trp Trp Glu Ile Ile Leu Tyr Val Leu Leu Gly
                     345               350               355

Met Ile Phe Ser Phe Gly Gly Arg Asn Phe Lys Ala Met Ser Arg Met Lys
                     360               365               370

Trp Tyr Tyr Val Phe Leu Ile Pro Val Phe Ile Ile Val Leu Ser Ile Ile
                     375               380               385               390

Met Cys Pro Ile Arg Leu Leu Gly Leu Met Arg Cys Ser Asp Asp Leu Gly
                     395               400               405

Trp Gly Thr Arg Asn Leu Thr Glu
                     410               415
```

(2) INFORMATION FOR SEQ ID NO:13:

(i) SEQUENCE CHARACTERISTICS:
        (A) LENGTH: 306 amino acids
        (B) TYPE: amino acid
        (C) STRANDEDNESS:
        (D) TOPOLOGY: linear (ii) MOLECULE TYPE:
        (A) DESCRIPTION: protein (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO: 13:

```
Met Lys Lys Val Lys Lys Ala Val Ile Pro Ala Ala Gly Leu Gly Thr Arg
1               5                   10                  15

Phe Leu Pro Ala Thr Lys Ala Leu Ala Lys Glu Met Leu Pro Ile Val Asp
                20                  25                  30

Arg Pro Thr Ile His Phe Val Ile Glu Glu Ala Leu Arg Ser Gly Ile Glu
35                  40                  45                  50

Asp Ile Leu Val Val Thr Gly Lys Ser Lys Arg Ser Ile Glu Asp Tyr Phe
                55                  60                  65

Asp Ser Thr Phe Glu Leu Glu Tyr Ser Leu Arg Lys Gln Gly Lys Met Glu
70                  75                  80                  85

Leu Leu Lys Ser Val Asn Glu Ser Thr Asp Ile Lys Val His Phe Val Arg
                90                  95                  100

Gln Ser Ser Pro Arg Gly Leu Gly Asp Ala Val Leu Gln Ala Lys Ser Phe
                105                 110                 115

Val Gly Asp Asp Pro Phe Val Val Met Leu Gly Asp Asp Leu Met Asp Ile
120                 125                 130                 135

Thr Asp Ser Thr Ala Val Pro Leu Thr Arg Gln Leu Met Asp Asp Tyr Asn
                140                 145                 150

Ala Thr Gln Ala Ser Thr Ile Ala Val Met Pro Val Arg Tyr Glu Asp Val
                155                 160                 165                 170

Ser Ser Tyr Gly Val Ile Ser Pro Arg Leu Glu Ser Ser Asn Gly Leu Tyr
```

```
                175                 180                 185
Ser Val Asp Ala Phe Val Glu Lys Pro Lys Pro Glu Ala Pro Ser His
            190                 195                 200

Leu Ala Ile Ile Gly Arg Tyr Leu Leu Thr Pro Glu Ile Phe Ser Ile Leu
205                 210                 215                 220

Glu Thr Gln Lys Pro Gly Ala Gly Asn Glu Ile Gln Leu Thr Asp Ala Ile
            225                 230                 235

Asp Thr Leu Asn Lys Thr Gln Ser Val Phe Ala Arg Glu Phe Val Gly Lys
        240                 245                 250                 255

Arg Tyr Asp Val Gly Asp Lys Phe Asn Phe Met Lys Thr Ser Ile Asp Tyr
                260                 265                 270

Ala Leu Gln His Pro Gln Ile Lys Glu Ser Leu Lys Asn Tyr Val Ile Ala
            275                 280                 285

Leu Gly Lys Gln Leu Glu Lys Leu Asp Asp Cys Ser Ser Ser Gly His Leu
290                 295                 300                 305
```

(2) INFORMATION FOR SEQ ID NO:14:

(i) SEQUENCE CHARACTERISTICS:
        (A) LENGTH: 397 amino acids
        (B) TYPE: amino acid
        (C) STRANDEDNESS:
        (D) TOPOLOGY: linear (ii) MOLECULE TYPE:
        (A) DESCRIPTION: protein (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO: 14:

```
Met Asn Cys Ile Glu Ser Tyr Gln Lys Trp Leu Asn Val Pro Asp Leu Pro
1               5                   10                  15

Ala Tyr Leu Lys Asp Glu Leu Leu Ser Met Asp Asp Lys Thr Lys Glu Asp
            20                  25                  30

Ala Phe Tyr Thr Asn Leu Glu Phe Gly Thr Ala Gly Met Arg Gly Tyr Ile
35                  40                  45                  50

Gly Ala Gly Thr Asn Arg Ile Asn Ile Tyr Val Val Arg Gln Ala His Arg
            55                  60                  65

Arg Pro Cys Lys Leu Val Glu Ser Lys Gly Glu Thr Ala Lys Lys Ala Gly
70                  75                  80                  85

Val Ala Ile Ala Tyr Asp Ser Arg His Phe Ser Pro Glu Phe Ala Phe Glu
                90                  95                  100

Ser Ala Gln Val Leu Ala Ala His Gly Ile Lys Ser Tyr Val Phe Glu Ser
            105                 110                 115

Leu Arg Pro Thr Pro Glu Leu Ser Phe Ala Val Arg His Leu Gly Ala Phe
120                 125                 130                 135

Ala Gly Ile Met Val Thr Ala Ser His Thr Pro Ala Pro Phe Asn Gly Tyr
                140                 145                 150

Lys Val Tyr Gly Ser Asp Gly Gly Gln Met Leu Pro Ala Asp Tyr Ile Arg
            155                 160                 165                 170

Ala Ile Asp Asn Pro Phe Ala Val Val Leu Ala Asp Leu Glu Glu Ala Lys
```

-continued

```
                175                 180                 185
Ser Thr Gly Leu Ile Glu Val Ile Gly Glu Thr Leu Asp Ala Ala Tyr Leu
            190                 195                 200

Glu Glu Val Lys Ser Val Asn Ile Asn Gln Asp Leu Ile Asp Gln Tyr Gly
205                 210                 215                 220

Arg Asp Met Gln Ile Val Tyr Thr Pro Leu His Gly Thr Gly Glu Met Leu
            225                 230                 235

Ala Arg Arg Ala Leu Ala Gln Ala Gly Phe Glu Ser Val Gln Val Val Glu
240                 245                 250                 255

Ala Gln Ala Lys Pro Asp Pro Asp Phe Ser Thr Val Ala Ser Pro Asn Pro
            260                 265                 270

Glu Ser Gln Ala Ala Phe Ala Leu Ala Glu Glu Leu Gly Arg Gln Val Asp
            275                 280                 285

Ala Asp Val Leu Val Ala Thr Asp Pro Asp Ala Asp Arg Leu Gly Val Glu
290                 295                 300                 305

Ile Arg Gln Ala Asp Gly Ser Tyr Trp Asn Leu Ser Gly Asn Gln Ile Gly
            310                 315                 320

Ala Leu Ile Ala Lys Tyr Ile Leu Glu Ala His Lys Gln Ala Gly Thr Leu
            325                 330                 335                 340

Pro Lys Asn Ala Ala Leu Ala Lys Ser Ile Val Ser Thr Glu Leu Val Thr
                345                 350                 355

Lys Ile Ala Glu Ser Tyr Gly Glu Pro Cys Leu Thr Ser Leu Gln Val Ser
            360                 365                 370

Asn Ser Ser Leu Arg Lys Phe Lys Asn Leu Lys Lys Asn Ile Thr Tyr Met
375                 380                 385                 390

Phe Gly Phe Glu Glu Ser
            395
```

(2) INFORMATION FOR SEQ ID NO:15:

(i) SEQUENCE CHARACTERISTICS:
        (A) LENGTH: 274 amino acids
        (B) TYPE: amino acid
        (C) STRANDEDNESS:
        (D) TOPOLOGY: linear (ii) MOLECULE TYPE:
        (A) DESCRIPTION: protein (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO: 15:

```
Gln Asp Ser Ile Thr Tyr Leu Val Gly Gln Ile Phe Asp Arg Gln Ser Tyr
1               5                   10                  15

Lys Tyr Thr Ser Lys Thr Arg Glu Glu Gln Lys Thr Ser Thr Lys Lys Ala
            20                  25                  30

Leu Leu Asn Lys Asp Phe Arg Gln Ala Ile Ala Phe Gly Phe Asp Arg Tyr
35                  40                  45                  50

Ala Ser Gln Leu Asn Gly Gln Thr Gly Ala Ser Lys Ile Leu Arg Asn Leu
                55                  60                  65

Phe Val Pro Pro Thr Phe Val Gln Ala Asp Gly Lys Asn Phe Gly Asp Met
```

```
                    70                  75                  80                  85
Ala Lys Glu Lys Leu Val Thr Tyr Gly Asp Glu Trp Lys Asp Val Asn Leu
                        90                  95                 100
Ala Asp Ser Gln Asp Gly Leu Tyr Asn Pro Glu Lys Ala Arg Ala Glu Phe
               105                 110                 115
Arg Lys Ala Lys Leu Ala Leu Gln Ala Glu Gly Val Gln Phe Pro Ile His
120                 125                 130                 135
Leu Asp Met Pro Val Asp Gln Thr Ala Thr Thr Lys Val Gln Arg Val Gln
                140                 145                 150
Ser Met Lys Gln Ser Leu Glu Val Thr Leu Gly Ala Asp Asn Val Ile Ile
155                 160                 165                 170
Asp Ile Gln Gln Leu Gln Lys Asp Glu Val Asn Asn Ile Thr Tyr Phe Ala
                175                 180                 185
Glu Asn Ala Ala Gly Glu Asp Trp Asp Leu Ser Asp Asn Val Gly Trp Gly
                190                 195                 200
Pro Asp Phe Ala Asp Pro Ser Thr Tyr Leu Asp Ile Ile Lys Pro Ser Val
205                 210                 215                 220
Gly Glu Ser Thr Lys Thr Tyr Leu Gly Phe Asp Ser Gly Glu Asp Asn Val
                225                 230                 235
Ala Ala Lys Lys Val Gly Leu Tyr Asp Tyr Glu Lys Leu Val Thr Glu Ala
240                 245                 250                 255
Gly Asp Glu Ala Thr Asp Val Arg Lys Arg Tyr Asp Lys Tyr Ala Ala Ala
                260                 265                 270
Gln Ala (2) INFORMATION FOR SEQ ID NO:16:

(i) SEQUENCE CHARACTERISTICS:
        (A) LENGTH:  177 amino acids
        (B) TYPE:  amino acid
        (C) STRANDEDNESS:
        (D) TOPOLOGY:  linear (ii) MOLECULE TYPE:
        (A) DESCRIPTION:  protein (iii) HYPOTHETICAL:  no (iv) ANTI-SENSE:  no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO:   16:

Leu Asn Ala Tyr Phe Gln Met His Lys Ser Ser Leu Ile Asp Phe Ile Ser
1                   5                  10                  15
Ser Ser Thr Leu Ser Arg Glu Met Met Thr Thr Arg Ile Val Ile Met Lys
                20                  25                  30
Asn Phe Asp Lys Gln Ser Leu Ser Tyr Arg Ala Met Lys Asn His Trp Arg
35                  40                  45                  50
Ile Phe Gln Lys Asp Ser Arg Lys Leu Ser Asp Lys Ala Phe Tyr Ser Arg
                55                  60                  65
Thr Phe Arg Gln Thr Leu Thr Pro Arg Glu Ile Val Asn Lys Thr Leu Ala
                70                  75                  80                  85
Phe Ser Asp Glu Leu His Tyr Tyr Asp Asp Leu Tyr Gln Leu Leu Leu Phe
                90                  95                 100
```

```
His Leu Gln Glu Lys Asn Ala Asp His Phe Phe Asp Leu Leu Thr Glu Ala
        105                 110                 115
Phe Pro Gln Leu Asn Gln Ala Phe Arg Thr Ala Leu Ser Thr Leu Val Arg
120                 125                 130                 135
Tyr Arg Lys Tyr Val Thr Asn Ala Ile Gln Met Pro Tyr Ser Asn Ser Lys
                140                 145                 150
Leu Glu Ala Ile Asn Lys Leu Ile Ser Phe Leu Gln Thr Gln Thr Cys Arg
        155                 160                 165                 170
Leu Cys Phe Ser Ser Asn Ser
                175
```

(2) INFORMATION FOR SEQ ID NO:17:

(i) SEQUENCE CHARACTERISTICS:
        (A) LENGTH: 18 bp
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO: 17:

GCCACTATCG ACTACGCG                                    18

(2) INFORMATION FOR SEQ ID NO:18:

(i) SEQUENCE CHARACTERISTICS:
        (A) LENGTH: 18 bp
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO: 18:

TCATTTGATA TGCCTCCG                                    18

(2) INFORMATION FOR SEQ ID NO:19:

(i) SEQUENCE CHARACTERISTICS:
        (A) LENGTH: 20 bp
        (B) TYPE: nucleic acid
        (C) STRANDEDNESS: single-stranded
        (D) TOPOLOGY: linear

```
    (ii) MOLECULE TYPE:
         (A) DESCRIPTION:  other nucleic acid (iii) HYPOTHETICAL:  no (iv) ANTI-SENSE:  no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO:    19:

GTGAGATAAA TAGTAGTGCG                                                    20

(2) INFORMATION FOR SEQ ID NO:20:

(i) SEQUENCE CHARACTERISTICS:
         (A) LENGTH:  20 bp
         (B) TYPE:  nucleic acid
         (C) STRANDEDNESS:  single-stranded
         (D) TOPOLOGY:  linear (ii) MOLECULE TYPE:
         (A) DESCRIPTION:  other nucleic acid (iii) HYPOTHETICAL:  no (iv) ANTI-SENSE:  no (v) FRAGMENT TYPE:

(vi) ORIGINAL SOURCE:

(vii) IMMEDIATE SOURCE:

(viii) POSITION IN GENOME:

(xi) SEQUENCE DESCRIPTION:SEQ ID NO:    20:

TCCAGCTCGT GTCATAATCT                                                    20
```

STREPTOCOCCUS PNEUMONIAE CAPSULAR POLYSACCHARIDE GENES AND FLANKING REGIONS

The present application is a continuation-in-part of U.S. patent application Ser. No. 08/243,546, filed May 16, 1994, now abandoned. The entire text and figures of which disclosure is specifically incorporated herein by reference without disclaimer.

The government owns certain rights in the present invention pursuant to grant is number AI28457 from the Public Health Service and T32 AI07041-13 from the National Institutes of Health.

BACKGROUND OF THE INVENTION

1. Field of the Invention

The present invention relates generally to the fields of bacterial capsule formation and the genes responsible for polysaccharide synthesis. More particularly, it concerns the genes and gene products that direct the formation of the *Streptococcus pneumoniae* serotype-specific polysaccharide capsule. The present invention also includes the identification of non-type specific gene sequences, flanking the capsule genes, and their use for the directed expression of specific serotypes of *S. pneumoniae* capsules.

2. Description of the Related Art

Infections due to *S. pneumoniae* are among the top ten causes of death in the United States. The normal populations most affected are young children and the elderly: pneumococcal pneumoniae, mainly affecting the elderly, causes >40,000 deaths per year among ~500,000 cases and represents 60 to 80% of all bacterial pneumoniae; pneumococcal meningitis, with ~4000 cases/year, represents 11% of the total meningitis cases and has a fatality rate of >30%—greater than twice that of the two other leading causes, *N. meningitidis* and *H. influenzae*; bacteremia, usually following pneumoniae or meningitis, accounts for >35,000 cases per year (>30% fatal); and otitis media, the most frequent reason for pediatric office visits after well-child care, is caused by *S. pneumoniae* in ~50% of cases (ACIP, 1981; ACIP, 1989; Austrian, 1984; Burke et al., 1971; Center for Disease Control, 1978; Johnston and Sell, 1964; Koch and Dennison, 1974).

Other populations have an even higher incidence of pneumococcal infections: approximately 30% of sickle cell children will have severe pneumococcal infections in the first three years of life and ~35% of those will die (Overturf, et al., 1977; Powars, et al., 1981; Powars, 1975); in both adults and children with HIV infections, *S. pneumoniae* is the major cause of invasive bacterial respiratory disease (Janoff et al., 1992). Patients with lymphomas, Hodgkins disease, multiple myeloma, splenectomy, and other debilitating diseases or immunologic deficiencies, are particularly susceptible to serious pneumococcal disease, as are those with chronic illnesses such as diabetes mellitus and heart disease. Furthermore, strains of *S. pneumoniae* are emerging that harbor resistances to multiple antibiotics, including penicillin (Appelbaum, 1992; Jacobs et al., 1978; Landesman et al., 1982).

The polysaccharide capsule of *S. pneumoniae* is the major virulence determinant of this organism. Despite early studies of the genetics, pathogenesis, and immunology of capsular polysaccharides, it remains unclear why certain capsular types appear to have a greater capacity to cause disease. Of the more than 80 known capsular serotypes, 23 account for more than 90% of all pneumococcal infections.

In children, the most prevalent types are 3, 6, 14, 19, and 23, (Gray and Dillon, 1986), whereas in adults types 1, 3, 4, 6, 7, 8, 9, 12, 14, 18, 19, 23 prevail (Finland and Barnes, 1977). In assays of opsonophagocytosis (Branconier and Odeberg, 1982; Giebink et al., 1977; Knecht et al., 1970), complement activation and deposition (Fine, 1975; Gordon et al., 1986; Hostetter, 1986; Stephens et al., 1977; Winkelstein et al., 1980; Winkelstein et al., 1976), and mouse virulence (Briles et al., 1992; Briles et al., 1986; Knecht et al., 1970; MacLeod, 1965; Walter et al ., 1941; Yother et al., 1982), levels of virulence have frequently been found to vary with the type of capsule expressed. For example, isolates expressing type 3, 4, and 19 capsules are highly resistant to phagocytosis, whereas those expressing types 6A, 14, 23 and 37 are significantly less resistant (Branconier and Odeberg, 1982; Hostetter, 1986; Knecht et al., 1970; Wood and Smith, 1949).

The importance of the capsule also results from the fact that anti-capsular antibodies are highly protective against infection. Nonetheless, the current polysaccharide-based vaccine is not particularly useful in some of the populations most affected by pneumococcal disease, e.g., the very young and the elderly, because of poor or absent immune response to polysaccharide antigens.

The ability to produce improved vaccines and therapies for pneumococcal infections will most likely be the result of a better understanding of the basic pathogenic mechanisms of the organism. This understanding necessarily includes the genetic basis for the expression of serotype-specific polysaccharides and the role of capsular type per se in pathogenesis.

Some 85 different serotypes of Streptococcus pneumoniae, differing in the structure of the polysaccharide produced, have been identified (van Dam et al., 1990). The basis for the emergence of new capsule types remains obscure. Whether influenced by mutation, recombination, or immune selection, genetic exchange of DNA is likely to have played a major role in the evolution of capsule types. It is known that pneumococcal capsule types can be changed through genetic transformation in vitro (Dawson, 1930; Dawson and Sia, 1931; Langvad-Nielson, 1944; Avery et al., 1944). Epidemiological studies suggest that a significant degree of genetic exchange occurs in vivo (Crain et al., 1990; Coffey et al., 1991; Versalovic et al., 1993). However, the mechanism by which capsule types are exchanged is not fully understood.

Extensive study was made of the genetics of capsular polysaccharide synthesis in *S. pneumoniae* using spontaneous mutants with defects in biosynthetic functions (Effrussi-Taylor, 1951; Ravin, 1960; Bernheimer and Wermundsen; 1972). The results of these studies indicated that the genes for polysaccharide synthesis were closely linked and could be transferred as a unit during genetic transformation. A cassette-type model of capsule type change based on this data has been proposed (Taylor, 1949; Austrian et al., 1959; Bernheimer and Wermundsen, 1972). According to the model, the type-specific genes for each capsule type would be present only in the genome of a strain of that capsule type and would show little homology to the type-specific genes of other capsule types. The type-specific genes would be located in homologous sites in the different chromosomes, clustered together between regions of highly homologous flanking DNA. During transformation, recombination would occur in the flanking regions, resulting in the replacement of the recipient's type-specific region by that of the donor.

The clustering of capsule biosynthetic genes proposed by the model is analogous to the organization that has been observed in the gram negative bacteria *Escherichia coli* (K antigens) (Roberts et al., 1988), *Neisseria meningitidis* (Frosch et al., 1989), and *Haemophilus influenzae* (Kroll et al., 1989). For each of these organisms, the type-specific region encoding biosynthetic functions (region 2) is flanked by highly homologous regions necessary for polysaccharide translocation (region 1) and modification (region 3). Since *H. influenzae*, like *S. pneumoniae*, is naturally transformable, it has been proposed that capsule type change in this pathogen may occur by transformation with the type-specific gene cluster from a different serotype (Zwahlen et al., 1989).

The one exception to the cassette model of capsule type change in *S. pneumoniae* is binary capsule formation. When non-encapsulated mutants have been transformed with chromosomal DNA from a strain of a different capsule type, most of the encapsulated transformants express the capsule type of the donor. However, at a frequency 10 to 100 times lower, encapsulated transformants are obtained which express both capsules (Bernheimer and Wermundsen, 1972). In some of these transformants, the second set of capsule genes is closely linked to the original set. However, these strains are unstable, and, at high frequency, lose the ability to produce the original capsule type. In binary strains in which the acquired capsule genes are unlinked to the original genes, binary capsule production is stable (Bernheimer and Wermundsen, 1969). Elucidation of the mechanism of binary capsule type formation may be the key to understanding novel capsule type creation in *S. pneumoniae*.

It is clear that a better understanding of the genetics of capsular polysaccharide synthesis in *Streptococcus pneumoniae* is needed. The identification of type-specific capsular genes and the ability to transfer them, singly or as a gene cassette, to desired recipients, will elucidate the role of capsular types in virulence and allow easy identification of *S. pneumoniae* serotype. This ability will improve existing methods of diagnosis, identifying not only the presence of *S. pneumoniae* but also the capsular type of the invading strain. Furthermore, it will allow construction of strains producing elevated levels of capsular polysaccharides for improved vaccines.

SUMMARY OF THE INVENTION
Capsular Polysaccharide Genes and Flanking Regions

The present invention arises out of the discovery and sequence characterization of a gene family that confers on *S. pneumoniae* the ability to produce type-specific capsules that define the serotype of the organism. The inventors refer to this gene family as the capsule synthesis or cps genes. These genes encode the various enzymatic functions of capsule synthesis and determine the particular structure of the capsule polysaccharide that is produced, and thereby define serotype. These genes, designated cpsB, cpsC, cpsE, cpsD, cpsS, cpsU, cpsM, tnpA, and plpA, map to specific DNA segments of sizes believed to range from about 0.5 kb to greater than 10 kb that appear to be type-specific for *S. pneumoniae*. Based upon the findings of the inventors, many type-specific genes may be distinguished on the basis of restriction fragment length polymorphism (RFLP) analysis.

The present invention also includes the discovery and sequence characterization of non-type specific DNA regions that flank both sides of the cps locus. These flanking DNA segments can be used to identify the location of cps flanking DNA from any strain of *S. pneumoniae*. This invention thus provides the ability to identify the cps locus within all strains and allows for the subsequent isolation and characterization of all genetic elements involved in determining *S. pneumoniae* serotype.

The classification of *S. pneumoniae* strains is based on serological analysis of cell surface structures. 85 distinct serotypes have been identified to date based on the formation of surface molecules. The formation of the cell surface of *S. pneumoniae*, and in particular its polysaccharide capsule, has, until now, eluded characterization at the molecular genetic level. However, studies of the biosthesis of the polysaccharide capsule have revealed that at least some of the genes are likely to include enzymes involved in the preparation of the sugar backbones for incorporation into the saccharide backbone, such as UDP-glucose dehydrogenase.

As mentioned above, these polymorphic "type-specific" sequence regions were found to be bounded or flanked by "non-type specific" regions having sequence elements that are apparently shared among the various subtypes. These regions, referred to as the left and right flanking regions, extend for, at least, 1 to 3 kb on either side of the cps genes. Thus, in type 3, the entire leath of the capsule synthesis genes, including the non-type specific flaking regions, and any DNA sequences in between, is greater than 9 kb. In other capsule types the length is on the order of about 5 to 20 kb, with the maximum length being related to the complexity of the polysaccharide encoded. Importantly, it is these flanking regions that allow recombination and integration of the type specific capsule genes to occur. Thus, when a selected cps gene or genes is positioned between the flanking regions, the resultant construct can be stably integrated into a *S. pneumoniae* host.

The present discoveries concerning the cps gene regions, the identification of conserved flanking regions, and the construction of erythromycin resistant insertions in adjacent, non-type specific DNA elements, allows for the changing of capsular serotypes by "cassetting-in" the biosynthetic genes for different serotypes. This methodology may be employed for generating high yield capsular polysaccharide producing strains of different (heterologous) serotypes. For a high yielding strain, the existing serotype biosynthetic genes may be deleted and a different serotype's genes inserted ("cassetted in"). These other serotypes may come from strains where their natural genetic background gives only poor or moderate levels of capsular production.

As used herein, the term "gene cassette" or simply "cassette", is intended to refer to any DNA segment flanked by one, or both, or part of, the cps flanking regions or a cps genetic element or DNA sequence which is found between the flanking regions.

Prior to the present invention, the foregoing underlying mechanism of genetic recombination of the capsule synthesis genes was unknown, as were the specific sequences involved. A principal contribution of the present inventors is the specific characterization of the individual genes and flanking regions, allowing for their manipulation and individual transfer to hosts. Now, discrete nucleic acid segments, or cassettes, containing a cps flanking region, gene or genes, can be readily prepared and easily used in transformation.

Hybridization Probes and Primers

Accordingly, in certain embodiments the invention concerns nucleic acid segments that hybridize with cps genes and/or flanking regions. The nucleic acid segments will generally be less than about 20 kb in length, and preferably less than about 15 kb in length, or even 10 kb, and will comprise a non-type specific *S. pneumoniae* cps gene flanking region, and/or a type-specific cps gene, of sufficient length to allow hybridization with a pneumococcal cps flanking region and/or gene. Nucleic acid segments that are capable of hybridizing with the 5' flanking region, the 3' flanking region, to both flanking regions, to one or more of the genes designated cpsB, cpsC, cpsE, cpsD, cpsS, cpsU, cpsM, tnpA and 'plpA, and to one or more genes in combination with one or more flanking regions, are encompassed by the invention.

Nucleic acid segments that include a first sequence portion capable of hybridizing to the 5' cps gene flanking region and a second sequence portion capable of hybridizing with the 3' cps gene flanking region form one aspect of the invention. Such nucleic acid segments may be combined with one or more cps genes and may be constructed to form a genetic unit in which the gene (or genes) is located between the two flanking regions. The gene(s) may be from a different cps serotype to the flanking regions or they may be from the same cps serotype to the flanking regions. Such genetic units may be termed cassettes and may also encompasses the form of a circular DNA segment, plasmid, cosmid, or phage. An isolated fragment of DNA containing DNA such as might be generated by restriction digestion, ligation, and/or PCR methodologies would also be included. The nucleic acid segment, or cassette, may also include other regions of DNA, such as restriction or cloning sites, PCR primers, promoters, antibiotic resistance genes, and the like, as necessary or desired to make a functional genetic unit.

In order to have utility in connection with the present invention, all that is required is that such a nucleic acid segment or genetic unit include a region of sufficient complementarity and size to allow selective cross-hybridization with the target flanking region or gene sequence.

In general, shorter and intermediate length nucleic acid fragments will be useful as hybridization probes and primers, and in particular, for use in PCR, where the primers will allow generation of the entire intervening cps sequence.

Thus flanking region and gene fragments on the order of at least about 14–15, 20, 30, 40, 50, or 100 to 200, contiguous complementary nucleotides are contemplated, although sequences of 500, 1,000, or more, nucleotides in length may also be used. The DNA segments may, of course, be of any length within the stated ranges. This is the meaning of "about" in this context, with "about" meaning a range longer or shorter than the stated length, extending to the previously quoted longer and shorter lengths (with about 14 or so still being the minimum length). The ranges thus encompass 1 to 4, 1 to 9, 1 to 49, 1 to 99, and the like, nucleotides in length.

Longer nucleic acid segments and fragments having on the order of up to 1,000, 2,000, 3,000, 5,000, 10,000, 15,000 or longer in length will also have particular utilities in addition to their function in hybridization embodiments. In particular, longer nucleic acid segments and fragments including selected cps coding sequences may be employed in the expression of recombinant proteins, and nucleic acid segments that include one or more cps gene sequences positioned between the flanking regions (cassette constructs) may be used in gene transfer embodiments as described above. The DNA segments may, of course, be of any length within the ranges stated above, so long as they function to achieve the desired effect. "About" in this context therefore indicates ranges of from 1 to 999, or 1 to 4,999, and the like, nucleotides longer or shorter than the stated length.

Nucleic Acid and Amino Acid Sequences

Exemplary flanking regions sequences, as disclosed herein, are set forth in SEQ ID NO:1, SEQ ID NO:2, SEQ ID NO:3, SEQ ID NO:4 and SEQ ID NO:6 (FIG. 7 and FIG. 8). The 5' cps gene flanking region is represented by SEQ ID NO:1, SEQ ID NO:2, SEQ ID NO:3 and SEQ ID NO:4. SEQ ID NO:1, SEQ ID NO:2 and SEQ ID NO:3 corresponds to regions of DNA sequenced in the upstream portion of the 5' flanking region and SEQ ID NO:4 corresponds to the downstream portion of the 5' flanking region and is termed the "repeat" region. DNA between SEQ ID NO: 1, SEQ ID NO:2, SEQ ID NO:3 and SEQ ID NO:4 are also part of the cps 5' flanking region. SEQ ID NO:1 is 300 nucleotides in length and corresponds to the last 180 nucleotides of cpsB and the 5' end of cpsC which begins immediately (FIG. 6A and FIG. 7). SEQ ID NO:2 is 261 nucleotides in length and corresponds to a 3' end region of cpsC (FIG. 6B and FIG. 7). SEQ ID NO:3 is 262 nucleotides in length and corresponds to part of cpsE and the 5' end of the repeat region (FIG. 6C and FIG. 7). SEQ ID NO:4 is 934 nucleotides in length, (nucleotide 1 through 934, FIG. 6D and FIG. 8). The 3' cps gene flanking region is 1307 nucleotides in length, 1 through 1307, SEQ ID NO:6 (nucleotide 5886 through 7192, FIG. 6I and FIG. 8).

The inventors have found that certain S. pneumoniae nucleotide sequences described in the scientific literature correspond to stretches of sequences from the flanking regions of the present invention. For example, Guidolin et al. (1994) have sequenced 6,322 base pairs of the 19F S. pneumoniae serotype cps locus. Sequence analysis indicated that this region contained six complete open reading frames and one partial, which they named cps19fA to cps19fG. Southern hybridization revealed that cps19fA and cps19fB were conserved in 12 other S. pneumoniae serotypes tested, including serotype 3. cps19fC and cps19fD also hybridized to Type 3 S. pneumoniae. The sequences for cpsB, cpsC and cpsE (SEQ ID NO:1, SEQ ID NO:2 and SEQ ID NO:3), as disclosed herein, are about 99% identical to cps19fB, cps19fC and cps19fD respectively (Guidolin et al. 1994). However, cpsE is truncated at the 3' end with respect to the 19F gene (lacks ~280 nt). The site of the truncation is adjacent to the region designated as the "repeat" sequence (SEQ ID NO:4). Based on blotting data (see Example 17) part of the repetitive element is in SEQ ID NO:3. This sequence extends 132 nt upstream of the SacI site at the start of SEQ ID NO:4, as shown in FIG. 7. Although Guidolin et al. (1994) have sequenced this area in serotype 19f, they do not identify this sequence as being a gene flanking region and do not suggest its use as part of an S. pneumoniae capsular cassette.

Garcia et al. (1993) localized a 781 bp EcoRV subfragment of a gene (cap3-1) that they proposed was involved in the transformation to a capsulated phenotype. The first 52 nucleotides of the 781 Garcia et al. sequence correspond to nucleotides 883 to 934 of SEQ ID NO:4. The next 443 nucleotides of the Garcia et al. sequence corresponds to nucleotides 1 to 443 of SEQ ID NO:5. However, the remaining 286 nucleotides of the 781 bp sequence do not show any homology with the instant sequences. As with the above, this article does not identify this sequence as being a gene flanking region and do not suggest its use as part of an S. pneumoniae capsular cassette. However, the same group (Arrecubieta et al., 1994) using probes in Southern blotting, identified the upstream region of their cap3A as a sequence common to all pneumoniae strains tested.

The amino acid sequences described by Garcia et al. (1993) include a putative protein of 138 amino acids (CAP3-1), transcribed in the same direction as CpsD, and another truncated open reading frame, transcribed in the opposite direction. The first 117 amino acid residues of CAP3-1 corresponds to the first 117 residues of CpsD (SEQ ID NO:11). CAP3-1 is reportedly similar to the amino-terminus of GDP-mannose dehydrogenase of Pseudomonas aerugi-

*nosa.* The remaining 21 residues of CAP3-1 described by Garcia et al. (1993) have no homology with the remaining 277 amino acid residues of CpsD, suggesting that Garcia et al. had cloned a truncated gene in which the 5' end of the cpsD gene was aberrantly fused to an unidentified DNA sequence.

Pearce et al. (1994) described an *S. pneumoniae* protein and corresponding nucleotide sequence, that they proposed was a permease-like protein involved in peptide transport. They termed this protein PlpA. Nucleotides 484 to 1307 of SEQ ID NO:6 correspond to nucleotides 843 to 1672 of the plpA described by Pearce et al. (1994), and the amino acid SEQ ID NO:15 corresponds to residues 282 to 557 of their PlpA. Previously, Pearce et al. (1993) had described an *S. pneumoniae* protein they called Exp1. The amino acid sequence of Exp1 corresponds to residues 49 through 209 of SEQ ID NO:15. The inventors have found that the 'plpA located adjacent to the type 3-specific genes lacks about one third of its 5' end when compared to plpA genes located adjacent of the capsule genes of other types such as that used by Pearce et al. (1994). Neither Pearce et al. (1994) nor Pearce et al. (1993) identify this sequence as being involved in capsule synthesis in any way, nor do they suggest that it forms part of a common DNA flanking region.

Although certain stretches of nucleotide sequences may have been known in the art, their function, relationship to capsule synthesis and, particularly, their role as interchangeable flanking regions has not previously been described. An important feature of the invention is that the functional characterization of the flanking regions allows, for the first time, for the exchange of *S. pneumoniae* type-specific capsule genes to be manipulated and controlled. This is only possible in light of the inventors discovery of the conserved cps gene flanking regions. Nucleic acid segments, including cassettes and plasmids, that include both 5' flanking region sequences and 3' flanking region sequences are thus one preferred embodiment of the invention. PCR primers that have sequences corresponding to both flanking regions form another preferred embodiment of the invention.

Encoded within the upstream 5' flanking region (SEQ ID NO:1, SEQ ID NO:2 and SEQ ID NO:3) are the partially sequenced genes cpsB, cpsC and cpsE which encode for CpsB (SEQ ID NO:7), CpsC (SEQ ID NO:8 and SEQ ID NO:9) and CpsE (SEQ ID NO:10) (FIG. 6A, FIG. 6B, FIG. 6C and FIG. 7).

The invention also includes other cps gene sequences, either alone or in combination with the flanking region sequences described above. The type-specific portions of the polycistronic cps gene locus operon, as disclosed herein, are encompassed within nucleotides 1 through 4951, SEQ ID NO:5 (nucleotides 935 through 5885, FIG. 6E, FIG. 6F, FIG. 6G, FIG. 6H, FIG. 7 and FIG. 8). Beside the open reading frames for the proteins, the sequences also contain putative promoters that direct the transcription of the genes of the cps locus. Other promoters, herein termed "recombinant promoters", may also be used to direct the expression of the cps genes in accordance with the invention.

The genes encoded within SEQ ID NO:5 and as disclosed herein, include cpsD, cpsS, cpsU, cpsM and part of tnpA.

cpsD is 1277 nucleotides in length, 1 through 1277 of SEQ ID NO:5 (935 through 2211, FIG. 6E and FIG. 8).

cpsS is 1267 nucleotides in length, 1277 through 2543 of SEQ ID NO:5 (2211 through 3477, FIG. 6F and FIG. 8).

cpsU is 1055 nucleotides in length, 2707 through 3761 of SEQ ID NO:5 (3641 through 4695, FIG. 6G and FIG. 8).

cpsM is 1194 nucleotides in length, 3758 through 4951 of SEQ ID NO:5 (4692 through 5885, FIG. 6H and FIG. 8).

CpsS is just downstream of CpsD, only 15 nucleotides separate a potential start codon for CpsS from the stop codon of CpsD. Other start codons for CpsS are at nucleotides 1311 and 1355 (SEQ ID NO:5). There is a large non-coding region between cpsS and cpsU (nucleotide 2543 through 2707, SEQ ID NO:5). Where as cpsD and cpsS overlap by one nucleotide and cpsU and cpsM overlap by 4 nucleotides. All four genes are transcribed in the same direction and cpsD and cpsS are in the same reading frame.

Encoded within the 3' flanking region (SEQ ID NO:6) is the truncated sequence for plpA, designated 'plpA, which is 823 nucleotides in length, 484 through 1307 of SEQ ID NO:6 (nucleotides 6370 through 7192, FIG. 6I and FIG. 8). As mentioned above the 5' end is not present in the plpA gene of type 3 *S. pneumoniae*. A partial transposase sequence, tnpA, is contained between cpsM and 'plpA. It is transcribed in the opposite orientation to all other genes described herein, and extends from nucleotide 480 through 1, SEQ ID NO:6 to overlap with the cpsM gene nucleotide 4951 through 4902, SEQ ID NO:5 a total of 531 nucleotides (nucleotides 5836 through 6366, FIG. 6J and FIG. 8).

cpsD encodes a 394 amino acid sequence (SEQ ID NO:11) which is homologous to that of the UDP-glucose dehydrogenase (HasB) from *Streptococcus pyogenes*. The deduced amino acid sequence encoded by cpsS predicts a protein of 416 residues (SEQ ID NO:12) which is homologous to polysaccharide synthases. cpsU encodes a 306 amino acid sequence (SEQ ID NO:13) which is homologous to glucose-1-phosphate uridylyltransferases from several other bacterial species. cpsM encodes a 397 amino acid sequence (SEQ ID NO:14) which has homology with phosphoglucomutases from several bacterial species. However, it lacks approximately 25% of the C-terminal present in other phosphomutases and may not encode a functional protein. 'plpA encodes a 274 amino acid sequence (SEQ ID NO:15) and tnpA encodes a 177 amino acid sequence (SEQ ID NO:16).

Thus, in certain particular embodiments the present invention concerns the individual cps genes, including segments encoding sequences corresponding to one or more of the cpsB, cpsC, cpsE, cpsD, cpsS, cpsU and cpsM genes. tnpA and plpA gene constructs, when combined with other cps genes and flanking regions, are also encompassed by the invention. In further embodiments, the invention concerns the respective proteins and polypeptides encoded by the cpsB, cpsC, cpsE, cpsD, cpsS, cpsU, cpsM, tnpA and plpA genes. The proteins, polypeptides and peptides of the invention may be used in a variety of embodiments, including, e.g., in immunological protocols to generate antibodies that may, in turn, be used in diagnostic embodiments to detect *S. pneumoniae*.

It should be noted that in the definition of the genes and proteins, the term "cps" is not used to indicate that the gene or protein concerned has a defined role in capsule synthesis in all cases. Rather, it indicates that the gene is located between the cps gene flanking regions, i.e., within the cps operon, and in eclose association with other cps genes. It should also be noted that, the "*S. pneumoniae* gene region" refers to all genetic elements associated with the cps genes, including genes incorporated within the flanking regions. A "genetic element" refers to any DNA that may encode for a protein or polypeptide, regardless of functionality. The utility of the cps genes remains that, e.g., they may be used in the same diagnostic manner to identify *S. pneumoniae*.

While the present disclosure is exemplified in part through the cloning and sequencing of type 3 cps genes, the techniques are equally applicable to the cps genes of other capsule serotypes, including any one of the 85 serotypes. For example, using the techniques developed for the characterization of the type 3 cps gene region, the inventors have proceeded to characterize the restriction maps for the type 2 type 6B strains (Example 16, FIG. 11). As expected, the maps of the non-type specific flanking regions were found to be identical from serotype to serotype, whereas the maps for the cps gene regions themselves were serotype specific.

Diagnostic Embodiments

The cps flanking region and gene sequences, and the encoded proteins, may be employed in diagnostic embodiments. For example, the amount of S. pneumoniae, or S. pneumoniae serotype, present within a biological sample, such as blood, serum or a swab from nose, ear or throat, may be determined by means of a molecular biological assay to determine the level of nucleic acid complementary to the cps loci, or even by means of an immunoassay to determine the level of one of the polypeptides encoded by a gene from this locus. The cps locus DNA segment used in molecular biological assays may include the non-type specific segments such as the 5' and 3' flanking regions, SEQ ID NO:1, SEQ ID NO:2, SEQ ID NO:3, SEQ ID NO:4, SEQ ID NO:6 and any sequence in between, or the region encoding various polypeptides, such as those incorporated within SEQ ID NO:1, SEQ ID NO:2, SEQ ID NO:3, ID NO:5 and SEQ ID NO:6.

In a molecular biological method for detecting S. pneumoniae, one would obtain nucleic acids from a suitable sample and analyze the nucleic acids to identify a specific nucleic acid segment complementary to the cps loci (whether type- or non-type-specific). The nucleic acid segment will generally be identified by sequence, which method generally includes either; identifying a transcript with a corresponding or complementary sequence, e.g., by Northern or Southern blotting using an appropriate probe or; identifying a transcript with two or more shorter primers and amplifying with PCR technology.

Blotting Techniques

To detect S. pneumoniae, as may be used to identify a patient with otitis media, pneumococcal pneumonia or pneumococcal meningitis, using a method based upon hybridization and blotting techniques, one may use a probe with a sequence as set forth in SEQ ID NO:1, SEQ ID NO:2, SEQ ID NO:3, SEQ ID NO:4, SEQ ID NO:5 or SEQ ID NO:6, including any sequence in between, or an equivalent thereof. This imparts an evident utility to the nucleic acid segments of the present invention.

To conduct such a diagnostic method, one would generally obtain sample nucleic acids from the sample and contact the sample nucleic acids with a nucleic acid segment corresponding to the cps loci disclosed herein, under conditions effective to allow hybridization of substantially complementary nucleic acids, and then detect the presence of any hybridized substantially complementary nucleic acid complexes that formed.

The presence of a substantially complementary nucleic acid sequence in a sample, or a significantly increased level of such a sequence, in comparison to the levels in a normal or "control" sample, will thus be indicative of a sample that harbors S. pneumoniae. Here, substantially complementary nucleic acid sequences are those that have relatively little sequence divergence and that are capable of hybridizing to the sequences disclosed herein under standard conditions.

Where a substantially complementary nucleic acid sequence, or a significantly increased level thereof, is detected in a clinical sample from a patient suspected of having otitis media, pneumococcal pneumonia or pneumococcal meningitis, for example, this will be indicative of a patient that does have that particular disease. As used herein, the term "increased levels" is used to describe a significant increase in the amount of the cps loci nucleic acids detected in a given sample in comparison to that observed in a control sample, e.g., an equivalent sample from a normal healthy subject.

A variety of hybridization techniques and systems are known that can be used in connection with the S. pneumoniae detection aspects of the invention, including diagnostic assays such as those described in Falkow et al., U.S. Pat. No. 4,358,535.

In general, the "detection" of a cps locus is accomplished by attaching or incorporating a detectable label into the nucleic acid segment used as a probe and "contacting" a sample with the labeled probe. In such processes, an effective amount of a nucleic acid segment that comprises a detectable label (a probe), is brought into direct juxtaposition with a composition containing target nucleic acids. Hybridized nucleic acid complexes may then be identified by detecting the presence of the label, for example, by detecting a radio, enzymatic, fluorescent, or even chemiluminescent label.

Where one simply desires to distinguish S. pneumoniae DNA from the DNA of other bacteria, it is contemplated that the non-type specific region sequences may be employed as probes. However, where one desires to distinguish among different S. pneumoniae serotypes, it is contemplated that probes will include both type specific and non-type specific cps sequences. The type-specific sequences, being type specific, will selectively hybridize only to corresponding serotypes. Thus one can envision a battery of serotype specific cps nucleic acid hybridization probes can be employed to distinguish and identify serotype DNA samples. In these instances, it is not believed to be necessary to employ restriction enzyme digestion prior to hybridization, but this can be employed where desired. Alternatively, only one non-type specific sequences may be employed as a "universal probe" that allows detection of restriction fragment length polymorphisms (RFLPs). Typically for RFLP detection, one will employ the more specific hybridization technique of Southern analysis wherein restriction digestion of the unknown or target DNA is carried out using an enzyme that will cleave either within or surrounding the cps gene region (FIG. 4 and FIG. 11) show restriction maps for several of the serotype cps gene regions).

Many suitable variations of hybridization technology are available for use in the detection of nucleic acids, as will be known to those of skill in the art. These include, for example, in situ hybridization, Southern blotting and Northern blotting. In situ hybridization describes the techniques wherein the target nucleic acids contacted with the probe sequences are those located within one or more cells, such as cells within a clinical sample or even cells grown in tissue culture. As is well known in the art, the cells are prepared for hybridization by fixation, e.g. chemical fixation, and placed in conditions that allow for the hybridization of a detectable probe with nucleic acids located within the fixed cell.

Alternatively, target nucleic acids may be separated from a cell or clinical sample prior to contact with a probe. Any of the wide variety of methods for isolating target nucleic acids may be employed, such as cesium chloride gradient centrifugation, chromatography (e.g., ion, affinity, magnetic), phenol extraction and the like. Most often, the isolated nucleic acids will be separated, e.g., by size, using electrophoretic separation, followed by immobilization onto a solid matrix, prior to contact with the labelled probe. These prior separation techniques are frequently employed in the art and are generally encompassed by the terms "Southern blotting" and "Northern blotting". Although the execution of various techniques using labeled probes to detect cps locus DNA or RNA sequences in clinical samples are well known to those of skill in the art, a particularly preferred method is described in detail herein, in Example 4.

PCR Techniques

To detect S. pneumoniae, using a method based upon PCR technology of U.S. Pat. No. 4,603,102 (incorporated herein by reference), one may also use one or more probes with a sequence as set forth in SEQ ID NO:1, SEQ ID NO:2, SEQ ID NO:3 and SEQ ID NO:4 (including sequence in between), SEQ ID NO:5 or SEQ ID NO:6, or an equivalent thereof.

To conduct such a diagnostic method, one would generally obtain sample nucleic acids from a suitable source and contact the sample nucleic acids with two probes or primers corresponding to the cps loci disclosed herein, under conditions which allow for hybridization and polymerization to occur. A pair of probes, one corresponding to the 5' flanking region and the other corresponding to the 3' flanking region, would be sufficient to detect the presence of S. pneumoniae in a sample and may even be used to indicate the amount of bacteria present. Furthermore the size of the isolated PCR product, when separated by any of the methods as described above, may be sufficient to identify the S. pneumoniae serotype. Alternatively the PCR product may be digested with one or more restriction enzymes, which would enable individual serotypes to be distinguished, using the same principle as RFLP.

In further embodiments, it may be desired to employ other probes corresponding to type specific or non-type specific regions. A battery of serotype specific probes, probes corresponding to type specific DNA regions, may be employed in individual reactions, with a universal probe, a probe corresponding to non-type specific regions. The size of PCR products, with or without prior digestion with restriction enzymes, would distinguish and identify the S. pneumoniae serotype.

Kits

Kits for use in Southern and Northern blotting or PCR technology, to identify S. pneumoniae and/or individuals having, or at risk for developing, otitis media, pneumococcal pneumoniae or pneumococcal meningitis, are also contemplated to fall within the scope of the present invention. Such kits will comprise, in suitable container means, cps nucleic acid probes; also, generally, unrelated probes for use as controls; and optionally, one or more restriction enzymes.

Characterization of Streptococcus pneumoniae Serotypes

In another embodiment of the invention, the non-type specific DNA may be used, to isolate and characterize the type-specific DNA sequence for all or any strain of S. pneumoniae. Consequently, the most suitable probes for diagnosing S. pneumoniae infection, for use in any molecular biological technique, could be found.

The present invention identifies the common flanking DNA which may be used in hybridizations to target the location of the type-specific cps genes for any strain of S. pneumoniae. Once this location has been identified the cps genes may then be isolated and characterized by the use of conventional techniques, such as; chromosome crawling, PCR technology, cloning and DNA sequencing, all are disclosed herein. As mentioned above, this in turn would enable suitable probes from each S. pneumoniae strain to be chosen and then used for, diagnostic and research purposes.

Furthermore, the genetic elements involved in determining S. pneumoniae serotype may be elucidated, and an understanding of their effect on virulence and evolutionary role may be achieved.

In still more particular embodiments, the invention concerns the preparation and cloning of entire cps gene regions encoding one or more specific cps genes of a particular serotype, positioned within a "cassette" for ease of manipulation, e.g. in plasmid preparation or host cell introduction, etc. Thus, cps gene cassettes in accordance with the present invention will typically include left and right hand flanking regions to allow homologous recombination in S. pneumoniae host cells.

A preferred method for preparing cps gene cassette is through the application of PCR technology wherein left and right hand primer corresponding to left and right hand flanking region are employed to amplify the cps gene coding regions. Of course, the primers employed will typically include at their termini appropriate restriction enzyme site. Thus, the resulting cassette will preferably include at each terminus a restriction enzyme site of choice. The site, of course, will depend upon the vector that is ultimately employed for manipulation or transformation but may be the specific cleavage site for one or more of the restriction enzymes shown in FIG. 4 and FIG. 7 or listed in Table 1. The list is, of course, exemplary, and any restriction enzyme could be employed, as is well known to those of skill in the art.

The present invention also contemplates more traditional approaches to cps gene regions cloning, such as by partial fragmentation of S. pneumoniae DNA followed by cloning into a recombinant cloning host, such as E. coli, and screening by hybridization and antibiotic selection (using a selection marker found on the plasmid or other vector employed for cloning). Of course, if the cloning host is not a S. pneumoniae host, one may employ either type specific or non-type specific cps gene sequences for screening. In these cases, cassettes that are developed may include enzyme restriction sites naturally found to occur in the flanking regions, such as an SphI site.

It is contemplated that virtually any type of host cell may be employed in connection with the present invention, depending on the particular application. For example, where one simply desires to manipulate cps gene sequences, any acceptable host may be employed, such as an E. coli, or even an appropriate eukaryotic host where desired. However, where one contemplated producing capsule polysaccharides, one will desire to employ a gram positive host such as bacillus, staphylococcus or streptococcal hosts. Particularly preferred will be S. pneumoniae host, in that it is contemplated that such hosts will be more readily amenable to manipulation to increase capsular polysaccharide production.

The inventors contemplate that a particular application, therefore, will be the use of recombinant hosts not only for the preparation and manipulation of cps gene sequences, but also in the large scale production of capsule saccharides and polysaccharides. These polysaccharides are useful for the production of antigenic haptens and epitopes for use in the production of immunogens. Haptens and epitopes are described herein as portions of a molecule against which an immune response is directed. In conjunction with an molecule that elicits an immune response, that is an immunogen, an hapten-immunogen complex is able to elicit an immune response.

Generally speaking, where capsule production is required, one will employ a S. pneumoniae host cell into which a selected cps gene region is introduced or "cassetted in". First, a DNA segment that includes the selected *S. pneumoniae* cps gene(s) flanked by sufficient *S. pneumoniae* flanking regions to allow homologous recombination in the *S. pneumoniae* host is identified. It is contemplated that flanking regions on the order of 0.1 to 1 kb will be sufficient to allow recombination to occur. Once an appropriate DNA segment is introduced into the *S. pneumoniae* host, either as genomic DNA or as a recombinant vector (plasmid), transformed host expressing the introduced cps gene are selected.

DNA may be introduced into a suitable host by a variety of mechanisms, including natural transformation of *S. pneumoniae*, calcium mediated transformation or electroporation of *E. coli*. A particularly preferred method of bacterial transformation includes the steps of making an *S. pneumoniae* competent for transformation by growth in Todd Hewitt broth supplemented with calcium and bovine serum albumin. Alternatively electroporation may be employed, one makes the bacterial cells, such as the *E. coli* strain LE392, competent in 10% glycerol in water, adds the DNA, and electroporates the cells.

Where the cps gene DNA segment is introduced in the form of a plasmid, it would be preferable, at certain times, to employ a plasmid that is free of a *S. pneumoniae* origin of replication. Thus, virtually any traditional plasmid (which are designed, e.g. for gram negative hosts such as *E. coli*) may be employed. The reason is that where the plasmid is free of a *S. pneumoniae* origin of replication only those clones that have successfully undergone homologous recombination with the recombinant cps gene region will be detected. Stated another way, in this case, there is no requirement of a *S. pneumoniae* origin of replication in order for homologous recombination to occur, and thus homologous recombinants are inherently selected for using such a cloning technique.

Alternatively it may be simpler to introduce the cassette into *S. pneumoniae* on a replicating plasmid with a *S. pneumoniae* origin of replication. In this way, higher levels of polysaccharide production as a result of the elevated copy number of the plasmid (10 to 20) as opposed to the low copy number of the chromosome (1 to 2) would be achieved and homologous recombination need not occur.

Additionally, it is contemplated that there will be some advantage to employing as the starting host a *S. pneumoniae* strain that is a high producer of its own inherent cps gene. These high producers will necessarily include the genetic environment to support high production of the newly introduced cps complex, and thus will likely be ideal hosts for such production. To achieve such recombinants, all that is required is that the heterologous gene containing the flanking regions, or a genome containing the flanking regions, is introduced into the host cell, and resultant recombinants wherein the homologous gene has been replaced is selected.

Although the invention contemplates in particular embodiments the introduction of an entire recombinant cps gene region where capsule saccharide synthesis is desired, the invention also contemplates the introduction of one, two, three or so of the individual cps genes. It is contemplated that one or two genes, such as those that control the biosynthesis of sugar precursors may be sufficient to, in and of themselves, confer serotype specific saccharides production on the selected host, or can in of themselves, upregulate capsule production by existing cps genes of the host.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 6A. DNA sequence of the 5' flanking region including partial sequence of cps3B and cps3C (SEQ ID NO:1) encoding for SEQ ID NO:7 and SEQ ID NO:8.

FIG. 6B. DNA sequence of the 5' flanking region including partial sequence of cps3C (SEQ ID NO:2), encoding for SEQ ID NO:9.

FIG. 6C. DNA sequence of the 5' flanking region including partial sequence of cps3E (SEQ ID NO:3), encoding for SEQ ID NO:10.

FIG. 6D. DNA sequence of the "repeat" upstream flanking DNA (SEQ ID NO:4).

FIG. 6E. DNA sequence of the region containing cps3D (nucleotides 1 through 1277, SEQ ID NO:5). The −35 and −10 hexamers of potential σ−70 type promoters upstream of cps3D are underlined and labeled above the sequence. Putative ribosome binding sites are underlined. The precise locations of endpoints of insertion mutations shown in FIG. 7 are indicated by triangles below the sequence and are labeled with the name of the strain containing the given mutation. The locations of spontaneous mutations in cps3D are labeled with the sequence of the mutation and the name of the strain containing the mutation. The sequence from the PvuII-SspI fragment of A66R2 began at nucleotide 1921, thus it is possible that additional mutations are present from the PvuII site to this point. Selected restriction sites are shown.

FIG. 6F. DNA sequence of the region containing cps3S (nucleotides 1277 through 2543, SEQ ID NO:5). The precise locations of endpoints of insertion mutations shown in FIG. 7 are indicated by triangles below the sequence and are labeled with the name of the strain containing the given mutation.

FIG. 6G. DNA sequence of the region containing cps3U (nucleotides 2707 through 3806, SEQ ID NO:5). The −35 and −10 hexamers of potential σ−70 type promoters upstream of cps3U are underlined and labeled above the sequence. A short region of dyad symmetry just upstream of cps3U is overlined. Putative ribosome binding sites are underlined. The precise locations of endpoints of insertion mutations shown in FIG. 7 are indicated by triangles below the sequence and are labeled with the name of the strain containing the given mutation. Selected restriction sites are shown.

FIG. 6H. DNA sequence of the region containing cps3M (3746 through 4951, SEQ ID NO:5) with corresponding amino acid sequences. Note that the first line of FIG. 6H overlaps the last line of FIG. 6G.

FIG. 6I. DNA sequence of the region containing the 3' flanking region including 'plpA (SEQ ID NO:6) with corresponding amino acid sequences (SEQ ID NO:15).

FIG. 6J. The DNA sequence for a partial transposase A, tnpA, located between 'plpA and overlapping cpsM. The open reading frame is in the opposite orientation starting at nucleotide 6366 through 5836 of FIG. 6I.

DETAILED DESCRIPTION OF THE PREFERRED EMBODIMENTS

The present inventors have determined a genetic and physical map that encompasses the region responsible for the synthesis of the polysaccharide capsule of *S. pneumoniae*. The polysaccharide capsule of *S. pneumoniae* is a potent defense against the immune response of the host organism and is directly involved in bacterial virulence. The capsule locus, cps, is basically composed of two functional regions: a central region that contains the genes responsible for capsular biosynthesis and is described herein as the type-specific region, and the non-type specific regions that flank the central biosynthetic type-specific region.

*S. pneumoniae* has evolved a complex 'antigenic shift' mechanism that allows the bacteria to evade the host immune system. The antigenic shift of *S. pneumoniae* occurs via homologous recombination of a type-specific cassette that is replaced through natural transformation. *S. pneumoniae* is naturally competent allowing for the acquisition of chromosomal DNA from exogenous sources, such as other *S. pneumoniae*. Disclosed herein is evidence identifying the non-type specific regions as being responsible for providing the sequence identity that allows for homologous recombination cross-over points.

Figure 7:
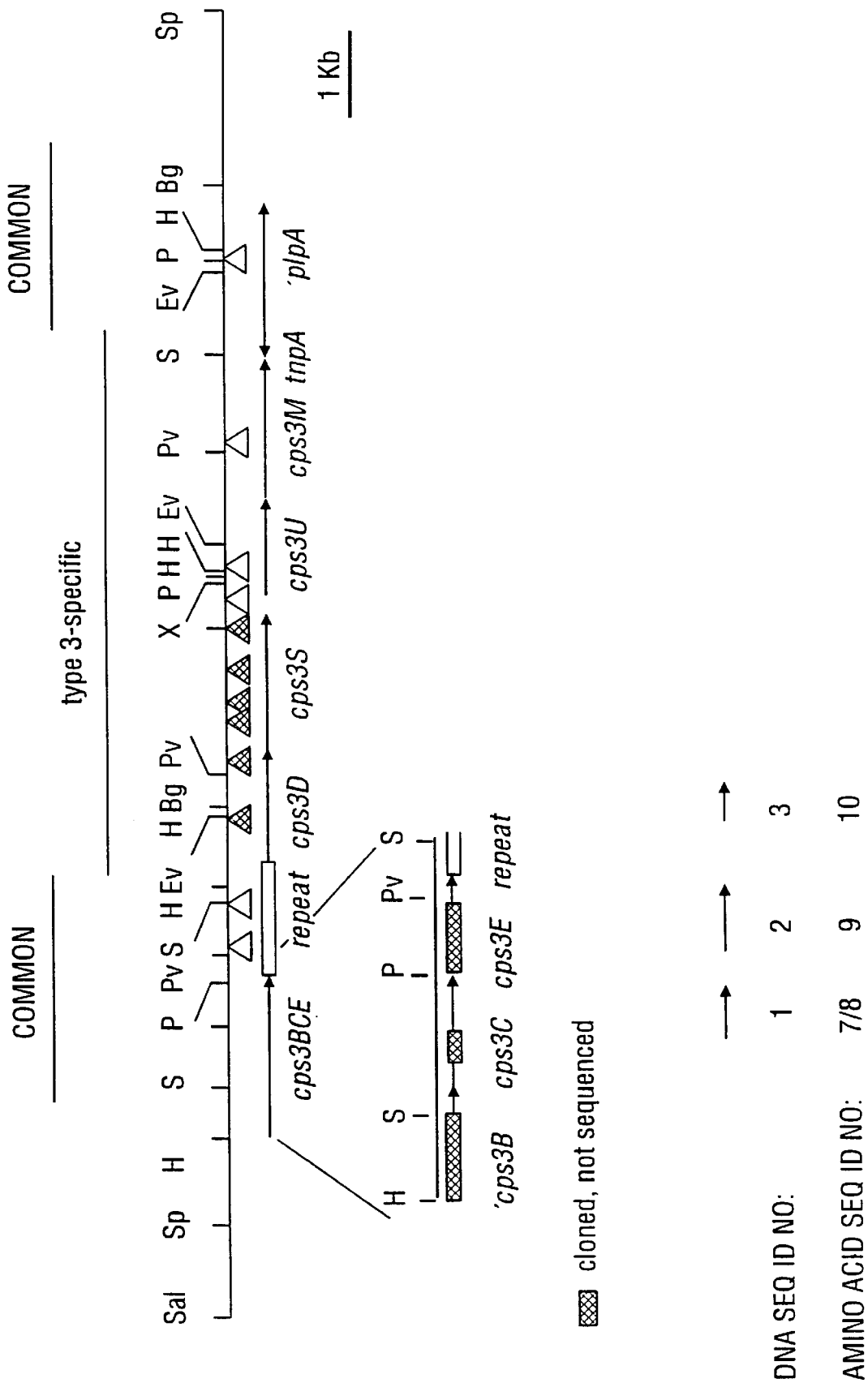
FIG. 7. Map of the chromosomal region involved in the biosynthesis of S. pneumoniae type 3 capsular polysaccharide. Triangles indicate the endpoints of insertion mutations. Filled triangles represent insertions which resulted in loss of capsule production. Open triangles represent mutations which did not result in loss of capsule production. Restriction enzyme sites are: Bg, BglII; Ev, EcoRV; H, HindIII; P, PstI; Pv, PvuII; S, SacI; Sa, SalI; Sp, SphI. Also included is a diagram showing the position of SEQ ID NO:1, SEQ ID NO:2 and SEQ ID NO:3, including the corresponding amino acid sequences SEQ ID NO:7, SEQ ID NO:8, SEQ ID NO:9 and SEQ ID NO:10.
Figure 8:
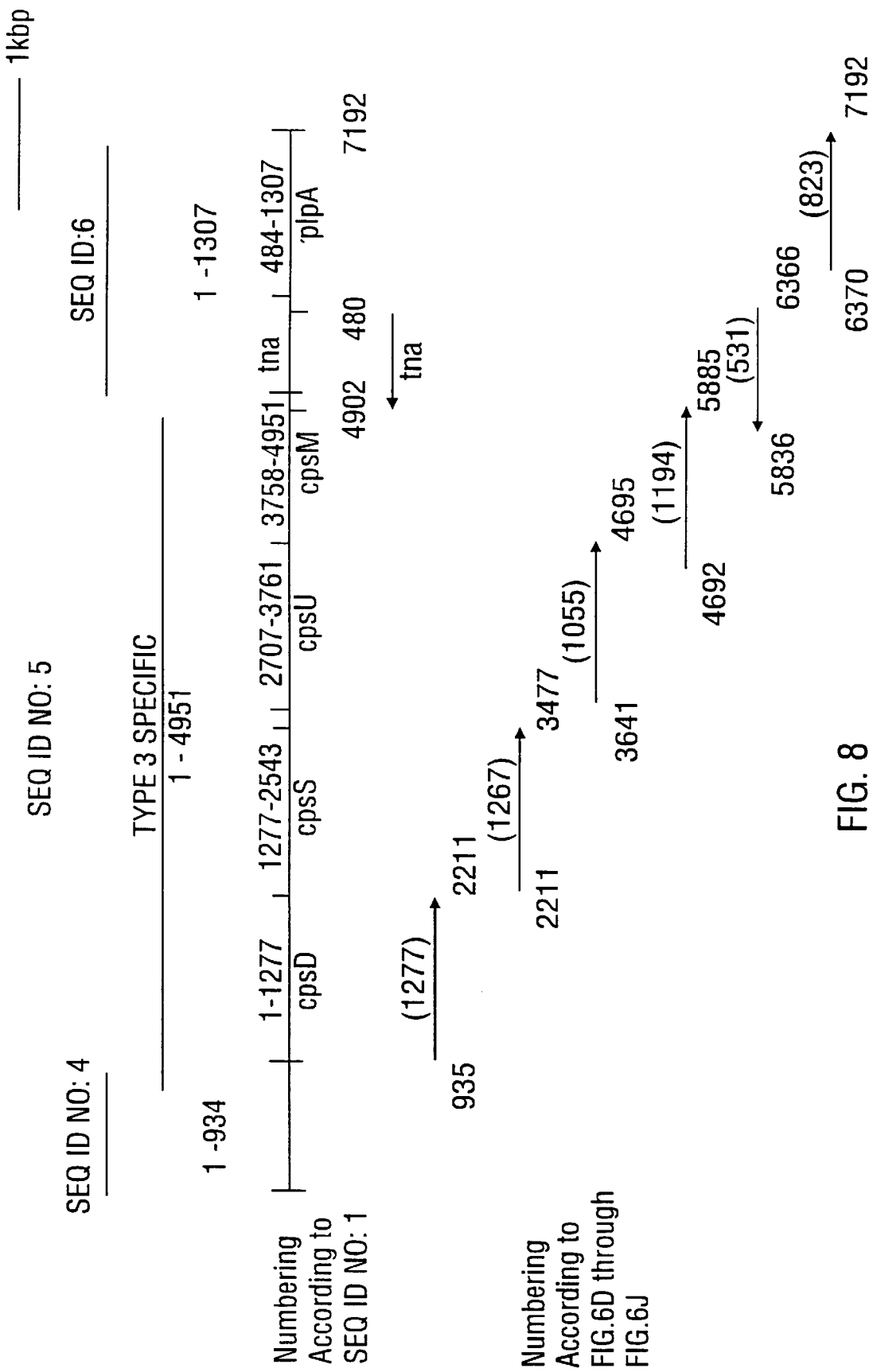
FIG. 8. Map of the chromosomal region involved in the biosynthesis of S. pneumoniae type 3 capsular polysaccharide showing the relationship between SEQ ID NO:4, SEQ ID NO:5 and SEQ ID NO:6, and DNA sequence as described in FIG. 6D through FIG. 6J.

The present inventors have identified and cloned the region of the *S. pneumoniae* chromosome that contains genes involved in the production of type 3 capsular polysaccharide, and that is specific to type 3 strains. They have also cloned approximately. 1–3 kb of DNA flanking both sides of this region and found it to be common to all capsular serotypes examined. A genetic and physical map of the region is presented in FIG. 6A, FIG. 6B, FIG. 6C, FIG. 6D, FIG. 6E, FIG. 6F, FIG. 6G, FIG. 6H, FIG. 6I, and FIG. 6J. A simplified version of which is shown in FIG. 7 and FIG. 8. The sites of insertion mutations made within the region are shown in FIG. 7. The regions found by hybridization studies to be specific to type 3 or common to all capsule types are also indicated in FIG. 7. The cloning of the upstream region, creation of insertion mutations, sequence analysis of the region, hybridization analyses using the upstream region, and an in vitro assay of type 3 capsule polymerization are described in the following examples.

The DNA sequence of the region containing the nine genes; cps3B, cps3C, cps3E, cps3D, cps3S, cps3U, cps3M, 'plpA, tnpA and the flanking DNA was determined and is presented in FIG. 6A, FIG. 6B, FIG. 6C, FIG. 6D, FIG. 6D, FIG. 6E, FIG. 6F, FIG. 6G, FIG. 6H, FIG. 6I, and FIG. 6J (SEQ ID NO:1, SEQ ID NO:2, SEQ ID NO:3, SEQ ID NO:5 and SEQ ID NO:6) along with the deduced amino acid sequences (SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 and SEQ ID NO:16).

Based on genetic, molecular, and biochemical data the inventors have been able to assign putative functions to the type-specific genes in the pathway for type 3 capsular polysaccharide biosynthesis. Two of the genes, cps3D and cps3S, are required for capsule synthesis. There is substantial evidence to indicate that cps3D encodes UDP-glucose dehydrogenase. Described herein is genetic evidence to indicate that several mutations causing the capsule-negative phenotype are located in the gene for UDP-glucose dehydrogenase. The predicted amino acid sequence has characteristics consistent with this function. Cps3D shows a high degree of homology to HasB, which is the UDP-glucose dehydrogenase of *S. pyogenes* (Dougherty & van de Rijn, 1993). Within Cps3D are sequences homologous to the active site and the NAD-binding site in known UDP-glucose dehydrogenases. It is not possible to perform the standard UDP-glucose dehydrogenase assay on extracts of *S. pneumoniae* due to the presence of a NADH oxidase, which copurifies with the enzyme (Smith, et al., 1960; Smith, et al., 1958). However, extracts from cps3D mutants could synthesize type 3 capsule in vitro if supplied with UDP-glucuronic acid, i.e., they lacked the ability to convert UDP-glucose to UDP-glucuronic acid and thus lack UDP-glucose dehydrogenase activity.

Cps3S is a new member of a family of polysaccharide synthases. All of these polysaccharide synthases for which the structures of the polysaccharides are known produce β (1–4) linked polysaccharides. Thus, it is possible that Cps3S forms the β (1–4) linkage in the disaccharide cellobiuronic acid (glcAβ (1–4) glc), and that a second enzyme is required to polymerize (i.e., create the β (1–3) linkages) the disaccharides into the full length polysaccharide. However, HasA, the enzyme most closely related to Cps3S, creates both linkages, a β (1–4) and a β (1–3), in the production of hyaluronic acid capsule (DeAngelis, et al., 1993). HasA has recently been shown to be sufficient for hyaluronic acid synthesis in heterologous bacteria, given the nucleotide sugar substituents (DeAngelis, et al., 1993a). Because the inventors did not find another required enzyme in the type 3-specific region, Cps3S, like HasA, may synthesize the polysaccharide by monomer addition.

Figure 10:
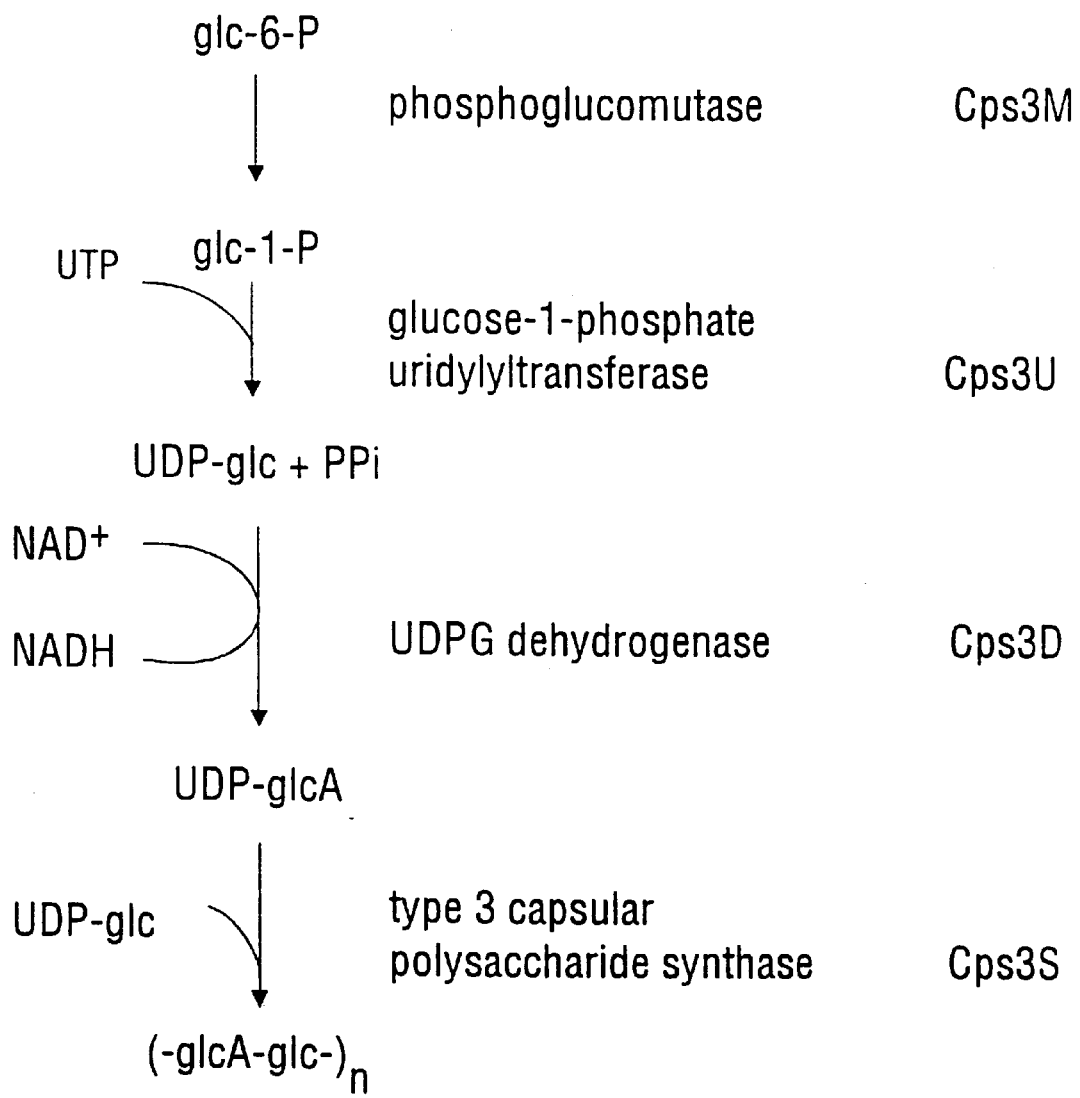
FIG. 10. Biosynthetic pathway for type 3 capsular polysaccharide. The functions of the proteins encoded by the type 3-specific genes, based on homologies, genetic, and biochemical data are shown. Additional functions may be necessary for capsule transport or attachment.

Neither cps3U nor cps3M appears to be required for type 3 capsule synthesis. Cps3M and Cps3U should function to convert glucose-6-phosphate into glucose-1phosphate, and glucose-1-phosphate into UDP-glucose, respectively (FIG. 10). Since UDP-glucose is necessary for the production of essential cell constituents, including teichoic acid and lipoteichoic acid (Austrian, et al., 1959), the products of other genes may complement the functions lost in Cps3U and Cps3M mutants. There are at least two plausible reasons for the retention of these genes in the type-specific region. One explanation is that their functions cannot be fully duplicated by the second enzymes. For example, they may play a role in regulating the amount of polysaccharide produced. Under given conditions, such as during infection, increased production of capsule could be advantageous. The large non-coding region upstream of cps3U might be a site at which regulation of cps3U and cps3M occurs. It should also be noted that the reactions carried out by Cps3M and Cps3U are each reversible, and the enzymes might be more active in the reverse reaction. Therefore, Cps3U and Cps3M might function to limit the amount of capsule produced.

Another possible explanation is that these genes were obtained along with the necessary type-specific genes in a horizontal transfer from another organism and have not been lost. This theory is consistent with the hybridization data indicating that none of the type-specific genes could be detected even at low stringency in strains of six other pneumococcal types, including types with related capsular polysaccharide structures (Dillard, et al., 1994). However, if these genes serve no necessary function, it is surprising that they have been maintained in the type 3 cassettes of multiple strains; i.e., the restriction maps of the type 3 regions of five non-clonal type 3 strains are identical, and all have cps3U and cps3M.

There are three requirements for a DNA region to be considered a gene cassette: 1) more than one copy of a gene or set of genes must exist, each specifying the production of a different, but related, product; 2) each copy must be flanked by DNA which is common to all the copies; and 3) cassettes must undergo recombination resulting in the replacement of one copy by another. More than 80 different capsular serotypes of *S. pneumoniae* have been identified, and the structures of more than half of the polysaccharides have been determined (van Dam, et al., 1990).

The presence of multiple types implies that as many different sets of genes exist. The inventors have shown that all the necessary genes specific for the production of capsules of types 2, 3, and 6B (Example 16) are closely linked to an approximate 1.2 kb fragment present in all capsule types examined. This fragment (corresponding to SEQ ID NO:6 and part of SEQ ID NO:5, see FIG. 4 and Example 5), cloned from the region flanking the type 3-specific genes, contains a gene with a sequence virtually identical to a gene fragment from type 2 strain, described by Pearce et al., and designated plpA (Pearce, et al., 1993). However, the flanking region from type 3 strain is distinct from the sequence described by Pearce et al. (1993) in that it is missing about one third of the 5' end of the gene, designated 'plpA. Furthermore Pearce et al. did not identify the location of the plpa gene nor did they attempt to define the sequences on either side of the gene.

The mapping studies reported here confirm that the regions to the right of this fragment are common for at least 4 kb. The regions map differently to the left of the fragment (Example 16), implying that these regions contain the type-specific genes in types 2 and 6B, as shown herein for type 3.

The upstream left flanking region from type 3, SEQ ID NO:1, SEQ ID NO:2, SEQ ID NO:3 and SEQ ID NO:4 is common to all capsule types examined (2, 3 and 6B, the Repeat region was also examined in 5, 6A, 8, 9 and 22; Example 17). However, the presence of multiple copies of the Repeat fragment (SEQ ID NO:4) has made the linkage in other types difficult to determine and it is possible that the repeat region may not flank the type-specific genes in other types.

Previous workers have provided biochemical evidence of replacement of capsule gene cassettes. When a type 1 and a type 2 strain were each transformed to type 14 or type 23, they no longer produced UDP-glucuronic acid, implying that the transformants had lost the UDP-glucose dehydrogenase gene (Austrian, et al., 1959). Similarly, a type 1 strain transformed to type 3 encapsulation no longer epimerized UDP-glucuronic acid to UDP-galacturonic acid. Molecular evidence is presented herein for the replacement of the type-specific genes for a type 3 strain transformed to type 2 encapsulation and a type 2 strain transformed to type 3 (Example 6). Together with Example 18, these observations provide strong evidence for a cassette organization of the type-specific genes.

Since the proposal was put forth that capsule genes are exchanged through a cassette-type recombination, there has always been one glaring exception—binary encapsulation. At low frequency, strains of certain capsule types transformed with DNA from strains of certain other capsule types were found to produce both polysaccharides (Austrian, et al., 1959). Evidently, cassette-type recombination had not occurred in these transformants since the genes for the original capsule had been maintained. Bernheimer et al., found that stable binary strains contained the second set of type-specific genes at a site unlinked to the recipient's type-specific genes (Bernheimer, et al., 1967). Unstable binary strains frequently lost the donor type-specific genes, which were usually located at a site linked to the recipient type-specific genes (Bernheimer, et al., 1967; Bernheimer and Wermundsen, 1969).

Figures 3A, 3B:
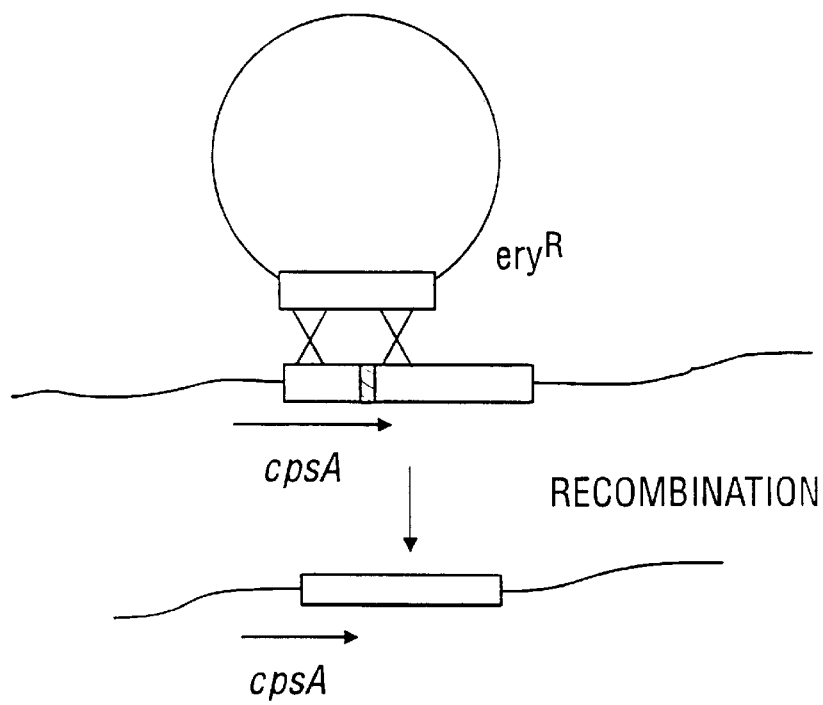
FIG. 3A. Repair of capsule mutations by double crossover recombination event. Mutants were transformed with plasmid subclones of pJD330 and no selection for Ery$^R$ was made. The box in the chromosome represents the region in the mutant chromosome homologous to the fragment cloned in pJD330. The plasmid represents a subclone of pJD330 capable of restoring encapsulation in the mutant strain.
FIG. 3B. Deletion analysis to locate the site of the cpsA1, capD4, and Rx1 mutations. The mutations were mapped by transformation with plasmid clones containing the indicated fragments and screening for the mucoid colony phenotype. Identical fragments repaired the cpsA1, capD4, and Rx1 mutations. No selection was made for insertion of the plasmids, thus these numbers represent double crossover events. The actual frequencies of repair, shown for the cpsA1-containing mutant, are mainly a reflection of the transformation efficiency of the recipient. No encapsulated transformants were obtained when pJY4163 (no insert) was used for transformation. Restriction sites are: M, MunI; P, PstI; Pv, PvuII; R. RsaI; S3, Sau3A I; Ss, SspI; Xb, XbaI.

Based on the hybridization data described here concerning the flanking regions and replacement of type-specific genes, as well as the work of Bernheimer concerning transformation to binary capsule types (Bernheimer, et al., 1968; Bernheimer, et al., 1967; Bernheimer, et al., 1969; Bernheimer and Wermundsen, 1972), the inventors can now propose models for capsule type change and binary capsule type formation. Cassette-type recombination would result from crossover events in the homologous flanking regions, leading to replacement of the type-specific genes. The left crossover could take place in the repeated element in strains containing this region linked to the type-specific genes but would occur in flanking DNA further upstream in strains that did not contain the repeat. This type of recombination is shown in FIG. 3A.

The finding of a repeated element upstream of the type 3 capsule genes (SEQ ID NO:4; Example 17) may provide an explanation for binary encapsulation. It is clear that at least one of the copies of the repeated fragment in types 2 and 6B is unlinked to the capsule genes, since neither of the type-specific cassettes could be moved with a marker inserted in this location. In type 3, a 2.2 kb HindIII fragment containing the repeat element is linked to the type-specific genes but based on transformation studies, an 8 kb fragment is not. The frequency of binary capsule transformants observed by Bernheimer et al., was significantly lower (10–1000 fold) than related transformations resulting in replacement, leading them to suggest that the recombination event involved strong homology at only one end. Once integrated at the "atypical" location (unlinked to the type-specific cassette), the genes for the second capsule type could not be moved to the normal location, except by transformation of a strain containing the genes of that type in the normal location, again suggesting that the non-type specific flanking DNA on at least one end had been lost (Bernheimer, et al., 1967; Bernheimer and Wermundsen, 1972).

Figure 15A:
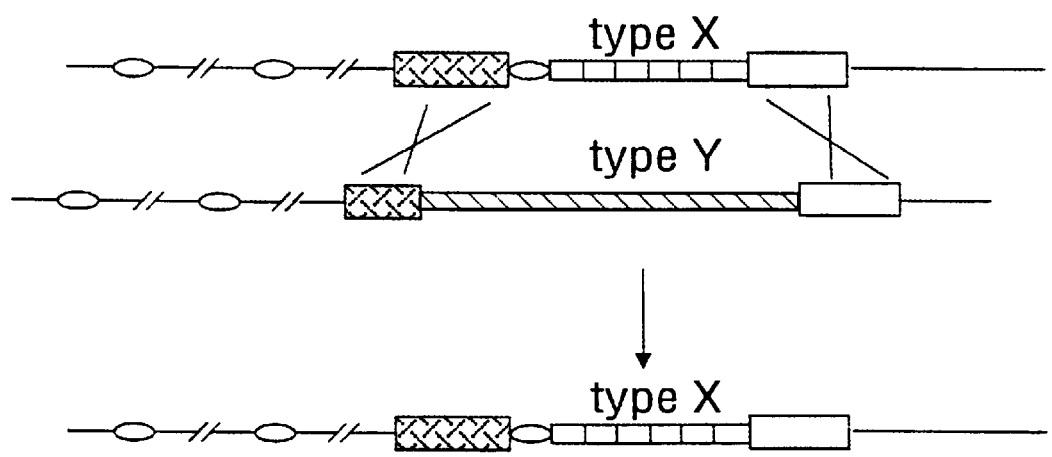
FIG. 15A. Model for the transfer of type-specific genes. Cassette type-recombination. Replacement of the recipient's type-specific genes with those of the donor results from homologous recombination between common regions that flank the type-specific cassettes. The open elipsoid symbol represents sequence containing repeated element; the black oblong symbol represents common DNA upstream of type-specific cassettes and; the open oblong symbol represents common DNA (including plpA) downstream of type-specific cassettes.
Figure 15B:
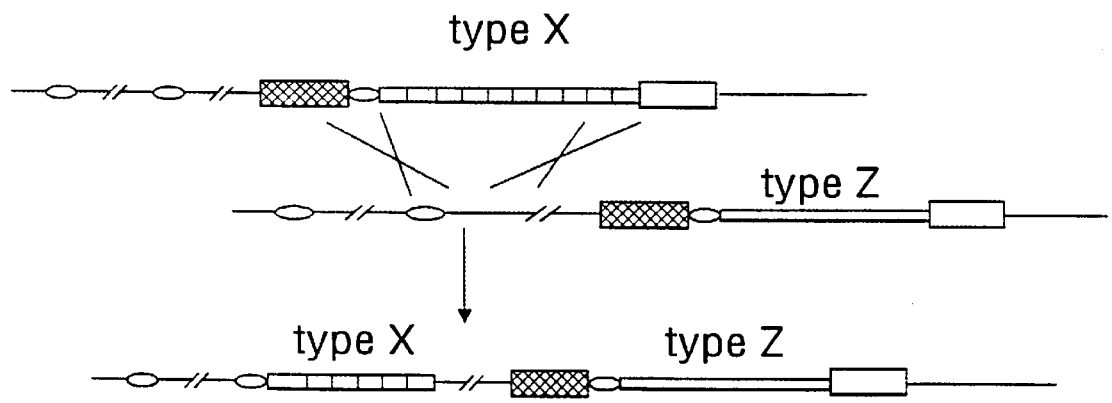
FIG. 15B. Model for the transfer of type-specific genes. Binary encapsulation by recombination involving homology at only one end. Integration at one end of the type-specific cassette would occur via homologous recombination through the repeated element. Integration at the other end would result from an apparent illegitimate recombination. Linkage of the two type-specific cassettes would result if the integration occurred in a repeat element in or closely linked to the recipient's capsule genes. Symbols represent the same as in FIG. 15A.

Since finding that part of the left flanking DNA (SEQ ID NO:4) is repeated in chromosomes of several strains, whereas the right flanking region is only present in one location, it is proposed that the repeated element of the left flanking region may be involved in the recombination that results in binary capsule type formation. The mechanism proposed by Bernheimer et al., for stable binary strains could involve homologous recombination at a repeated element unlinked to the capsule locus; the recombination at the other end of the capsule genes would occur by an apparent illegitimate recombination event, as shown in FIG. 15B.

Figure 15C:
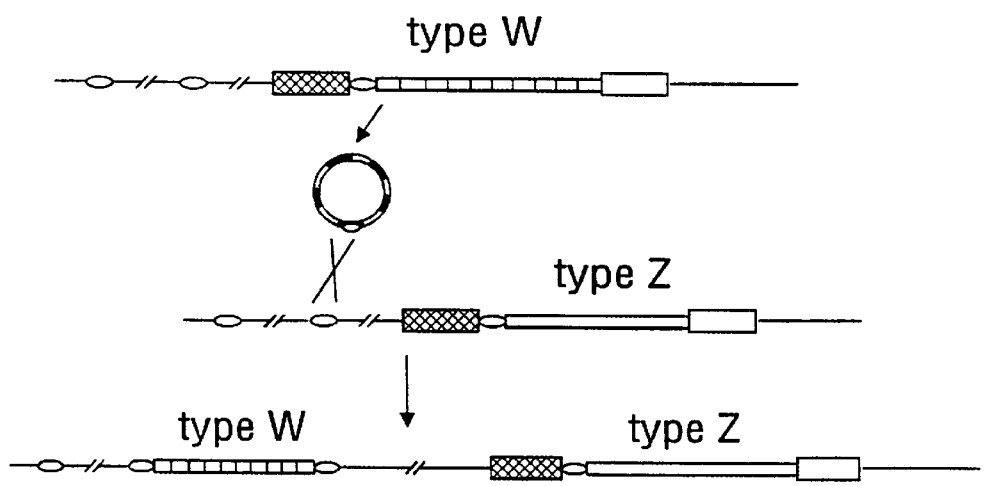
FIG. 15C. Model for the transfer of type-specific genes. Binary encapsulation via a transposition-like event. Type-specific cassettes flanked by the repeated element would resolve out of the chromosome and be transferred to recipient cells as circular intermediates. Recombination into the recipient chromosome could occur at a repeat element unlinked (as shown) or linked to the recipient's type-specific genes. Transfer of linear DNA could also yield binary strains as a result of recombination between the two repeat elements that flank the type-specific genes and two repeat elements that are closely linked in the recipient chromosome. Symbols represent the same as in FIG. 15A.

An alternative possibility for the generation of stable binary strains, shown in FIG. 15C, involves a transposition-like event that could result if certain type-specific genes are flanked on both sides by the repeated element. Unstable binary strains could result from either type of integration occurring at repeated elements in, or closely linked to, the recipient's type-specific genes. Instability could result from recombination through genes common to both capsule types, as suggested by Bernheimer et al., for the UDP-glucose dehydrogenases of types 1 and 3. Results presented here provide the basis for examining these possibilities. Binary strains containing the two sets of genes linked are of particular interest since they might recombine to form a novel capsule type. Examination of strains producing related capsule structures may help elucidate the possible mechanisms involved in novel capsule type formation.

Epidemiological studies have indicated that capsule type varies independently of other factors, suggesting that a substantial amount of genetic exchange has occurred (Crain et al., 1990; Coffey et al., 1991; Versalovic et al., 1993). Nonetheless, virulence of clinical isolates appears to correlate with the capsule type expressed (Briles et al., 1992). Taken together, these data suggest that the capsule type has a prominent role in determining virulence. However, epidemiological studies cannot demonstrate a causal relationship between capsule type and virulence due to the variability in the genetic backgrounds of the different serotypes. The characterization of the S. pneumoniae capsule locus described here has facilitated the construction of isogenic strains differing only in capsule type. These strains have been used to evaluate the role of capsule type in virulence (Example 18). The cloning of capsule genes and elucidation of the genetic organization of the capsule locus is a significant step toward understanding antigenic variation and virulence in this pathogen.

Cloning of the Type 3 region

There are a number of reasons for first cloning the type 3 specific genes: the type 3 capsule has a relatively simple structure that is expected to require a small number of genes for its synthesis; production of type 3 capsule is an easily identifiable phenotype; and finally, the availability of antibodies specific for the type 3 polysaccharide capsule allowed rapid screening for the presence of the capsule, of a large number of isolates, using an ELISA assay as described herein in Example 1. The approach provided and disclosed allowed for the first molecular genetic map of the cps gene locus.

The cloning of additional type-specific genes has been accomplished using the information derived from the present invention. Taking advantage of the non-type specific region one can isolate the DNA encoding other type-specific genes by simply obtaining a strain of *S. pneumoniae* known to have a type-specific capsule. Polymerase chain reaction using primers specific for opposite flanking regions and directed toward the opposite flanking non-type specific region are used to amplify the type-specific gene cassette. Where the size of the type-specific region is unknown, restriction fragment length polymorphism analysis, using probes specific for either or both of the non-type specific regions may be used to determine the size.

Antibodies specific for type-specific antigenic epitopes may be used with the present invention to distinguish and evaluate the stability of the *S. pneumoniae* strain prior to, and after cloning of the region. It will also be used for verifying the directed transfer of type-specific genes to a prospective host. Preferred hosts for polysaccharide capsule production will be gram positive bacteria, in particular members of the Streptococcus, Bacillus and even Staphylococcus species.

Selection of Hosts for Type-Specific Capsule Production

The present invention provides methods for the selection, isolation and transformation of Streptococcus sp. with a type-specific capsule polysaccharide gene locus. A cps locus can now be isolated and used to specifically change the capsular phenotype of a selected host organism. The preferred host organism for use with the present invention is a bacteria that produces high amounts of the capsular polysaccharide.

Once a suitable high producing host is identified, it will be used to carry the type-specific genes of choice, as shown in Examples 6 and 18. The organisms can be converted to other serotypes by transforming the high producing recipient bacteria with a gene cassette or with intact genomic DNA. A gene cassette, as previously mentioned, is a segment of DNA comprising of one or more genes flanked by specific DNA sequences which enables incorporation of the cassette into a recipient's cell chromosome at a specific site or locus via homologous recombination. A cassette may contain type-specific genes, either alone or in combination with non-type specific genes. Of course, the preferred construct for transfection will be a cassette containing the non-type specific flanking regions.

A cassette of the cps locus comprising of the cps genes and the 5' and 3' flanking regions donated from any one of the 85 *S. pneumoniae* serotypes may be transformed into a recipient *S. pneumoniae* also belonging to any one of the 85 serotypes. During transformation, recombination would occur in the flanking regions, resulting in the replacement of the recipient's type-specific region by that of the donor. The capsule type of the recipient would be expected to change to that of the donor.

The introduction of a gene cassette comprising of the cps locus or DNA segment or genetic element, into *S. pneumoniae* may be performed by a variety of methods. A particularly preferred embodiment would be to digest the donor *S. pneumoniae* genomic DNA with one or more restriction enzymes such as those described in Table 1, for example, and then separate the entire cps locus from the rest of the genomic DNA by gel purification., This specific DNA segment, cps locus or genetic element, may then be ligated into a vector such as a plasmid or cosmid or bacteriophage, and transformed by various methods into the recipient *S. pneumoniae*. Alternatively, the donor *S. pneumoniae's* entire genomic DNA may be naturally transformed into the recipient by a suitable method, e.g., as described in Example 1. Further still, the donor's genomic DNA may be digested with one or more restriction enzymes and then ligated into a plasmid, cosmid or bacteriophage, without selecting specifically for the cps locus. This may then be transformed into the recipient *S. pneumoniae*.

TABLE 1

RESTRICTION ENZYMES

| | |
|---|---|
| Aat II | GACGT/C |
| Acc I | GT/MKAC |
| Acc II | CG/CG |
| Acc III | T/CCGGA |
| Aci I | CCGC(2/2) |
| Acy I | GR/CGYC |
| Afl II | C/TTAAG |
| Afl III | A/CRYGT |
| Age I | A/CCGGT |
| Aha III | TTT/AAA |
| Alu I | AG/CT |
| AlwN I | CAGNNN/CTG |
| Aoc I | CC/TNAGG |
| Apa I | GGGCC/C |
| ApaB I | GCANNNN/TGC |
| ApaL I | G/TGCAC |
| Asc I | GG/CGCGCC |
| Asu I | G/GNCC |
| Asu II | TT/CGAA |
| Ava I | C/YCGRG |
| Ava II | G/GWCC |
| Ava III | ATGCAT |
| Avr III | C/CTAGG |
| Bae I | ACNNNNGTAYC |
| Bal I | TGG/CCA |
| BamH I | G/GATCC |
| Bbv I | GCAGC(8/12) |
| Bbv II | GAAGAC(2/6) |
| Bcc I | CCATC |
| Bcef I | ACGGC(12/13) |
| Bcg I | GCANNNNNCG(12/10) |
| Bcl I | T/GATCA |
| Bet I | W/CCGGW |
| Bgl I | GCCNNNN/NGGC |
| Bgl II | A/GATCT |
| Bin I | GGATC(4/5) |
| Bpu10 I | CCTNAGC(-5/2) |
| Bpu1102 I | GC/TNAGC |
| Bsp1286 I | GDGCH/C |
| Bsp106 I | AT/CGAT |
| BspC I | CGAT/CG |
| BsaA I | YAC/GTR |
| BsaB I | GATNN/NNATC |
| BseP I | GCGCGC |
| Bsg I | GTGCAG(16/14) |
| Bsi I | CTCGTG(5/1) |
| BsiY I | CCNNNNN/NNGG |
| Bsm I | GAATGC(1/-1) |
| BsmA I | GTCTC(1/5) |

TABLE 1-continued

RESTRICTION ENZYMES

| | |
|---|---|
| Bsp50 I | CG/CG |
| BspG I | CG/CGCTGGAC |
| BspH I | T/CATGA |
| BspM I | ACCTGC(4/8) |
| BspM II | T/CCGGA |
| Bsr I | ACTGG(1/-1) |
| BsrB I | GAGCGG(-3/-3) |
| BstE II | G/GTNACC |
| BstN I | CC/WGG |
| BstX I | CCANNNNN/NTGG |
| Cac8 I | GCN/NGC |
| Cau II | CC/SGG |
| Cfr I | Y/GGCCR |
| Cfr10 I | R/CCGGY |
| Cla I | AT/CGAT |
| CviJ I | RG/CY |
| CviR I | TG/CA |
| Dde I | C/TNAG |
| Dpn I | GA/TC |
| Dra I | TTT/AAA |
| Dra II | TG/GNCCY |
| Dra III | CACNNN/GTG |
| Drd I | GACNNNN/NNGTC |
| Drd II | GAACCA |
| Dsa I | C/CRYGG |
| Eam1105 I | GACNNN/NNGTC |
| Eci I | TCCGCC |
| Eco3 II | GGTCTC(1/5) |
| Eco47 III | AGC/GCT |
| Eco52 I | C/GGCCG |
| Eco57 I | CTGAAG(16/14) |
| EcoN I | CCTNN/NNNAGG |
| EcoR I | G/AATTC |
| EcoR II | /CCWGG |
| Ecor V | GAT/ATC |
| Esp I | GC/TNAGC |
| Esp3 I | CGTCTC(1/5) |
| Fau I | CCCGC(4/6) |
| Fin I | GTCCC |
| Fnu4H I | GC/NGC |
| FnuD II | CG/CG |
| Fok I | GGATG(9/13) |
| Fse I | GGCCGG/CC |
| Fsi I | R/AATTY |
| Gdi II | YGGCCG(-5/-1) |
| Gsu I | CTGAAG(16/14) |
| Hae I | WGG/CCW |
| Hae II | RGCGC/Y |
| Hae III | GG/CC |
| Hga I | GACGC(5/10) |
| HgiA I | GWGCW/C |
| HgaC I | G/GYRCC |
| HgiE II | ACCNNNNNGGT |
| HgiJ II | GRGCY/C |
| Hha I | GCG/C |
| Hind II | GTY/RAC |
| Hind III | A/AGCTT |
| Hinf I | G/ANTC |
| Hinl I | GR/CGYC |
| Hpa I | GTT/AAC |
| Hpa II | C/CGG |
| Hph I | GGTCA(8/7) |
| Kpn I | GGTAC/C |
| Ksp632 I | CTCTTC(1/4) |
| Ksp I | CCGC/GG |
| Mae I | C/TAG |
| Mae II | A/CGT |
| Mae III | /GTNAC |
| Mbo I | /GATC |
| Mbo II | GAAGA(8/7) |
| Mcr I | CGRY/CG |
| Mfe I | C/AATTG |
| Mlu I | A/CGCGT |
| Mly I | GACTC(5/5) |
| Mme I | TCCRAC(20/18) |
| Mnl I | CCTC(7/7) |
| Mse I | T/TAA |

TABLE 1-continued

RESTRICTION ENZYMES

| | |
|---|---|
| Msp I | C/CGG |
| Mst I | TGC/GCA |
| Mst II | CC/TNAGG |
| Mwo I | GCNNNNN/NNGC |
| Nae I | GCC/GGC |
| Nar I | GG/CGCC |
| Nci I | CC/SGG |
| Nco I | C/CATGG |
| Nde I | CA/TATG |
| Nhe I | G/CTAGC |
| Nla III | CATG/ |
| Nla IV | GGN/NCC |
| Not I | GC/GGCCGC |
| Nru I | TCG/CGA |
| Nsi I | ATGCA/T |
| Nsp I | RCATG/Y |
| NspB II | CMG/CKG |
| Pac I | TTAAT/TAA |
| Pal I | GG/CC |
| Pfl1108 I | TCGTAG |
| PflM I | CCANNNN/NTGG |
| Ple I | GAGTC(4/5) |
| PmaC I | CAC/GTG |
| Pme I | GTTT/AAAC |
| PpuM I | RG/GWCCY |
| PshA I | GACNN/NNGTC |
| PspA I | C/CCGGG |
| Pst I | CTGCA/G |
| Pvu I | CGAT/CG |
| Pvu II | CAG/CTG |
| RleA I | CCCACA(12/9) |
| Rsa I | GT/AC |
| Rsr II | CG/GWCCG |
| Sac I | GAGCT/C |
| Sac II | CCGC/GG |
| Sal I | G/TCGAC |
| Sap I | GCTCTTC(1/4) |
| Sau3A I | /GATC |
| Sau96 I | G/GNCC |
| Sau I | CC/TNAGG |
| Sca I | AGT/ACT |
| ScrF I | CC/NGG |
| Sdu I | GDGCH/C |
| Sec I | C/CNNGG |
| SfaN I | GATC/(5/9) |
| Sfc I | CTYRAG |
| Sfe I | C/TYRAG |
| Sfi I | GGCCNNNN/NGGC |
| SgrA I | CR/CCGGYG |
| Sma I | CCC/GGG |
| Sna I | CTATAC |
| SnaB I | TAC/GTA |
| Spe I | A/CTAGT |
| Sph I | GCATG/C |
| Spl I | C/GTACG |
| Srf I | GCCC/GGGC |
| Sse838 I | CCTGCA/GG |
| Ssp I | AAT/ATT |
| Stu I | AGG/CCT |
| Sty I | C/CWWGG |
| Swa I | ATTT/AAAT |
| Taq I | T/CGA |
| Taq II | GACCGA(11/9) |
| Tfi I | GAWTC |
| Tsp45 I | GTSAC |
| Tsp E I | AATT |
| Tth111 I | GACN/NNGTC |
| Tth111 II | CAARCA(11/9) |
| Vsp I | AT/TAAT |
| Xba I | T/CTGAGA |
| Xcm I | CCANNNNN/NNNNTGG |
| Xho I | C/TCGAG |
| Xho II | R/GATCY |
| Xma I | C/CCGGG |
| Xma III | C/GGCCG |
| Xmn I | GAANN/NNTTC |

Nucleic Acid Hybridization

The DNA sequences disclosed herein will find utility as probes or primers in nucleic acid hybridization embodiments. As such, it is contemplated that oligonucleotide fragments corresponding to the sequence(s) of SEQ ID NO:1, SEQ ID NO:2 and SEQ ID NO:3 (including sequences in between), SEQ ID NO:4, SEQ ID NO:5 and SEQ ID NO:6 for stretches of between about 10–14 nucleotides to about 20 or to about 30 nucleotides will find particular utility, with even longer sequences, e.g., 40, 50, 100, 200, 500, and even up to full length, being more preferred for certain embodiments. The ability of such nucleic acid probes to specifically hybridize to non-type-specific and to type-specific-encoding sequences will enable them to be of use in a variety of embodiments. For example, the probes can be used in a variety of assays for detecting the presence of complementary sequences in a given sample, as may be used, for example to isolate related type-specific genes. Alternatively, one may use the non-type-specific regions to aid in the isolation and cloning of additional type-specific cassettes. However, other uses are envisioned, including the use of the sequence information for the preparation of mutant species primers, or primers for use in preparing other genetic constructions.

Nucleic acid molecules having stretches of about 10–14, 20, 30, 50, or even of about 100–200 nucleotides or so, complementary to SEQ ID NO:1, SEQ ID NO:2 and SEQ ID NO:3 (including sequences in between), SEQ ID NO:4, SEQ ID NO:5 and SEQ ID NO:6, will have utility as hybridization probes. These probes will be useful in a variety of hybridization embodiments, such as Southern and Northern blotting in connection with analyzing genomic structure and organization of type-specific genes or both linked and non-linked regulatory genes in diverse strains of S. pneumoniae. The total size of fragment, as well as the size of the complementary stretch(es), will ultimately depend on the intended use or application of the particular nucleic acid segment. Smaller fragments will generally find use in hybridization embodiments, wherein the length of the complementary region may be varied, such as between about 10–14 and about 100 nucleotides, or even up to full length according to the complementary sequences one wishes to detect.

The use of a hybridization probe of about 10–14 nucleotides in length allows the formation of a duplex molecule that is both stable and selective. Molecules having complementary sequences over stretches greater than 10–14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (incorporated herein by reference) or by introducing selected sequences into recombinant vectors for recombinant production.

Accordingly, the nucleotide sequences of the invention may be used for their ability to selectively form duplex molecules with complementary stretches of non-type- and of type-specific genes. Depending on the application envisioned, one will desire to employ varying conditions of hybridization to achieve varying degrees of selectivity of probe towards target sequence. Such hybridization conditions are standard in the art and include low stringency and high stringency. For applications requiring high selectivity, one will typically desire to employ relatively stringent conditions to form the hybrids, e.g., one will select relatively low salt and\or high temperature conditions, such as provided by 0.02M–0.15M NaCl at temperatures of 50° C. to 70° C. One particular example is using the QuickHyb® system (Stratagene's Illuminator™ Nonradioactive Detection System) at 68° C. Such selective conditions tolerate little, if any, mismatch between the probe and the template or target strand, and would be particularly suitable for isolating other genes encoding gene products that are involved in the production of capsule polysaccharides. A preferred embodiment for hybridization conditions is described in detail in Example 4. Further standard hybridization conditions can be found in Sambrook et al., (1989), and are known to those of skill in the art.

Of course, for some applications, for example, where one desires to prepare mutants employing a mutant primer strand hybridized to an underlying template or where one seeks to isolate type-specific-encoding sequences from related species, functional equivalents, or the like, less stringent hybridization conditions will typically be needed in order to allow formation of the heteroduplex.

One may also desire to employ other hybridization techniques and to change salt conditions such as varying the amount of salt from between about 0.15M–0.9M. Other parameters that can be modified may be temperature such as those ranging from 20° C. to 55° C. to optimize the signal-to-noise ratio to reduce unwanted background. The techniques for optimizing hybridization conditions are well known to those of skill in the art and are generally also described within the instruction manual for various reagents and apparatus.

In any case, it is generally appreciated that conditions can be rendered more stringent by the addition of increasing amounts of formamide, which serves to destabilize the hybrid duplex in the same manner as increased temperature. Thus, hybridization conditions can be readily manipulated as is known to those of skill in the art, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Longer DNA segments will often find particular utility in the recombinant production of peptides or proteins. DNA segments which encode peptide antigens from about 15 to about 50 amino acids in length, or more preferably, from about 15 to about 30 amino acids in length are contemplated to be particularly useful, as are DNA segments encoding entire cps locus encoded proteins, such as those of SEQ ID NO:1, SEQ ID NO:2, SEQ ID NO:3, SEQ ID NO:5 and SEQ ID NO:6. DNA segments encoding peptides will generally have a minimum coding length in the order of about 45 to about 150, or to about 90 nucleotides.

The nucleic acid segments of the present invention, regardless of the length of the coding sequence itself, may be combined with other DNA sequences, such as promoters, repressors, attenuators, additional restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol. For example, nucleic acid fragments may be prepared in accordance with the present invention which are up to about 10,000 base pairs in length, with segments of about 5,000 or 3,000 being preferred and segments of about 1,000 base pairs in length being particularly preferred.

It will be understood that this invention is not limited to the particular nucleic acid sequences of SEQ ID NO:1, SEQ ID NO:2, SEQ ID NO:3, SEQ ID NO:4, SEQ ID NO:5 and SEQ ID NO:6, or to the particular amino acid sequences of SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 and SEQ ID NO:16. Therefore, DNA segments prepared in accordance with the present invention may also encode biologically functional equivalent proteins or peptides which have variant amino acids sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged.

DNA segments encoding a gene, including the cpsB, cpsC, cpsE, cspD, cspS, cspU, cspM, plpA and tnpA genes may be introduced into recombinant host cells and employed for expressing and producing the type-specific proteins for use in producing type-specific capsule polysaccharides. Alternatively, through the application of genetic engineering techniques, subportions or derivatives of selected type-specific gene locus genes may be employed. Equally, through the application of site-directed mutagenesis techniques, one may re-engineer DNA segments of the present invention to alter the coding sequence, e.g., to introduce improvements to the antigenicity of the protein or to test mutants in order to examine the production of capsule polysaccharides at the molecular level. Where desired, one may also prepare fusion peptides, e.g., where the type-specific coding regions are aligned within the same expression unit with other proteins or peptides having desired functions, such as for immunodetection purposes (e.g., enzyme label coding regions).

Screening Method Type-Specific Genes

Screening for type-specific genes provides another utility for the cps loci of the present invention. A type-specific screening protocol will allow for the epidemiological identification of S. pneumoniae and its serotypes at the molecular level. By using one or both of the non-type specific regions as probes one can determine the presence of S. pneumoniae from a small sample by immobilizing DNA from the sample onto a solid matrix, for example a slot blot using nitrocellulose, and hybridizing thereto a probe as described in the present invention.

Using either or both of the non-type specific regions of the present invention as a probe or probes one may also screen southern blots. The screening of southern blots may allow one to determine not only the presence of S. pneumoniae but also the exact genotype of S. pneumoniae present in the sample. In conjunction with densitometric analysis of a southern blot containing multiple serotypes on may determine not only the relative frequency of serotypes within a sample, but in addition one may examine the changing characteristics of the serotypes by examining samples taken at distinct time periods.

It also allows the clinician to determine if a patient is having a recurrence of a particular serotype, if the patient is susceptible to a particular serotype or types, or if a new serotype is increasing in the population.

Site-Specific Mutagenesis

Site-specific mutagenesis, also known as site-directed mutagenesis, is a technique useful in the preparation of changes, directed by the laboratory technician, that change the characteristics of genes and their gene products, for the addition of restriction sites, for modifying the activity of promoters, repressors, attenuators, and for directed changes affecting recombination. All of these changes may be produced through specific mutagenesis of the underlying non-type- and type-specific DNA of the present invention. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes the type-specific protein or proteins encoded by the type-specific gene locus. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of type-specific genes using site-directed mutagenesis is provided as a means of producing potentially useful species, for example a strain having enhanced production of type-specific capsular polysaccharides, and is not meant to be limiting as there are other ways in which sequence variants of other type-specific genes may be obtained. For example, recombinant vectors encoding other type-specific genes, as described herein using the non-type specific regions of the capsule polysaccharide gene cassette are encompassed.

Biological Functional Equivalents

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

As used in this application, the term "DNA segment" refers to a DNA molecule that has been isolated free of total genomic DNA of a particular species. Therefore, a DNA segment encoding the cps locus refers to a DNA segment that contains the 5' and/or 3' flanking regions, or the cpsB, cpsC, cpsE, cpsD, cpsS, cpsU, cpsM, tnpA or plpA coding sequences, yet is isolated away from, or purified free from, total genomic DNA of S. pneumoniae. Included within the term "DNA segment", are DNA segments and smaller fragments of such segments, and also recombinant vectors, including, for example, plasmids, cosmids, phage, viruses, and the like.

Similarly, a DNA segment comprising an isolated or purified 5' or 3' flanking region, or cpsB, cpsC, cpsE, cpsD, cpsS, cpsU, cpsM, plpA or even tnpA gene, refers to a DNA segment including the coding sequences and, in certain aspects, regulatory sequences, isolated substantially away from other naturally occurring genes or protein encoding sequences. In this respect, the term "gene" is used for simplicity to refer to a protein, polypeptide or peptide encoding unit. As will be understood by those in the art, this term includes both genomic sequences, cDNA sequences and smaller engineered gene segments that express, or may be adapted to express, proteins, polypeptides or peptides.

"Isolated substantially away from other coding sequences" means that the locus of interest, in this case the 5' or 3' flanking regions, or cps B, cpsC, cpsE, cpsD, cpsS, cpsU, cpsM, tnpA or plpA coding sequences, forms the significant part of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the laboratory technician.

In particular embodiments, the invention concerns isolated DNA segments and recombinant vectors incorporating DNA sequences that include the 5' or 3' flanking regions denoted by SEQ ID NO:1, SEQ ID NO:2, SEQ ID NO:3 and SEQ ID NO:4 or SEQ ID NO:6, respectively. DNA segments and vectors that incorporate DNA sequences that encode CpsB, CpsC, CpsE, CpsD, CpsS, CpsU, CpsM, PlpA or transposase A proteins that include within their amino acid sequences an amino acid sequence as set forth in SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 or SEQ ID NO:16 respectively are also included.

The term "a sequence as set forth in SEQ ID NO:7–16" means that the sequence substantially corresponds to a portion of SEQ ID NO:7–16 and has relatively few amino acids that are not identical to, or a biologically functional equivalent of, the amino acids of SEQ ID NO:7–16. The term "biologically functional equivalent" is well understood in the art and is further defined in detail herein. Accordingly, sequences that have between about 75% and about 85%; or more preferably, between about 86% and about 95%; or even more preferably, between about 96% and about 99%; of amino acids that are identical or functionally equivalent to the amino acids of SEQ ID NO:7–16 will be sequences that are "essentially as set forth in SEQ ID NO:7–16."

Naturally, it will be understood that for the Cps proteins, the definition of "equivalents" in this sense does not extend to distinct, but homologous proteins, such as CpsD and HasB from *Streptococcus pyogenes*; CpsS and HasA from *S. pyogenes*, NodC from *Rhizobium meliloti;* nor CpsU and GtaB from *Bacillus subtilis*. Rather, the scope of equivalents contemplated are such that the changes made still result in a protein that is structurally and functionally a Cps protein.

In certain other embodiments, the invention concerns isolated DNA segments and recombinant vectors that include within their sequence a nucleic acid sequence essentially as set forth in SEQ ID NO:1, SEQ ID NO:2, SEQ ID NO:3, SEQ ID NO:4 and SEQ ID NO:6, for the flanking regions; and SEQ ID NO:5 for the type-specific encoding regions. The term "as set forth in SEQ ID NO:5" is used in the same sense as described above and means that the nucleic acid sequence substantially corresponds to a portion of SEQ ID NO:5 and has relatively few codons that are not identical, or functionally equivalent, to the codons of SEQ ID NO:5. The term "functionally equivalent codon" is used herein to refer to codons that encode the same amino acid, such as the six codons for arginine or serine, and also refers to codons that encode biologically equivalent amino acids (as in Table 2).

It will be understood that acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to coding nucleic acid sequences that may, for example, include various non-coding sequences flanking either of the 5' or 3' portions of the coding region, such as promoters.

Allowing for the degeneracy of the genetic code, sequences that have between about 75% and about 85%; or more preferably, between about 85% and about 95%; or even more preferably, between about 95% and about 99% of nucleotides that are identical to the nucleotides of SEQ ID NO:1, SEQ ID NO:2, SEQ ID NO:3, SEQ ID NO:4, SEQ ID NO:5 or SEQ ID NO:6 (SEQ ID NO:1–6), will be sequences that are "as set forth in SEQ ID NO:1–6". Sequences that are essentially the same as those set forth in SEQ ID NO:1–6 may also be functionally defined as sequences that are capable of hybridizing to a nucleic acid segment containing the complement of SEQ ID NO:1–6 under standard conditions. Suitable hybridization conditions will be well known to those of skill in the art and are clearly set forth herein, e.g., see Example 4.

TABLE 2

Amino Acids and the Corresponding Codons.

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA CUC CUG CUU | |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA CGC CGG | CGU |
| Serine | Ser | S | AGC | AGU | UCA UCC UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

Naturally, the present invention also encompasses DNA segments that are complementary, or essentially complementary, to the sequences set forth in SEQ ID NO:1, SEQ ID NO:2, SEQ ID NO:3, SEQ ID NO:4, SEQ ID NO:5 and SEQ ID NO:6. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1–6 under relatively stringent conditions such as those described herein as SEQ ID NO:1, SEQ ID NO:2, SEQ ID NO:3, SEQ ID NO:4, SEQ ID NO:5 and SEQ ID NO:6.

The DNA segments of the present invention include those encoding biologically functional equivalent proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed in the laboratory, may be introduced through the application of site-directed mutagenesis techniques, e.g., to introduce improvements to the antigenicity of the protein or to test *S. pneumoniae* mutants in order to examine capsular productivity at the molecular level.

If desired, one may also prepare fusion proteins and peptides, e.g., where the cpsB, cpsC, cpsE, cpsD, cpsS, cpsU, cpsM, plpA and tnpA coding regions are aligned within the same expression unit with other proteins or peptides having desired functions, such as for purification or immunodetection purposes (e.g., proteins that may be purified by affinity chromatography and enzyme label coding regions, respectively).

As mentioned above, modification and changes may be made in the structure of CpsB, CpsC, CpsE, CpsD, CpsS, CpsU, CpsM, plpA or tnpA and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules, receptors, or catalytic regulation of capsular polysaccharide production. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. Equally, the same considerations may be employed to create a protein or polypeptide with countervailing (e.g., antagonistic) properties. It is thus contemplated by the inventors that various changes may be made in the sequence of SEQ ID NO:7, SEQ ID NO:11, SEQ ID NO:12, SEQ ID NO:13 or SEQ ID NO:14, SEQ ID NO:15 or SEQ ID NO:16 proteins or peptides (or underlying DNA) without appreciable loss of their biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. In particular, the function of given protein must be retained to be an equivalent. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged. This is the case in the present invention, where CpsD has a putative NAD-binding site and active site region at residues 2 to 29 and 251–263 (SEQ ID NO:11) respectively.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is therefore understood that an amino acid can be substituted for another having a similar hydrophilicity value and still obtain a biologically equivalent, and in particular, an immunologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Antibody Generation

Means for preparing and characterizing antibodies are well known in the art (See, e.g., Antibodies: A Laboratory Manual, Cold Spring Harbor Laboratory, 1988; incorporated herein by reference). This invention thus contemplates the generation of antibodies against the proteins CpsB, CpsC, CpsE, CpsD, CpsS, CpsU, CpsM, PlpA and transposase A or peptides derived therefrom. The CpsB, CpsC, CpsE, CpsD, CpsS, CpsU, CpsM, PlpA and transposase A proteins or peptides may be obtained using standard methods of recombinant expression as is routinely in the art.

The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of-boosting and titering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified CpsB, CpsC, CpsE, CpsD, CpsS, CpsU, CpsM, PlpA or transposase A protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). cites). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XXO Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Isolation and Characterization of Capsule Mutants

A. Methods

1. Bacterial strains, plasmids, and culture conditions

The bacterial strains and plasmids used are listed herein in Table 3. Culture conditions for *S. pneumoniae* and *E. coli* were previously described (Dillard and Yother, 1991). Erythromycin was used at 0.3 μg/ml and streptomycin was used at 100 μg/ml in *S. pneumoniae* cultures where indicated. Chloramphenicol was used at 1 μg/ml to detect transcription in *S. pneumoniae* isolates carrying pJY4163/4164 chromosomal insertions.

TABLE 3

| Strain/Plasmid | Derivation and properties | Source/Reference |
|---|---|---|
| Strain | | |
| *S. pneumoniae* | | |
| WU2 | Type 3 encapsulated | Briles et. al. (1991b) |
| D39 | Type 2 encapsulated | Avery et al. (1944) |
| Rx1 | Non-encapsulated mutant of R36A-A66 hybrid | Ravin (1959) Shoemaker and Guild (1974) |
| L8-20D6 | Type 1 encapsulated | Dillard and Yother (1994) |
| DBL5 | Type 5 encapsulated | Yother et al. (1982) |
| BG9273 | Type 6A encapsulated | Dillard and Yother (1994) |
| EP2809 | Type 8 encapsulated | Dillard and Yother (1994) |
| BG5862 | Type 9 encapsulated | Dillard and Yother (1994) |
| LM100 | Type 22 encapsulated | Dillard and Yother (1994) |

TABLE 3-continued

| Strain/Plasmid | Derivation and properties | Source/Reference |
|---|---|---|
| A66R$_2$ | Non-encapsulated mutant of A66 (Type 3) | Muckerman et al. (1982) |
| 661 | Non-encapsulated mutant of A66 (Type 3) | Bemheimer and Wermundsen (1972) |
| JD531 | Non-encapsulated mutant of WU2, Em$^R$, cpsA1 | This work |
| JD541 | Non-encapsulated mutant of WU2, EM$^R$, cpsA2 | This work |
| JD542 | Non-encapsulated mutant of WU2, Em$^R$, cpsB1 | This work |
| JD551 | Non-encapsulated mutant of WU2, Em$^R$, cpsB2 | This work |
| JD571 | Non-encapsulated mutant of WU2, Em$^R$, cpsB3 | This work |
| JD600 | WU2 Str$^R$ | This work |
| JD611 | JD600 × JD531, Em$^s$, Str$^R$, cpsA1 | This work |
| JD614 | JD600 × JD551, Em$^s$, Str$^R$, cpsB2 | This work |
| JD619 | JD600 × JD541, Em$^s$, Str$^R$, cpsA2 | This work |
| JD692 | JD600 × JD542, Em$^s$, Str$^R$, cpsB1 | This work |
| JD816 | JD600 × JD671, Em$^s$, Str$^R$, cpsB3 | This work |
| JD636 | WU2 Str$^R$, RM$^R$, Nov$^R$ | This work |
| JD752 | Isolate of transformation pool W62 × JD811, type 3 encapsulated, Em$^R$ | This work |
| JD770 | pJD330 × WU2, type 3 encapsulated, Em$^R$ | This work |
| JD893 | JD770 × D39, type 3 encapsulated, Em$^R$ | This work |
| JD871 | pJD366 × D39, type 2 encapsulated, Em$^R$ | This work |
| JD872 | JD871 × WU2, type 2 encapsulated, Em$^R$ | This work |
| JD875 | pJD366 × DBL5, type 5 encapsulated, Em$^R$ | This work |
| JD908 | pJD369 × WU2, non-encapsulated, Em$^R$ | This work |
| *E. coli* | | |
| LE392 | F$^-$hsdR514 (T$_k^-$M$_k^-$) supE44 supF58 Δ (faciZY)6 galK2 galT22 met21 trpR55 λ | Tilghman et al. (1977) |
| pJY4163 and pJY4164 | Lack origin of replication for *S. pneumoniae* Promoterless cat gene downstream of multiple cloning site (opposite orientations in 4163, 4164), Em$^R$ | Yother et al. (1992) |
| pJD330 | WU2 Sau3A1 fragment cloned into pJY4163 BamHI site, isolated from JD752 | This work |
| pJD337 | pJY4163:: 1.5 kb XbaI-PvuII fragment of pJD330 | This work |

TABLE 3-continued

Bacterial strains and plasmids.

| Strain/Plasmid | Derivation and properties | Source/Reference |
|---|---|---|
| pJD343 | pJY4164:: 0.4 kb MunI fragment of pJD330 | This work |
| pJD345 | pJY4164:: 1.1 kb MunI fragment of pJD330 | This work |
| pJD351 | pJY4164:: 2.4 kb Sau3AI-Sau3AI fragment of pJD330 orientation opposite pJD330 | This work |
| pJD353 | pJY4164:: 1.6 kb Sau3AI-XbaI fragment of pJD330 | This work |
| pJD357 | pJY4164:: 0.3 kb MunI-Sau3AI fragment of JD330 | This work |
| pJD359 | pJY4164:: 0.6 kb PvuII-HaeIII fragment of pJD330 | This work |
| pJD361 | pJY4164:: 0.45 kb XbaI-PstI fragment of pJD330 | This work |
| pJD362 | pJY4164:: 0.4 kb HaeIII-MunI fragment of pJD330 | This work |
| pJD364 | WU2 3.2 kb HindIII fragment cloned into pJY4164 HindII site | This work |
| pJD366 | WU2 3.2 kb HindIII fragment cloned into pJY4164 HindIII site, orientation opposite pJD364 | This work |
| pJD368 | pJD4164:: 0.45 kb RsaI-MunI fragment of pJD330 | This work |
| pJD369 | pJY4164:: 0.55 kb PvuII-MunI fragment of pJD330 | This work |
| pJD374 | WU2 1.2 kb Sau3AI fragment cloned in pJY4163 | This work |
| pJD377 | pJY4164:: 1.2 kb SacI-HindIII fragment of pJD364 | This work |
| pJD380 | pJY4164:: 0.36 kb Sau3AI-SspI fragment of pJD330 | This work |

Em$^R$, erythromycin resistant; Em$^s$, erythromycin sensitive; Str$^R$, streptomycin resistant; Rif$^R$, rifampicin resistant; Nov$^R$, novobiocin resistant.

2. General DNA techniques

Techniques for DNA fragment isolation, ligations, and plasmid isolation and purification were performed as previously described (Dillard and Yother, 1991; and as described by Sambrook et al., 1989, the relevant portions incorporated herein by reference). Plasmid screenings were done by scraping colonies from agar plates and incubating these in the lysis solution of Kado and Liu, 30% SDS, 50 mM Tris, pH 12.6 (Kado and Liu, 1981). The lysates were run on agarose gels to determine plasmid sizes.

3. Library construction

A plasmid library of random fragments was constructed by digesting chromosomal DNA from S. pneumoniae strain WU2 to completion with Sau3AI and ligating these fragments into the BamHI site of pJY4163. The resulting ligation mixture was electroporated into E. coli LE392, and transformants were selected on L agar plates containing 300 μg erythromycin/ml. Individual colonies were patched on erythromycin plates. Each plate contained 100 colonies and constituted a pool. Transformants were pooled by scraping the plates.

4. Transformations

Encapsulated strains of S. pneumoniae were induced to competence as has been described in Yother et al., 1986, incorporated herein by reference. Non-encapsulated strains were made competent for transformation by growth in Todd Hewitt broth (Difco, Detroit, Mich.) supplemented with 0.01% CaCl$_2$, 0.5% BSA, and 0.5% yeast extract. S. pneumoniae cells were allowed to express transforming DNA for 2 h. before plating on agar medium. Electroporation of H$_2$O washed E. coli LE392 cells resuspended in 10% glycerol was performed in a BTX Electro Cell Manipulator 600 according to the instructions of the manufacturer (Biotechnologies and Experimental Research, Inc., San Diego, Calif.).

5. Preparation of S. pneumoniae chromosomal DNA

Cultures of S. pneumoniae (100 ml) were grown to stationary phase in the presence of 1% choline chloride to prevent autolysis (Briese and Hakenbeck, 1983). The bacteria were centrifuged at 5000 rpm for 10 min and resuspended in 2.5 ml TE buffer (10 mM TrisHCl, 1 mM EDTA, pH 8.0). SDS was added to 1%, and the cells were lysed at 65° C. for 15 min. One fifth volume 5 M KOAc (pH 8) was added, and incubation was continued at 65° C. 15 min, followed by incubation on ice for 60 min. Cell debris was removed by centrifugation at 10,000 rpm for 10 min, the supernatant was added to 2 volumes of ethanol, and the DNA was hooked out with a glass rod. The DNA was dried, resuspended in TE, and further purified by CsCl/ethidium bromide buoyant density gradient centrifugation (Radloff et al., 1967).

6. Recovery of plasmids resolved from S. pneumoniae chromosomes.

A 10 ml culture of late log phase S. pneumoniae was centrifuged at 5000 rpm for 10 min. The supernatant was removed, and the cells were resuspended in 100 μl lysis buffer (Saunders and Guild, 1980). Following a 5 min incubation at 37° C., 900 μl of Birnboim and Doly solution I was added, and the rest of the alkaline lysis procedure was carried out as for E. coli (Birnboim and Doly, 1979). The resulting preparation contained very little plasmid DNA and was therefore electroporated into E. coli where significant quantities of plasmid could be obtained and isolated as described (Birnboim and Doly, 1979).

7. Mapping by chromosomal transformation

The integration frequency was used to determine the linkage of spontaneous mutations. Chromosomal DNA from a streptomycin resistant derivative of the capsule mutant was used to transform the other mutants. The number of encapsulated transformants obtained divided by the number of streptomycin resistant transformants obtained is defined as the integration frequency (Bernheimer and Wermundsen, 1972). Integration frequencies of 0.02 to 0.03 resulted from crosses between mutants carrying mutations in the same locus. Integration frequencies of about 0.3 indicated the mutations were in different loci.

Linkage of plasmid insertions to capsule mutations was determined by using chromosomal DNA from wild type strains carrying non-destructive plasmid insertions to transform capsule mutants. Transformants were selected on erythromycin and screened for encapsulation. The co-transformation frequency determined the degree of linkage.

8. Capsule detection by ELISA

To obtain a crude capsule extract, a 10 ml culture of log phase S. pneumoniae cells was centrifuged at 5000 rpm for 20 min, and the supernatant was removed. The pellet was resuspended in 1 ml PBS (50 mM sodium phosphate pH 7.4, 100 mM NaCl). Protein content was determined on 100 μl of washed cells using the Bio-Rad kit (Bio-Rad, Richmond, Calif.). The remaining cells were extracted with an equal volume of 24:1 chloroform/isoamyl alcohol. Following centrifugation, the aqueous phase was precipitated with two volumes of ethanol. The precipitate was resuspended in 1 ml PBS, then treated with RNase at 1 mg/ml and DNase at 0.2 mg/ml for 3 h at 37° C., and pronase at 1 mg/ml for 2 h at 37° C. The extract was then re-extracted and precipitated as before. The precipitate was resuspended in PBS and used to coat the wells of a microtiter plate for ELISA analysis. Values were normalized to protein content. ELISAs were performed by the standard technique (Ausubel et al., 1987). Monoclonal antibody 16.3 was used to detect type 3 capsular polysaccharide (Briles et al., 1981a). ELISA plates were read at 405 nm in a Biotek model 320 plate reader (Bio-Tek Instruments, Winooski, Vt.).

9. Percoll gradient centrifugation

For density determinations, 10 ml of log phase cells were centrifuged at 4000 rpm for 10 min, washed once with water, and then resuspended in 1 ml water. A volume of 300 µl of cells was loaded on top of a 10 ml 0–100 or 25–100% continuous Percoll gradient. Gradient density marker beads were loaded on top of the gradients. The gradients were centrifuged at 10,000 rpm for 15 min with the brake off. Percoll and density marker beads were purchased from Pharmacia (Piscataway, N.J.). Non-encapsulated strains of *S. pneumoniae* exhibit a higher density in Percoll gradients than encapsulated strains (Briles et al., 1992). Percoll gradients were also used to enrich for encapsulated cells expected to result from low frequency events. Percoll gradients were used to obtain binary capsule type transformants and to enrich for spontaneous revertants to capsule production.

B. Results

To identify the type 3 capsule region of *S. pneumoniae*, a Sau3AI library of fragments was cloned from the type 3 encapsulated strain WU2 to direct insertions into the chromosome of strain WU2. The library used in the insertion-duplication mutagenesis procedure was constructed by cloning random Sau3AI fragments in the plasmid pJY4163, which carries an erythromycin-resistance marker. Since this plasmid is unable to replicate in *S. pneumoniae*, all erythromycin-resistant transformants should contain insertions at the chromosomal site of the target Sau3AI fragment (Morrison et al., 1984). By transforming the library of clones into strain WU2, the inventors obtained 5 non-mucoid isolates among 491 erythromycin-resistant transformants. However, further studies involving transformation of the parent strain with either chromosomal DNA from the mutants or plasmids recovered from the mutants showed that the plasmid insertions were neither linked to nor responsible for the capsule mutations.

Figure 1:
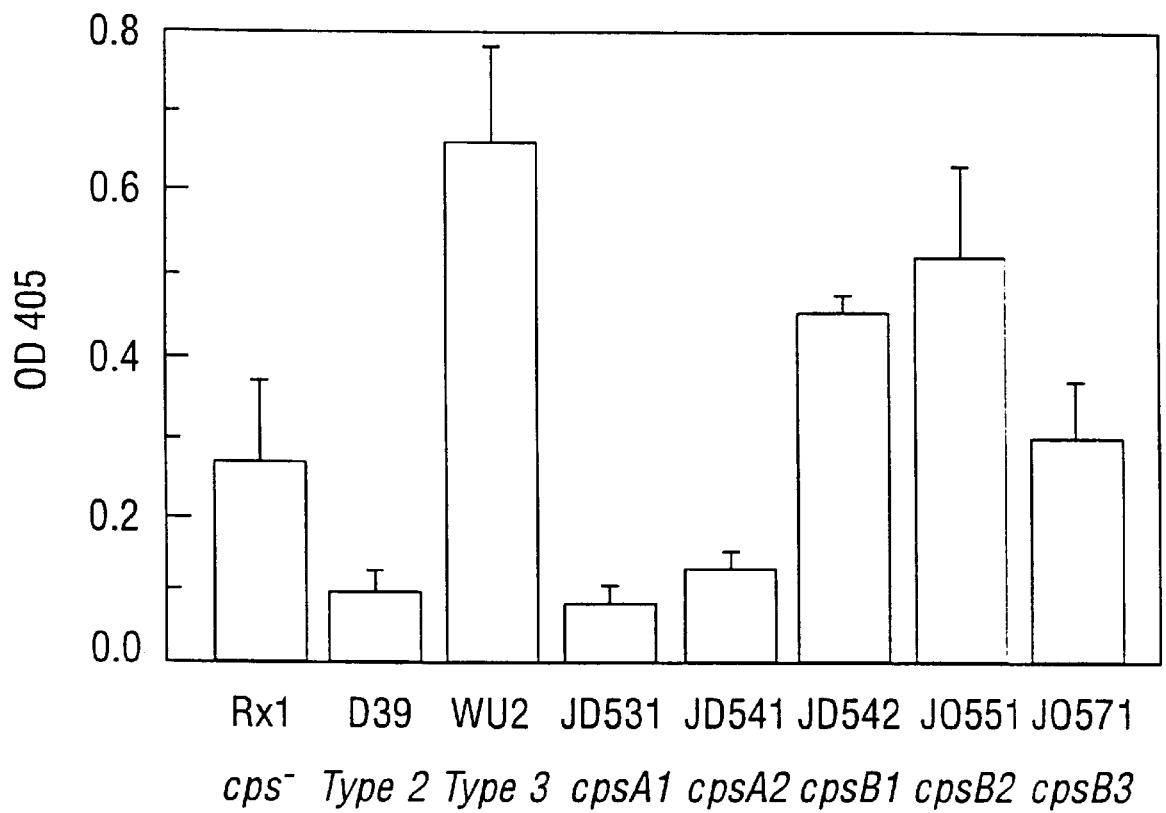
FIG. 1. ELISA for the detection of type 3 capsule. Wells of microtiter dishes were coated with crude extracts of capsule material. Type 3 capsule was detected with the monoclonal antibody 16.3 (Briles et al., 1981a). The type 2 strain D39 served as a negative control. Measurements were made in triplicate, and error bars represent standard errors. Values were standardized to protein content. Genotypic designations were based on linkage as determined by transformation mapping.

To determine if the non-mucoid isolates were truly deficient in the production of type 3 capsular polysaccharide, several methods were employed. In slide-agglutination assays, none of the five mutants reacted with polyclonal antisera specific for type 3 polysaccharide. Centrifugation through Percoll density gradients revealed that the mutant strains were much denser than the encapsulated parent strain. WU2 cells had a density <1.01 g/ml, whereas all five mutants migrated at 1.09 to 1.10 g/ml. These data suggested that complete capsules were not produced by the mutants. However, these tests might not reveal the presence of short or sparse polysaccharide chains on the cell surfaces or capsular material not translocated to the surfaces. To determine if such material was present, ELISA analysis was carried out on crude cell extracts. Capsular material in the extracts was detected using a monoclonal antibody directed against type 3 polysaccharide. The analysis indicated that mutants JD531 and JD541 (designated mutants A1 and A2 respectively) made no detectable capsular material, whereas mutants JD542, JD551, and JD571 (designated mutants B1, B2 and B3 respectively) made significant levels of reactive material. The common laboratory strain Rx1 was also found to produce significant levels of type 3 capsular material (FIG. 1). Although Rx1 is generally referred to as a non-encapsulated derivative of the type 2 strain D39, it was transformed three times with chromosomal DNA from derivatives of the type 3 strain A66, chosen twice for type 3 encapsulation, and chosen finally for non-encapsulation (Ravin, 1959; Shoemaker and Guild, 1974).

No capsular material could be detected by ELISA in the culture supernatant fluids of mutants JD531 and JD541, indicating that these mutants were not merely defective in attachment of the polysaccharide. Only low levels of capsular material were detected in supernatants of Rx1, JD542, JD551, and JD571 cultures.

The five mutations resulting in the capsule-deficient phenotype were mapped to two loci by chromosomal transformation. Reciprocal crosses between the mutants yielded encapsulated transformants for each combination, but not for transformation of a mutant with DNA from the same strain. The mutations were thereby determined to be genotypically distinct. The transformations also revealed that the mutations in JD531 and JD541 were more closely linked to each other than to the mutations in JD542, JD551, and JD571. Likewise, the mutations in JD542, JD551, and JD571 were more closely linked to one another than to the other two mutations. The integration frequencies for those mutations judged to be closely linked were similar (0.02 to 0.03) and were ten-fold lower than those judged to be not as closely linked. The genotypic data thus agreed with the phenotypic data, i.e., the two mutations leading to total loss of capsule synthesis mapped together, and the three mutations causing lack of proper capsular polysaccharide processing mapped together. The loci containing these mutations were temporarily designated cpsA and cpsB, respectively, and the mutations were named as indicated in FIG. 1.

Table 4 shows the transformation frequencies of capsule mutations. *S. pneumoniae* strains were transformed with chromosomal DNA from strain JD636, a streptomycin resistant WU2 (Table 3), and streptomycin-resistant transformants were selected. Transformation frequencies are calculated from cultures not induced to competence. With optimal induction, strain WU2 may exhibit a transformation frequency approaching that of the non-encapsulated mutants. However, during the mutagenesis procedure, sub-optimal transformation frequencies were observed (0.0003 to 0.006%). JD908 (Table 3) was also included, it contains an insertion mutation resulting in loss of capsule expression (described in FIG. 4). It would appear that the non-encapsulated mutants are highly transformable, suggesting that the reason for their over-representation in the original transformant population was because of their transformability. The mutagenesis procedure, by selecting for transformability, has enriched for mutants already deficient in capsule (Table 4).

TABLE 4

Transformation frequencies of capsule mutants.

| Recipient | Mutation | Total cfu | $Str_R$ cfu[b] | Transformation frequency (%) |
|---|---|---|---|---|
| JD531 | cpsA1 | $2.0 \times 10^5$ | $5.0 \times 10^2$ | 0.3 |
| JD541 | cpsA2 | $1.4 \times 10^8$ | $7.6 \times 10^2$ | 0.6 |
| JD542 | cpsB1 | $2.4 \times 10^5$ | $20 \times 10^2$ | 0.8 |
| JD551 | cpsB2 | $2.0 \times 10^5$ | $4.6 \times 10^2$ | 0.2 |
| JD571 | cpsB3 | $2.4 \times 10^8$ | $5.0 \times 10^2$ | 0.2 |
| WU2 | wt | $0.0 \times 10^5$ | 1 | 0.0000 |
| JD908 | cpss | $10 \times 10^5$ | $10 \times 10^2$ | 0.1 |

[b]$Str^R$ streptomycin resistant.

EXAMPLE 2

Identification of a Clone Containinc a Capsule Gene

Figure 2:
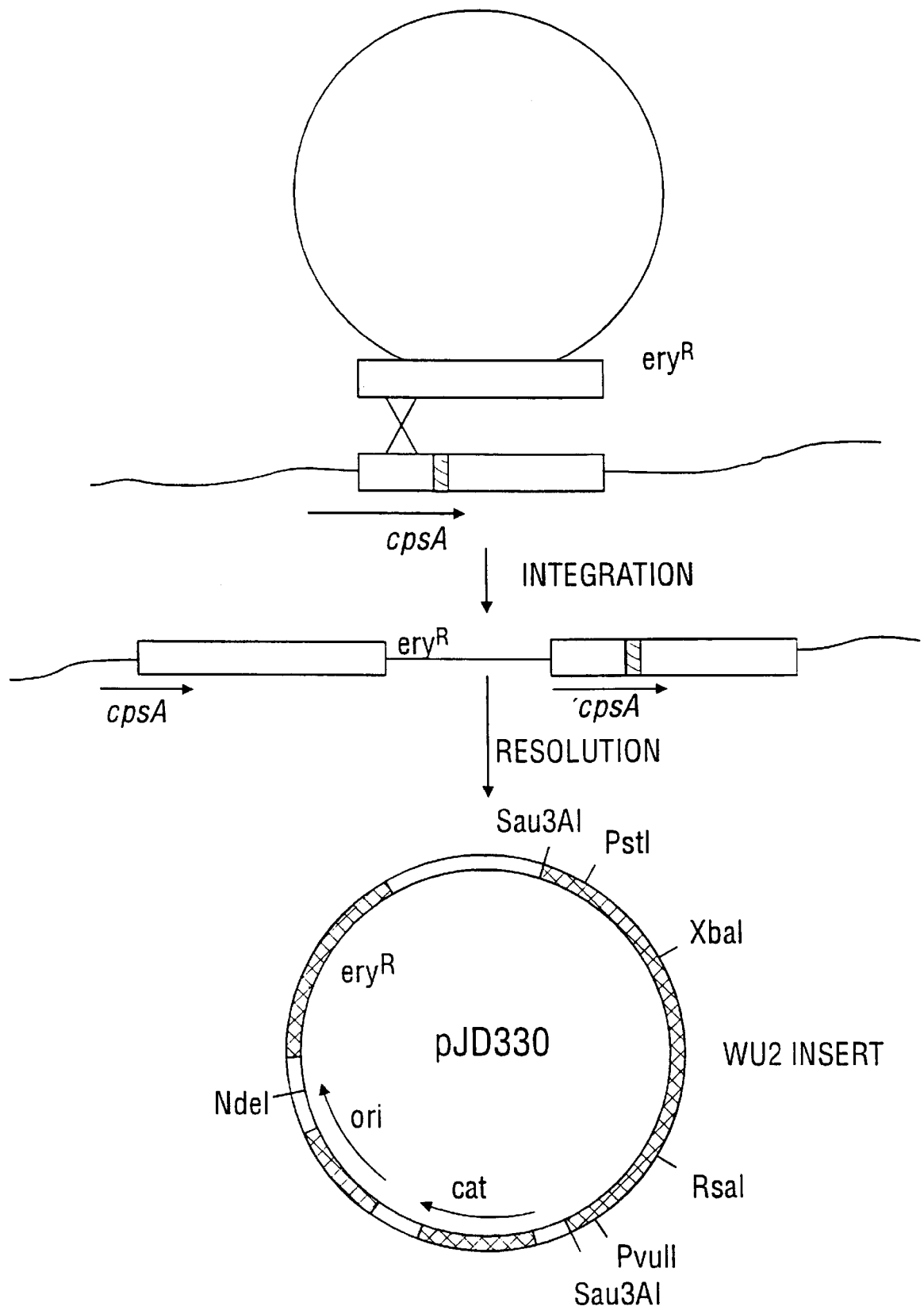
FIG. 2. Insertion-duplication restoration. The cloned fragment and the homologous fragment in the chromosome are represented by the open boxed regions. The dark block represents the mutation in the chromosome of the mutant strain. Insertion of the plasmid clone into the pneumococcal chromosome results in a duplication of the homologous fragment with the plasmid inserted in between. If the recombination occurs to the left of the mutation as shown here, a wild type, full-length copy of the gene is created and function is restored. The plasmid clone leading to restoration spontaneously excises at low frequency through homologous recombination and can therefore be easily recovered by transformation to *E. coli*. pJD330 contains a 2.4 kb Sau3AI fragment.

To identify DNA fragments capable of repairing the cpsA1 mutation, JD611, a derivative of JD531 lacking the pJY4163 insertion, was transformed with pools of pJY4163 clones containing Sau3AI fragments from strain WU2. Transformations and DNA manipulations were performed as described in Example 1. In this insertion-duplication restoration procedure, the plasmid clone is inserted into the mutant chromosome, leading to duplication of the homologous target fragment and restoration of one wild type copy of cpsA (FIG. 2). Erythromycin-resistant transformants were screened visually for the mucoid phenotype. One plasmid clone was identified which restored encapsulation in the cpsA1-containing mutant. Due to the duplication of the target fragment, the plasmid insertion could resolve out of the chromosome by homologous recombination at low frequency. Therefore, transformation of E. coli with DNA from the encapsulated transformant and selection for erythromycin-resistance allowed recovery of the plasmid, designated pJD330, that had repaired the cpsA1 defect.

Transformation of the capsule-deficient mutants with pJD330 suggested that the clone contained part of cpsA. When pJD330 was inserted into the chromosome of the cpsA1-containing mutant, 56% of the erythromycin-resistant transformants became encapsulated (Table 5). The failure of the remainder of the transformants to become encapsulated indicated that the cloned fragment contained only one end of the gene. The site of the crossover relative to the site of the mutation determines whether the mutation will be located in the incomplete copy of the gene or the full-length copy. If the recombination occurs on the left, as shown in FIG. 2, the full-length gene is wild type and capsule is restored. However, if the crossover occurs on the right, the mutation is located in the full-length copy, and no capsule is obtained. This interpretation is supported by the observation that transformants of the cpsA1 mutant which incorporated the plasmid but did not become encapsulated, spontaneously gave rise to encapsulated, erythromycin-resistant colonies, either by excision and reinsertion of the plasmid or by gene conversion. The cpsA2 defect was not repaired by pJD330, suggesting that the site of this mutation was either not present on the plasmid clone or was located too near the end of the clone for crossover to repair the defect.

TABLE 5

Restoration of encapsulation with pJD330.[a]

| Recipient | Mutation | Ery[R] cfu[b] | Cps[+] cfu | Cps[+] frequency (%) |
|---|---|---|---|---|
| JD611 | cpsA1 | 475 | 267 | 56 |
| JD619 | cpsA2 | 26 | 0 | 0 |
| JD692 | cpsB1 | 13 | 0 | 0 |
| JD614 | cpsB2 | 124 | 0 | 0 |
| Rx1 | cps⁻ | 158 | 49 | 31 |
| 661 | capD6 | 56 | 0 | 0 |
| A66R2 | capD4 | 4 | 3 | 75 |

[a]Mutants deficient in capsule production were transformed with pJD330 DNA. Transformants were plated on erythromycin to select for those containing chromosomal insertions of pJD330. Erythromycin-resistant transformants were screened for mucoldy. Cps[+] frequency is the ratio of Cps[+]/Ery[R] cfu.
[b]Ery[R]. Erythromycin resistant.

Transformation of pJD330 into the cpsB-containing mutants did not restore any of these to encapsulation, suggesting that cpsB is not present on pJD330. However, strain Rx1 was restored to type 3 encapsulation by pJD330 (Table 5).

EXAMPLE 3 cpsA Codes for UDP-Glucose Dehydrogenase

Transformation of two previously characterized mutants suggested that pJD330 contains part of the gene for UDP-glucose dehydrogenase. UDPG dehydrogenase is the enzyme which converts UDP-glucose (UDPG) into UDP-glucuronic acid (UDPGA). UDPG and UDPGA are the two nucleotide sugars which are required for type 3 capsule synthesis (Smith et al., 1960). The non-encapsulated mutants A66R$_2$ and 661 were previously shown to be deficient in the production of UDPG dehydrogenase due to mutations in the locus designated capD (Bernheimer and Wermundsen, 1972). Transformation of A66R$_2$ (capD4) with pJD330 restored encapsulation, whereas transformation of 661 (capD6) did not (Table 5).

Transformations with chromosomal DNA (Table 6) confirmed that the other cpsA and capD mutations were closely linked to the region cloned in pJD330. Transformations and other DNA manipulations were performed as described in Example 1. Strain JD770 was obtained by inserting pJD330 into the chromosome of the parental strain WU2. JD770 was found to produce wild type amounts of type 3 capsule. Chromosomal DNA from JD770 was used to transform those mutants which could not be restored to encapsulation by pJD330 (Table 6). The cpsA2 and UDPG dehydrogenase mutation capD6 were found to be >90% linked to the plasmid insertion.

TABLE 6

Restoration of encapsulation with chromosomal DNA linked to pJD330 insertion.[a]

| Recipient | Mutation | Ery[R] cfu[b] | Cps[+] cfu | Cps[+] frequency (%) |
|---|---|---|---|---|
| JD692 | cpsB1 | 17 | 13 | 70 |
| JD614 | cpsB2 | 79 | 58 | 73 |
| JD619 | cpsA2 | 42 | 39 | 93 |
| 661 | capD6 | 6 | 6 | 100 |

[a]Transformants were plated on erythromycin to select for those which had incorporated the region containing the insertion. Erythromycin-resistant transformants were screened for mucoldy. Cps[+] frequency is the ratio of Cps[+]/Ery[R] cfu.
[b]Ery[R] -- erythromycin resistant.

Deletion analysis was performed to more closely localize the sites of the mutations cpsA1, capD4, and the mutation in Rx1 (cps−). By transforming with plasmid subclones and making no selection for insertion of the plasmids, the inventors were able to observe recombination events that occurred as a result of double crossovers between the cloned fragment and its homolog in the chromosome (FIG. 3A). Transformations with several subclones revealed that the sites of the mutations could all be localized to a 250 bp PvuII-SspI fragment common to pJD380 and pJD369 (FIG. 3B). The fact that the same fragment which restores encapsulation in a UDPG dehydrogenase mutant also restores encapsulation in the cpsA1—containing mutant suggests that cpsA encodes UDPG dehydrogenase. From here on, the cpsA loci is designated cps3D (see Example 9).

It is known that transformation of UDPG dehydrogenase mutants, including 661, with chromosomal DNA from a type 1 strain restored type 3 encapsulation by incorporation of the type 1 specific genes at a site other than that occupied by the type 3 genes (Bernheimer et al., 1967, Bernheimer and Wermundsen, 1972). Type 1 capsular polysaccharide contains galacturonic acid; therefore, type 1 strains are expected to produce UDPG dehydrogenase (Austrian et al., 1959).

When UDPG dehydrogenase mutants of a type 3 strain were transformed with DNA from type 1 strains, the UDPG dehydrogenase from type 1 complemented the type 3 mutation, allowing the production of both capsular polysaccharides. The UDPG dehydrogenase gene from the type 1 strain was never observed to repair the mutation in the type 3 gene (Bernheimer and Wermundsen, 1969). When the cpsA1 mutant JD611 was transformed with chromosomal DNA from a type 1 strain, type 3 encapsulated transformants were obtained at a frequency of $3 \times 10^{-6}$. This frequency is in agreement with that observed for transformation of mutant 661 (capD6) to binary encapsulation (Bernheimer and Wermundsen, 1972) and above the spontaneous reversion frequency ($<8 \times 10^{-9}$).

EXAMPLE 4

Genetic and Physical Map of the Type 3 Capsule Region

A. Methods

1. Southern Blotting

Southern blotting was performed using the vacuum blotter and chemiluminescent detection system purchased from Stratagene (La Jolla, Calif.). The PosiBlot® 30-30 pressure blotter is part of an integrated system designed to transfer DNA or RNA from agarose gels quickly and efficiently onto solid support matrices, such as Stratagene's hybridization membranes including the Nitrocellulose membranes, Duralose-UV™ membranes (reinforced nitrocellulose), Duralon-UV™ membranes (nylon) or Illuminator™ nylon membranes.

Following electrophoresis the gels are stained in 5 $\mu$g/ml of ethidium bromide (EtBr) in water, destained in water and then photographed. Prior to Southern transfer, the gels are pretreated by depurination, denaturation and neutralization. Depurination entails treating the gels with 0.25 N HCl for 5–30 minutes with gentle shaking. Denaturation consist of pouring off the HCl and adding a 0.5 N NaOH and 1.5 M NaCl denaturation solution, enough to cover the gel. The gels are treated for 5 minutes to one hour with gentle shaking. Neutralization involves pouring off the denaturation solution and adding a 0.1 M Tris-HCl (pH 7.5) and 1.5 M NaCl neutralization solution, enough to cover the gel. They are then treated for 5 minutes to one hour with gentle shaking.

Gels are then ready for blotting, which is performed with gloved hands. The membrane is prewet in distilled water (dH$_2$O) and then in transfer buffer for 5 minutes. 10x SSC buffer-10x SSPE buffer or 25 mM sodium phosphate (pH 6.5) is the transfer buffer for nylon membranes. For nitrocellulose or Duralose-UV membranes, 20x SSC buffer should be used.

The membrane and gel are set up in the Posiblot 30-30 pressure blotter and pressure exerted and adjust to 75 mm Hg. Blotting times vary for different gels and depend on the amount and size of the nucleic acid; size, thickness and percentage of gel; and depth of gel wells and volume of sample loaded on the gel; which are routinely optimized. After the allotted blotting time, the position of the wells on the membrane is marked and the gel removed. The gel is generally stained and destained in ethidium bromide to check the efficiency of transfer. The membrane is removed from the device and placed on clean Whatman 3MM paper to allow the excess buffer to be absorbed. Once the membrane is free of standing liquid, but still damp, the membrane and the Whatman 3MM paper is placed under a UV light and crosslinked. Alternatively, dry the membrane in a 80° C. drying oven for 1–2 hours prior to crosslinking.

Boehringer Mannheim's Genius™ Nonradioactive Detection System, a chemiluminescence-based, nucleic acid detection kit, permits fast, safe and sensitive detection of DNA and RNA immobilized on nylon membranes. As little as 0.1 pg of target plasmid DNA can be detected in a 30-minute exposure of the processed blot to X-ray film or, in a similar exposure time, 1 pg of a single-copy gene can be detected in less than 1.0 $\mu$g of genomic DNA. The Nonradioactive Detection System can also be used for rapid Northern-blot analysis of RNA.

After transfer and crosslinking, the membrane is prehybridized for 1 hour at 42° C. The labeled probe is placed in a microfuge tube containing 100 $\mu$l of sonicated salmon sperm DNA (10 mg/ml) stock and heated in a boiling water bath for 5 minutes. This is pulse-spun to collect condensation and stored on ice until ready to add to hybridization. The probe is added to prehybridization solution and hybridized, with shaking, overnight at 42° C. using standard hybridization solutions as described by the Genius® protocol. This is washed once for 15 minutes at room temperature in 0.1x SSC/0.% SDS and then washed twice for 15 minutes at 60° C. in 0.1x SSC/0.1% SDS for each wash. The probe is then ready for detection. The BRL 1 Kb DNA ladder was used as a molecular weight size standard (Bethesda Research Laboratories, Gaithersburg, Md.). Biotin labeled probes for hybridization were prepared by nick-translation using the BRL BioNick kit (Bethesda Research Laboratories). High stringency conditions, as described above should result in the detection of sequences $\geq 95\%$ homologous to the probe. Reduced stringency was achieved by lowering the wash, or hybridization and wash temperatures to room temperature. At reduced stringency, sequences with 85% homology to the probe should have been detectable.

B. Results

Figure 4:
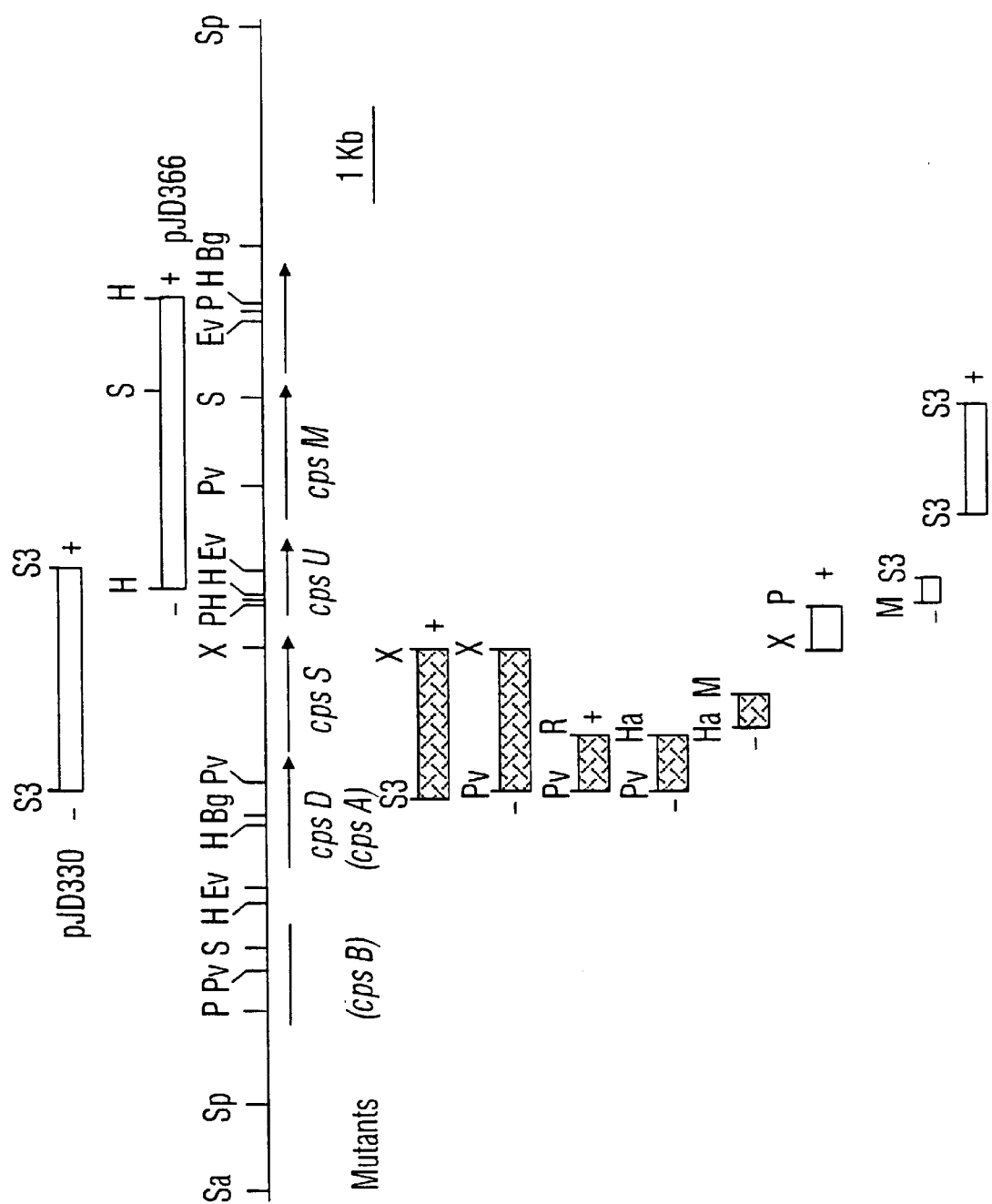
FIG. 4. Physical and genetic map of the type 3 capsule region of *S. pneumoniae* WU2. The restriction map was developed by probing chromosomal digests of WU2 with pJD330 and pJD366 and by probing chromosomal digests of JD770 with pJD330 and pJY4163. The location of primary clones pJD330 and pJD366 are indicated above the map. Subcloned fragments used to target insertion-duplication mutations are indicated below the map. Insertion of plasmids containing shaded fragments led to loss of capsule production. + or − at the end of a fragment indicates the presence or absence of transcription detected at that point in the chromosome. Insertions of pJD330 and pJD366 are in the orientation to detect transcription to the left. Clones pJD351 and pJD364, which contain the pJD330 and pJD366 fragments, respectively, in the opposite orientation, were also used for the transcription studies. The other plasmids used for insertions were pJD356, pJD337, pJD369, pJD359, pJD362, pJD361, pJD357, and pJD374, in the order shown. The genes indicated by genetic data or suggested by transcription determinations were drawn based on preliminary sequence information. The cpsDSUM designations are based on probable functions, as described in the text. Restriction sites are Bg, BglII; Ev, EcoRV; H, HindIII; Ha, HaeIII; M, MunI; P, PstI; Pv, PvuII; R, RsaI; S, SacI; S3, Sau3AI; Sa, SalI; Sp, SphI; X, XbaI. Restriction sites are not necessarily unique to the entire region.

Using pJD330 as a probe in Southern hybridizations, a physical map of the type 3 capsule region of strain WU2 was developed (FIG. 4). Using the information gained from the chromosomal mapping, the inventors identified and cloned the HindIII fragment located to the right of the pJD330 insert. HindIII fragments approximately 3 kb in size were cloned from the WU2 chromosome into pJY4164. By using pJD330 to screen for homology, a clone containing a 3.2 kb insert was identified. This clone, pJD366, was then used to determine the location of the cpsB mutants.

Transformation mapping using JD770 showed that the cpsB mutations were about 74% linked to the pJD330 insertion (Table 6). This high frequency indicated that cpsB might be adjacent to the fragment contained in pJD330. When pJD366 was used to transform strains containing the cpaB mutations, encapsulation was not restored. Insertion of pJD366 into the WU2 chromosome did not alter the production of type 3 capsule; therefore, the inventors were able to examine linkage of the insertion to the cpsB mutations and determine the relative location of cpsB. The pJD366 insertion was found to be only 25% linked to the cpsB mutations (as compared to 74% for the pJD330 insertion), suggesting that cpsB is located to the left of the pJD330 insert, as shown in FIG. 4.

In order to localize regions necessary for capsule production, insertion mutations using subclones of pJD330 and pJD366 were made. Transformation of strain WU2 with plasmids containing fragments internal to a gene or operon required for capsule production should result in loss of encapsulation. Insertion of the plasmid containing the Sau3AI - XbaI fragment resulted in loss of encapsulation, indicating that this entire 1.6 kb fragment is within a single gene or operon required for capsule synthesis. Likewise, all insertions within this region eliminated capsule production (FIG. 4). Insertion of the plasmid containing the XbaI-PstI fragment did not disrupt capsule production, indicating that the end of the gene or operon is contained within this fragment. None of the other insertions resulted in loss of capsule, indicating they were not internal to genes or operons required for capsule synthesis.

Since the plasmids used for the chromosomal insertions contain a promoterless cat gene, the inventors were able to establish the directions of transcription at the insertion sites. All insertions which contained the cat gene in the orientation to detect transcription proceeding to the right (as drawn in FIG. 4) resulted in chloramphenicol resistance. No transcription was detected in the opposite direction (FIG. 4).

EXAMPLE 5

Homology with Other Capsule Types

If the type-specific genes for capsule production are contained within a cassette, as has been proposed, these genes should show little homology to the type-specific genes from other capsule types. A high degree of homology should exist in the regions flanking the type-specific region (Austrian et al., 1959; Bernheimer and Wermundsen, 1972). The flanking regions may contain common genes necessary for production of capsule of any type or might not be involved in capsule production.

To determine if the regions cloned in pJD330 and pJD366 are specific to type 3 or are present in strains of other capsule types, HindIII digested chromosomal DNAs from strains of types 2, 3, 5, 6A, 8, 9, and 22 were Southern blotted and probed with these plasmids or fragments thereof. The fragment contained in pJD330 (the probe used was pJD351, containing 2.4 kb Sau3A1 fragment from pJD330) hybridized only with DNA from the type 3 strain, detecting the expected bands at 2.2 and 3.2 kb. No hybridization with the chromosomal DNA of the other six serotypes was detected, nor could the stringency be sufficiently lowered to detect homology in these strains.

When HindIII digests of chromosomal DNAs from these same strains were probed with the HindIII fragment from pJD366, the expected 3.2 kb band was observed in the type 3 strain, but a 1.1 kb band was found in every other capsule type. Probing with subclones of pJD366 containing the 2.1 kb HindIII-SacI fragment or the 1.2 kb SacI-HindIII fragment revealed that the homology resided in the more distal 1.2 kb fragment. Therefore, unlike the remaining 4.2 kb of DNA, which could be detected only in the type 3 strains, the 1.2 kb SacI-HindIII fragment (pJD377) showed a high degree of homology and could be detected at high stringency in all strains (2, 3, 5, 6A, 8, 9 and 22). This result suggests that this region may be the highly homologous flanking DNA predicted by the model to be adjacent to the type-specific genes.

EXAMPLE 6

Transformation of Capsule Type

To determine if all the type-specific genes necessary for the production of type 3 capsular polysaccharide were closely linked on the pneumococcal chromosome, strain JD770 was used as a donor in transformation of the type 2 strain D39. Laboratory techniques were as described in Example 1. Seventy-three erythromycin-resistant transformants were obtained, and all 73 expressed type 3 capsule. No type 2 capsule could be detected by agglutination with type 2 specific antisera. Using chromosomal DNA from strain JD770, succesful transformation of strains of type 5 and type 6B to type 3 encapsulation was also perfomed (Example 18).

By transforming the type 2 strain D39 with pJD366, isolates were obtained with the erythromycin-resistance marker closely linked to the type 2 capsule genes. These transformants were the result of recombination between the flanking regions of homologous non-type-specific DNA. Using DNA from one of these isolates, JD871, to transform the type 3 strain WU2 resulted in 95% co-transformation of type 2 encapsulation with erythromycin resistance. The remaining 5% were found to be type 3 encapsulated, indicating that only the flanking DNA or the plasmid alone was transferred to these isolates. Insertion of pJD366 into the type 5 strain DBL5 also resulted in a strain—JD875—with the erythromycin resistance marker linked to the type-specific genes. This strain was successfully used to transform WU2 to type 5 encapsulation.

EXAMPLE 7

Direct Test of the Cassette Model

Transformations and other DNA manipulations were performed as described in Example 1. Southern Blotting was performed as described in Example 4.

Figure 5:
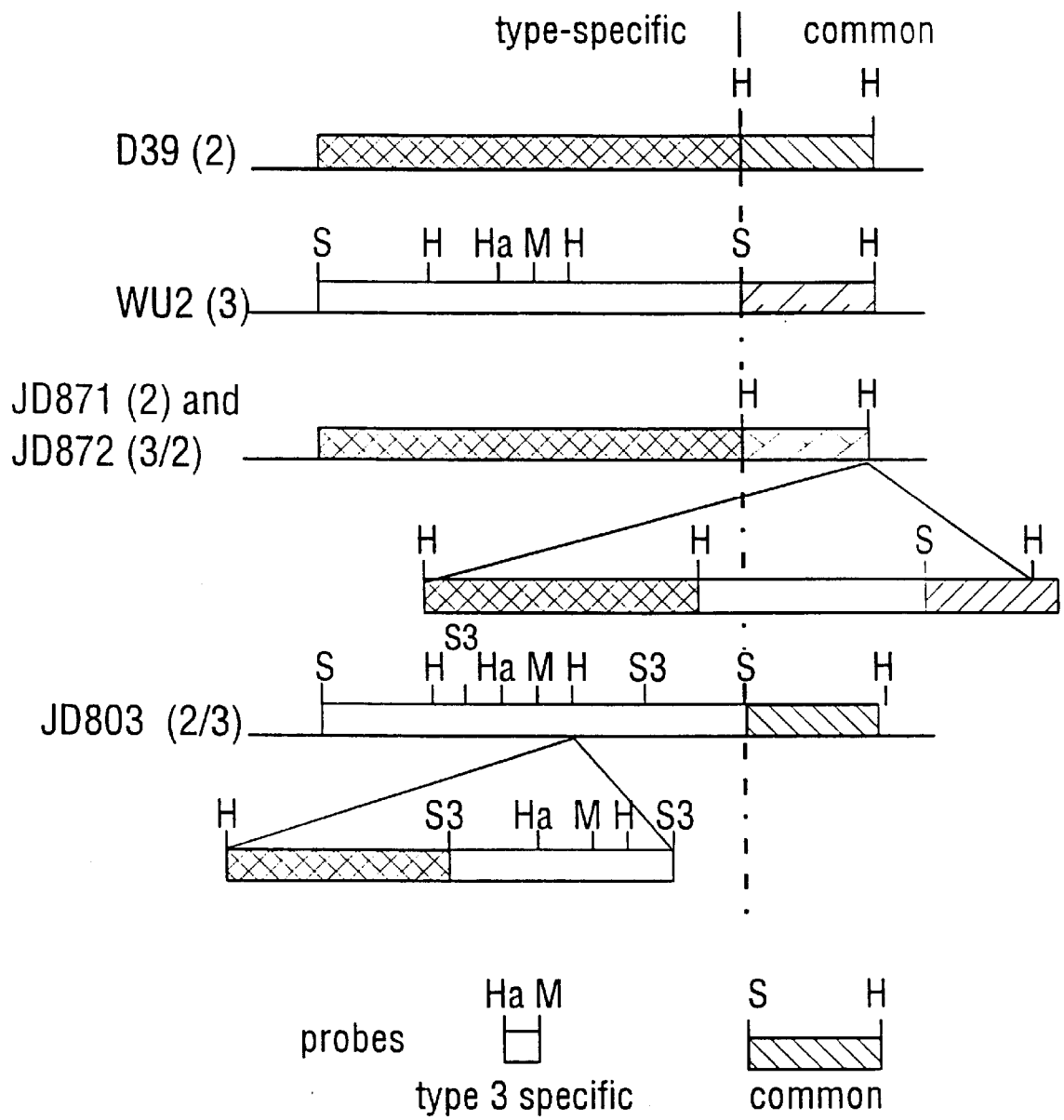
FIG. 5. Schematic representation of the capsule regions in these strains. Insertions in JD871 and JD872 result from incorporation of pJD366. The insertion in JD803 is pJD330. The shaded square symbol represents type 2 specific DNA; the open square symbol represents type 3 specific DNA; the hatched square symbol represents flanking DNA common to both type 2 and type 3 and; the black square symbol represents pJY4163 or pJY4164. The locations of the probes used are indicated below the map.

If capsule type change involves a cassette-type recombination mechanism, then transformation of capsule type should result in replacement of the recipient's type-specific genes by those of the donor. In order to determine if such replacement does occur, DNA was used from the type 3-specific region to probe HindIII digested chromosomal DNA from a strain which was originally type 2 and was transformed to type 3 (JD803), and a strain which was originally type 3 and was transformed to type 2 (JD872) (FIG. 5).

Hind III digested chromosomal DNA from strain: 2 (D39 and JD871 from Example 6); 3 (WU2); 3/2 (JD872) and; 2/3 (JD803), were used in Southern blotting. First of all the Southern blot was probed with pJD343 and pJD368 Together these plasmids contain an 800 bp region (HaeIII-MunI) specific to type 3 and internal to cpsS (FIG. 5). The type 3 parent WU2 contained the expected 2.4 kb HindIII fragment specific to type 3, whereas neither the type 2 parent D39 nor its derivative JD871, which has pJD366 inserted into the chromosome, contained this fragment. When JD871 (type 2) was used to transform WU2, the resulting strain JD872 was type 2 encapsulated and had lost the 2.4 kb type 3-specific fragment. Similarly, when D39 was transformed with DNA from JD770 (type 3), the resulting strain JD803 was type 3 encapsulated and had gained the type 3-specific fragment.

Reprobing of the same blot with the 1.2 kb SacI-HindIII fragment common to all capsule types (pJD377), revealed that the 1.1 kb HindIII fragment was present in each of the strains that now produced the type 2 capsule. Further, JD803 had also gained the 3.2 kb HindIII fragment present in WU2 (type 3), 2.1 kb of which is type 3-specific. This fragment was also present in JD871 and JD872 since it is contained in the plasmid insert (FIG. 5).

The loss of type 3 genes by the strain converted to type 2 encapsulation indicated that capsule type change does not occur by addition, but rather by replacement of the type-specific genes.

EXAMPLE 8

The DNA Secuence and Amino Acid Sequence of cps3D.

A. Methods

1. DNA Sequencing

Templates for sequencing were prepared from double-stranded plasmid DNA by denaturing with NaOH (2 N) for 5 min at room temperature, and precipitating with 5 M NH$_4$OAc and ethanol. DNA was sequenced by the Sanger dideoxy method using the Sequenase 2.0 kit (U.S. Biochemicals, Cleveland, Ohio) and $^{35}$S-dATP. The oligonucleotide primers 5'-GCCACTATCGACTACGCG-3' (SEQ ID NO:17) and 5'TCATTTGATATGCCTCCG-3' (SEQ ID NO:18), corresponding to bases 308 to 325 and 445 to 428 of the cloning vectors pJY4163 and pJY4164 (Yother, et al., 1992), respectively, were used routinely. Primers 5'-GTGAGATAAATAGTAGTGCG-3' (SEQ ID NO:19) and 5'-TCCAGCTCGTGTCATAATCT-3' (SEQ ID NO:20), corresponding to bases 3474 to 3493 and 3596 to 3577, respectively, of the type 3 capsule locus (FIG. 6G) were also used. All oligonucleotide primers were purchased from Oligos, etc. (Wilsonville, Oreg.). DNA sequencing of PCR products was performed using the U.S. Biochem PCR product sequencing kit, according to the directions of the manufacturer. PCR products were sequenced at least twice, from separate amplification reactions. Greater than 97% of the sequence was obtained for each strand.

2. Sequence analysis

The University of Wisconsin Genetics Computer Group programs (Genetics Computer Group, 1991) were used in the analysis of the DNA sequence. Database searches were performed using the TFASTA program to detect homology with the deduced amino acid sequences. Potential sigma-70 type promoter sequences were located by using the FIND program to search for sequences with six or less mismatches, as compared to the consensus sigma-70 promoter sequence (Mulligan and McClure, 1986), and having a spacing of 15 to 20 bp between the −35 and −10 hexamers. Potential promoter sequences were evaluated using the equations of Harr et al. (Harr, et al., 1983). The sequence presented in FIG. 6D through FIG. 6J (SEQ ID NO4, SEQ ID NO:5 and SEQ ID NO:6) has been submitted to GenBank for assignment of an accession number.

3. Chromosome crawling and inverse PCR

To isolate the 5' end of cps3D and upstream DNA, S. pneumoniae WU2 chromosomal DNA was first digested with Ecl136 II (an isoschizomer of SacI that results in blunt ends) and separated on a 0.6% agarose gel. Fragments ranging from 6 to 7 kb were excised and purified using GeneClean (Bio101, La Jolla, Calif.). A 35 bp XbaI UniAmp adaptor (Clontech, Palo Alto, Calif.) was ligated to the purified fragments. The fragment of interest was then amplified by using a primer for the adaptor and a primer corresponding to the predicted active site sequence (nt 1802 to 1781 of FIG. 6E) of cps3D. A 1.8 kb and a 3.8 kb PCR product was obtained. The 1.8 kb PCR product extended from the active site to the SacI site upstream of cps3D (FIG. 6E). The 3.8 kb PCR product extended from the active site to the second SacI site further upstream (FIG. 7). The polymerase chain reaction (PCR) was performed using AmpliTaq DNA polymerase (Perkin-Elmer Corp., Norwalk, Conn.) in a Perkin Elmer model 480 thermocycler according to the directions of the manufacturer. In a similar manner, the 0.9 kb fragment from the cps3D active site to the EcoRV site upstream of cps3D was amplified from a 3.5 kb EcoRV fragment from the WU2 chromosome.

To isolate the region 5' of the repeat sequence, a SacI-MscI fragment internal to the repeat region (extending from nucleotide 1 to 257 of SEQ ID NO:4) was first cloned into the insertion vector pSF151 (kanamycin resistant, Km$^r$), and used to direct an insertion-duplication event into the type 3 S. Pneumoniae WU2 chromosome. Chromosomal DNA from the resulting Km$^r$ strain, JD1008, was digested with HindIII, self-ligated, and transformed into the E. coli. The resulting Km$^r$ plasmid, pRS111, contained in the pSF151 vector and DNA flanking the insertion, i.e., DNA extending from the HindIII site in cps3B to the HindIII site in the repeat sequence (~2.3 kb of S. pneumoniae DNA).

B. Results

The cps3D nucleotide sequence is shown in FIG. 6E (SEQ ID NO:5). The Cps3D amino acid sequence :(SEQ ID NO:11) is highly homologous (56% identity, 73% similarity) to that of the UDP-glucose dehydrogenase (HasB) from Streptococcus pyogenes (Dougherty and van de Rijn, 1993). Two other sequences were detected in the GenBank which shared a high degree of homology with Cps3D. These open reading frames from the Escherichia coli and Salmonella enteritica rfb clusters have not been shown biochemically or genetically to be UDP-glucose dehydrogenases (Bastin, et al., 1993), but they share a high degree of homology with HasB and Cps3D.

Cps3D (SEQ ID NO:11) has several characteristics consistent with it being UDP-glucose dehydrogenase. The N-terminal amino acid residues 2 to 29 have all the characteristics of an NAD-binding site (Wierenga, et al., 1986), and this sequence is very homologous to regions from HasB, AlgD (the GDP-mannose dehydrogenase of Pseudomonas aeruginosa [Deretic, et al., 1987]), and the two potential UDP-glucose dehydrogenases from E. coli and S. enteritica. The homology with AlgD was previously noted by García et al., in the deduced amino acid sequence of the S. pneumoniae gene cap3-1 (García, et al., 1993). They suggested that Cap3-1 was the type 3 UDP-glucose dehydrogenase. Sequence ID NO:1 and SEQ ID NO:5 is in complete agreement with that of García et al., from the EcoRV site to the ScaI site (nucleotide 883 to 1377 FIG. 6D and FIG. 6E, containing amino acids 1 to 117, SEQ ID NO:11). However, no other homology was seen, suggesting that these investigators had cloned only the 5' end of the gene.

The Cps3D sequence at amino acid residues 251 to 263 (SEQ ID NO:11) is consistent with this being the active site of the enzyme. This region is identical at the amino acid level with that of HasB and the putative E. coli and S. enteritica UDP-glucose dehydrogenases. The homology of the active site region of HasB with that of bovine UDP-glucose dehydrogenase and AlgD has been fully described (Dougherty and van de Rijn, 1993). The cysteine at residue 259 (SEQ ID NO:11) of Cps3D contains the essential thiol group of the reactive site (Ridley, et al., 1975). The predicted size of Cps3D (45 kDa) is also similar to the size of the E. coli enzyme (47 kDa) (Schiller, et al., 1976).

EXAMPLE 9

Identification of Capsule Mutants

DNA sequencing and manipulations were performed as described in Example 8.

To determine the nature of the two cpsA mutations, identified in Example 1, the regions were amplified from the chromosomes of the mutant strains and sequenced.

Each mutant (JD611 and JD619) contained a single base pair transversion resulting in a premature stop codon in the cps3D sequence. The locations of the mutations are indicated in FIG. 6E.

To localize the three cpsB mutations, also identified in Example 1, located upstream of the UDP-glucose dehydrogenase mutations (cpsA), standard PCR or chromosome crawling was used to amplify fragments from the parent type 3 chromosome that contained either the 5' end coding sequence of cps3D (nucleotide 1027 to 1802, FIG. 6E), the promoter and the 5' end of cps3D (nucleotide 885 to 1802, FIG. 6D and FIG. 6E), or the 5' end of cps3D plus approximately 1 kb of upstream DNA (nucleotide 1 to 1802). Each of these fragments was used to transform the capsule-deficient mutants JD614 and JD692. JD692 could be transformed to encapsulation using the 5' end coding sequence of cps3D, whereas JD614 was not restored to encapsulation by this fragment but was restored by the fragment containing the 5' end plus 141 bp of upstream DNA, including the promoter. Both of the mutants were restored by the 1.8 kb fragment containing the 5' end of cps3D and the upstream DNA, and neither was restored with a fragment containing the 3' end of cps3D (nucleotide 1759 to 2385, FIG. 6E). Thus, these upstream mutations are not located in a separate gene but are in either the cps3D structural gene or its promoter. Since some capsule material is produced by these mutants, a mutation within the coding region (as in JD692) must be a missense mutation or an in-frame deletion or insertion which reduces the activity of the enzyme. The mutation in JD614 may be in the promoter, and thus, a promoter down mutation, or it may be in the structural gene but too close to the beginning of the gene for recombination and repair to occur with the fragment used.

Amplification and sequencing of the 250 bp PvuII-SspI fragment from the mutant strains A66R2 and Rx1 showed that each contained a missense mutation in the cps3D coding sequence (FIG. 6E).

EXAMPLE 10

DNA Sequences of cPs3S and cps3U

DNA sequencing and analysis was performed as described in Example 8.

The region just downstream of cps3D contains a second gene, cps3S, that is required for type 3 capsular polysaccharide biosynthesis. An open-reading frame, 1248 bp in length, is transcribed in the same direction as cps3D and is in the same reading frame (SEQ ID NO:5). The direction of transcription is in agreement with that determined using cat insertions as described in Example 4. Only 15 bp separate a potential start codon for cps3S from the stop codon of cps3D. The sequence AGGGG just upstream of the putative start codon may serve as a ribosome binding site (FIG. 6E), or due to the close proximity of cps3D, no ribosome binding site may be necessary. The deduced amino acid sequence of Cps3S predicts a protein of 48 kDa (SEQ ID NO:12), if the first start codon at nucleotide 1 (nucleotide 2227 in FIG. 6F) is utilized. Other potential start codons are located at nucleotide 1 plus 19 and +61 (nucleotide 2245 and 2287 FIG. 6F, respectively), however neither of these are positioned near a ribosome binding site.

A short region of dyad symmetry was detected downstream of cps3S at nucleotide 3718 to 3738 (FIG. 6F). The scores for primary and secondary structure yielded by the TERMINATOR program of the GCG sequence analysis package (p=3.95, s=22) suggest that this region could function as a weak rho-independent terminator. However, this sequence is 241 bases past the cps3S stop codon and closer to the start of the next open reading frame, i.e., cps3U. Therefore, the sequence may have more to do with the expression of cps3U than of cps3S. In fact, a potential promoter sequence for cps3U was detected upstream of the region of dyad symmetry, suggesting the potential structure could serve as an attenuator of cps3U expression. The cpsU open reading frame (SEQ ID NO:5), 918 bp in length, is transcribed in the same direction as cps3D and cps3S, and is predicted to encode a protein of 34 kDa (SEQ ID NO:13).

EXAMPLE 11

Cps3S is Homologous to Polysaccharide Synthases

A search of the GenBank revealed that the predicted Cps3S protein (SEQ ID NO:12) is homologous to polysaccharide synthases. The greatest degree of homology was found with HasA, the hyaluronic acid synthase from *S. pyogenes* (23% identity, 50% similarity) (DeAngelis, et al., 1993b; Dougherty and van de Rijn, 1994). Hyaluronic acid consists of alternating N-acetyl glucosamine and glucuronic acid residues. Hyaluronic acid and the pneumococcal type 3 capsule are similar in structure in that both are composed of $\beta(1–4)$ linked repeating disaccharide units containing glucuronic acid. Like pneumococcal type 3 capsule, hyaluronic acid capsule contains both $\beta(1–3)$ and $\beta(1–4)$ linkages, however the linkage to glucuronic acid is $\beta(1–4)$ in hyaluronic acid but $\beta(1–3)$ in type 3 capsule (Reeves and Goebel, 1941). Homology was also seen between Cps3S and NodC from Rhizobium meliloti (21% identity, 47% similarity). NodC is necessary for the synthesis of nodulation factor, a substituted oligosaccharide consisting of $\beta(1–4)$ linked N-acetyl glucosamine residues (Lerouge, et al., 1990). It has previously been noted that HasA and NodC are homologous to polysaccharide synthases, including FBF15 of Stigmatella aurantiaca, pDG42 of Xenopus laevis, and chitin synthases from both *Saccharomyces cerevisiae* and *Candida albicans* (DeAngelis, et al., 1993b; Dougherty and van de Rijn, 1994; Atkinson and Long, 1992; Debellé, et al., 1992). Cps3S is also homologous to these proteins. These results suggest that Cps3S is the type 3 capsular polysaccharide synthase.

The PILEUP program was used to align the amino acid sequences of the bacterial polysaccharide synthases Cps3S (SEQ ID NO:12), HasA, NodC, and FBF15. Only a few clusters of amino acids are found to be conserved in all four proteins. A few of these, GKR (residues 131 to 133 SEQ ID NO:12), an acidic region VDSD (153 to 156 SEQ ID NO:12), DRXLT (256 to 260 SEQ ID NO:12), QQXRW (292 to 296 SEQ ID NO:12), and WXTR (418 to 421 SEQ ID NO:12), are also found in the eukaryotic polysaccharide synthases.

Since all four proteins contain highly hydrophobic stretches, hydrophobic amino acids are found conserved at several locations throughout the proteins. Four hydrophobic stretches identified in Cps3S are found in all four proteins. These regions may span the cell membrane. This hypothesis has been supported for NodC. Immunogold labeling revealed a surface location for NodC, and the C-terminal hydrophobic region was shown to direct the insertion of an alkaline phosphatase fusion protein to the cell membrane (Johnson, et al., 1989; John, et al., 1988). Earlier studies indicated that the type 3 capsule synthesizing activity also has a membrane location (Smith, et al., 1961). The last hydrophobic stretch may be required for the function of Cps3S since the insertion in JD897 which eliminated this region (the last 45 amino acids of the protein) resulted in loss of capsule production (FIG. 6F). Expression of Cps3S in *E. coli* was, like that of NodC, lethal to the host.

A. Method

1. Expression of Cps3S

A 2.1 kb Sau3AI-PstI fragment containing the 3' end of cps3D and the entire cps3S gene was cloned from pJD351 into the expression vector pKK223-3 (Brosius and Holy, 1984) at the polylinker BamHI-PstI sites to yield pJD424. Cultures of *E. coli* TG-1 (Sambrook, et al., 1989) or TG-1 transformants were grown to exponential phase, at which time isopropyl-b-D-thiogalactoside (IPTG) was added to a concentration of 1 mM to induce expression from the tac promoter of pKK223-3.

Transformations and other DNA manipulations were performed as described in Example 1.

B. Results

The sequence from residues 211 to 233 in NodC was noted for the large number of cysteine residues. It has been suggested that this region participates in the binding of divalent cations which are necessary for the production of chitin and chitin-like molecules (Atkinson and Long, 1992). Type 3 capsule synthesis requires Mg++ (Smith, et al., 1960). Although this region in Cps3S contains only one cysteine, the region is highly conserved between all four proteins.

The GenBank search also revealed that Cps3S has homology over short stretches to the rhamnosyl transferase RfbN from Salmonella enteritica, which is necessary for the production of O-antigen in type B strains. This enzyme creates an α(1–4) linkage to mannose in the O-antigen repeat unit. The homologous regions are a subset of those conserved regions common to HasA, NodC, and Cps3S, but the best homology is seen in the region 229 to 278 (SEQ ID NO:12).

In the production of Group B type III capsular polysaccharide, the galactosyl transferase CpsD transfers a galactose to a molecule located in the cell membrane. Rubens et al. (1993), suggested that the acceptor may be dolichol or a related molecule, and identified a region of CpsD with homology to putative dolichol binding regions of several proteins. Although it is not clear that such sequences are actually involved in dolichol recognition or binding (Schutzbach, et al., 1993), several similar regions (e.g., at residues 7 to 20, 21 to 38, and 388 to 401, as numbered in SEQ ID NO:12) are present in CpsS. Since the putative dolichol binding motif [FL(F/I)VXFXXI(P/L)FXFY] (Albright, et al., 1989; Kelleher, et al., 1992) is a highly hydrophobic sequence that is rich in phenylalanines, the sites in Cps3S may actually reflect the hydrophobicity of the molecule and the A-T rich bias in the DNA sequence rather than indicating a specificity for dolichol-like molecules. It is not known whether S. pneumoniae utilizes an intermediate acceptor in capsule synthesis, however the capsular polysaccharides of several serotypes have been found to be covalently linked to the cell wall. Type 3 capsule, by contrast, is not covalently linked to the cell and is generally considered an exopolysaccharide (Sorensen, et al., 1990). Therefore, if Cps3S does use a membrane bound acceptor, it is likely not the final acceptor.

EXAMPLE 12

Cps3U is Homologous to Glucose-1-Phosphate Uridylyltransferases and Cps3M is Homologous to Phosphomutases The gene downstream of cps3S is designated as cps3U (SEQ ID NO:5) based on its probable function. The amino acid sequence of Cps3U (SEQ ID NO:13) showed a high degree of homology with glucose-1-phosphate uridylyltransferases from several other bacterial species. The highest degree of homology was found with GtaB from Bacillus subtilis (55% identity, 73% similarity). The active site of glucose-1-phosphate uridylyltransferase has not been characterized from any of the bacterial enzymes, however, the active site in the enzyme from potato tuber (Solanum tuberosum) has been investigated. Kazuta et al., recognized 5 lysine residues present at the active site (Kazuta, et al., 1991), and by mutational studies Katsube et al., showed that one of these residues was important for function, and a second was absolutely required (Katsube, et al., 1991). Cps3U contains 24 lysines, six of which are absolutely conserved among the six bacterial glucose-1-phosphate uridylyltransferases in the database. Only one region from Cps3U containing a conserved lysine can be aligned well with the potato tuber enzyme sequence. It is homologous to the region containing the required lysine.

The final gene in SEQ ID NO:5, is cpsM with a deduced amino acid sequence (SEQ ID NO:14). The CpsM amino acid sequence revealed significant homology to both phosphoglucomutases (PGM) and phosphomannomutases (PMM) from a diverse group of microorganisms. Contained with CpsM is a phosphoserine signature sequence (GIMVTASHTPAPFNG) conserved within the reported active sites of both PGMs and PMMs. However, approximately 15% of the C terminus present in other phosphomutases, and apparently more important for their function, is absent from CpsM. Phosphomutase activity from a recombinant CpsM was not detected in E. coli, suggesting that cpsM may encode a non-functional protein.

EXAMPLE 13 cps3S and cps3D are Transcribed as an Operon

A. Methods

Southern blotting was performed as described in Example 4, all other DNA manipulations, including insertion deletion mutations, were performed as described in Example 1. The locations of mutations can be seen in FIG. 6E and FIG. 6F.

B. Results

Use of fragments subcloned from the cps3DSU region to direct insertion-duplication mutations in the parent type 3 chromosome resulted in several mutants that produced no detectable capsule (FIG. 9) and exhibited the extremely rough phenotype described by Taylor (1949). The colonies were very small and rough, and the cells clumped when grown in liquid culture. DNA sequencing revealed that the sites of the mutations are within cps3S (FIG. 6F). The lack of capsule production in these mutants must be due to loss of cps3S expression, rather than to a polar effect on downstream genes, since insertions within cps3U or cps3M, the next genes downstream, had no apparent effect on capsule production.

Molecular and genetic evidence suggest cps3S is in an operon with cps3D. Sequence analysis revealed no potential promoter sequences in the region upstream of cps3S (FIG. 6E, SEQ ID NO:5). The phenotypes of several insertion mutants also suggest that no promoter is located in the 3' end of cps3D and that cps3S is transcribed from the cps3D promoter. The sites of these insertions are shown in FIG. 6E, FIG. 6F and FIG. 7, however, the structures of the mutations are more fully illustrated in FIG. 9. To insure that the plasmids had inserted as expected for insertion-duplication mutations, chromosomal DNA from the mutant strains was subjected to Southern blot analysis.

Insertion mutants were digested with MscI/FspI for JD982, MscI/SalI for JD983, and MscI/KpnI for JD908, JD902, and JD900 and run on agarose gels and blotted as described in Example 4. The blots were probed with vector pJY4164. Increasing distance from the MscI site to the end of the vector was demonstrated by an increase in the size of the upper band. A faint band in the JD982 lane was observed, likely a result of partial digestion. The 4.7 kb and 4.8 kb bands in JD982 and JD908, respectively, indicate that these mutants contain a duplication of the inserted plasmid.

Insertion of the plasmids results in a duplication of the cloned fragment. Therefore, mutant strains such as JD908, in which the duplicated fragment contains both the 5' end of cps3S and the 3' end of cps3D, have a full-length copy of cps3S downstream of the plasmid insertion. In addition, the full-length copy is contiguous with the 3' end of cps3D. Therefore, if cps3S had its own promoter, or if one were located in the 3' end of cps3D, these insertions should not result in a loss of cps3S expression. However, four such insertions have been made in the WU2 chromosome (JD846, JD897, JD898, and JD908), and even with a duplication of up to 450 bp of the 3' end of cps3D, a loss of capsule production was observed.

Figure 9:
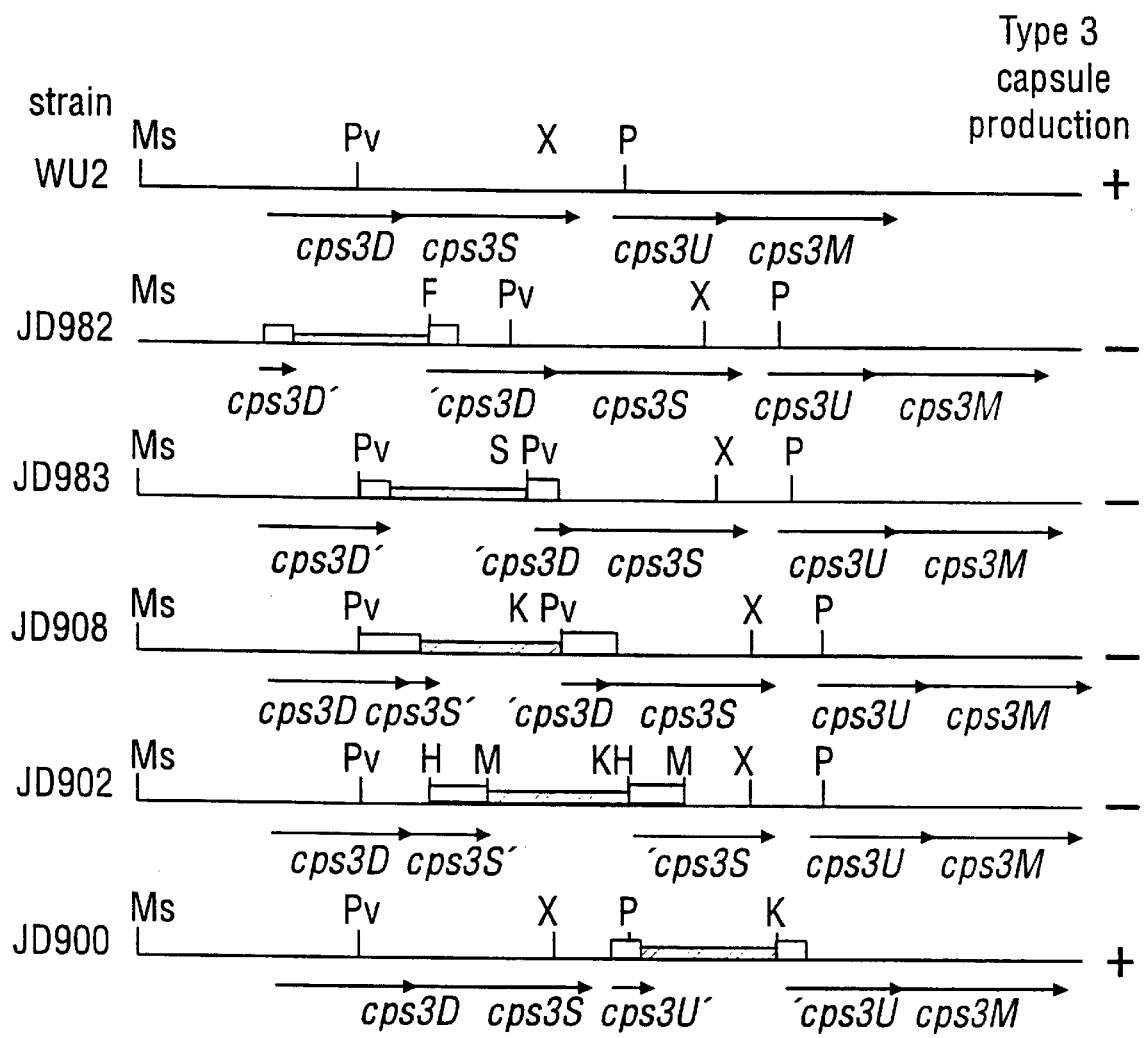
FIG. 9. Location of insertion mutations in the type 3-specific region of the S. pneumoniae WU2 chromosome. Schematic illustration of the insertions. The schematic was derived from Southern blot analysis such as that shown in FIG. 11a and FIG. 11b. The ability of the strains to produce type 3 capsule is indicated. Restriction sites are: F, FspI; H, HindIII; K, KpnI; Ms, MscI; P, PstI; Pv, PvuII, X, XbaI.

Two more internal insertions in cps3D were created. As expected these insertions eliminated capsule production (FIG. 9). However, since cps3D and cps3S are transcribed as an operon, this result does not prove that cps3D is required for capsule synthesis. That fact is demonstrated by the lack of capsule production seen in strains containing non-polar point mutations in cps3D (Example 14).

EXAMPLE 14

In Vitro Polymerization Assay

To evaluate the competence of the mutants to synthesize type 3 capsule, an in vitro polymerization assay was used.
A. Methods
1. In vitro polysaccharide synthesis Type 3 capsular polysaccharide was synthesized and quantitated in vitro using a modification of the method of Smith, et al., 1961. Crude extracts containing cell membranes and cytoplasm were prepared from 200 ml of *S. pneumoniae* cultures harvested at an $o_{600}$ of 0.25 as described (Yother and White, 1994), except that cell material was concentrated 200-fold, and all steps were performed using a thioglycolate buffer (10 mM sodium thioglycolate, 5 mM $MgSO_4$, 100 mM Tris-HCl pH 8.3) to stabilize the enzymes (Smith, et al., 1960). The digestion of cell wall material by mutanolysin treatment was performed in this buffer and 20% sucrose. Protoplasts were sonicated three times for 15 s at 35% power at 0° C.

Polysaccharide synthesis was carried out at 34° C. for 2 h in a 1 ml reaction containing 100 ml of extract, 5 mM UDP-glucose, 5 mM UDP-glucuronic acid (where indicated), and 1 mM NAD, in the thioglycolate buffer. The reaction was boiled 1 min then quickly cooled to 25° C. in $H_2O$. Following centrifugation for 30 s at 8160 x g, the type 3 specific monoclonal antibody 16.3 (Briles, et al., 1981a) was added in excess to the supernatant and incubation was continued at 37° C. for 30 min.

The specific antigen-antibody complexes were measured at 650 nm in a spectrophotometer, and the amount of capsule was determined by comparison with a standard curve prepared using purified type 3 polysaccharide purchased from ATCC (Rockville, Md.) (Bernheimer, 1953). Reactions were done in triplicate and were standardized to protein content of the crude extract, as determined in duplicate using the Bio-Rad Laboratories (Hercules, Calif.) protein assay kit.
B. Results The spontaneous mutants JD611 and JD619 (cpsA1 and cpsA2), which contain stop mutations in cps3D, produce no detectable capsular material. However, both synthesized high molecular weight type 3 polysaccharide in a cell-free system in vitro when provided with the nucleotide sugar precursors, i.e., UDP-glucose and UDP-glucuronic acid (Table 7). No capsule was produced by these mutants when UDP-glucuronic acid was omitted from the reaction. These results indicate that these mutants produce no capsule due to the lack of UDP-glucuronic acid and support the conclusion that Cps3D is the UDP-glucose dehydrogenase. They also confirm that stop mutations in cps3D are not polar on cps3S.

The increased amount of polysaccharide produced by the WU2 extract (as compared to that produced by that of JD611 or JD619) may be explained by the observation of Smith et al. (1961), that increased amounts of type 3 capsule are produced in vitro when a small amount of unpurified polysaccharide is already present in the reaction.

The mutants which contain insertions within cps3S (JD902), or between the full-length copies of cps3D and cps3S (JD908, JD897) were unable to synthesize significant amounts of capsule even with both precursors present. These results emphasize the role of Cps3S in capsule synthesis and support the conclusion that cps3D and cps3S are transcribed as an operon.

The capsule-deficient mutants JD614 and JD692 synthesized only small amounts of additional polysaccharide in the in vitro assay. This result is somewhat surprising since JD692, which was shown to contain a missense mutation within the cps3D coding region, should still make a functional Cps3S (i.e., the cps3D mutation must not be polar since the intact cells are able to synthesize some polysaccharide). The result may suggest that the defective UDP-glucose dehydrogenase in some way interferes with the ability to synthesize the normal polysaccharide. Alternatively, the stability of the cpsDS transcript may be altered by the mutation, resulting in a reduced amount of CpsS.

TABLE 7

In vitro capsule synthesis assay.

| strain | Cps phenotype a | UDPGAb | CPS ($\mu$g/mg protein) |
|---|---|---|---|
| JD611 | Cps3D$^-$S$^+$ | + | 9.8 ± 0.6 |
|  |  | − | 0.9 ± 0.2 |
| JD619 | Cps3D$^-$S$^+$ | + | 5.7 ± 0.3 |
|  |  | − | 0.2 ± 0.1 |
| JD614 | Cps3D*S* | NA$^b$ | 5.4 ± 0.4 ($t_o$)$^c$ |
|  |  | + | 5.9 ± 0.5 (0.5)$^c$ |
| JD692 | Cps3D*S* | NA | 4.8 ± 0.3 ($t_o$) |
|  |  | + | 7.0 ± 1.0 (2.2) |
| JD902 | Cps3D$^+$S$^-$ | + | 1.7 ± 0.3 |
| JD908 | Cps3D$^+$S$^-$ | + | 1.5 ± 0.1 |
| JD897 | Cps3D$^+$S$^-$ | + | 1.1 ± 0.1 |
| WU2 | Cps3D$^+$S$^+$ | NA | 3.8 ± 0.2 ($t_o$) |
|  |  | + | 16.6 ± 0.3 (12.8) |
|  |  | − | 16.3 ± 0.8 |
| D39 | Cps2$^+$ | + | 0.5 ± 0.3 | a Capsule phenotypes are based on the cps3D and cps3S genotypes. − indicates either a stop or insertion mutation (see FIG. 6E, FIG. 6F and FIG. 9 for locations of mutations). *indicates either a missense or in-frame deletion or insertion in cps3D that apparently also affects cps3S.
$^b$NA, not applicable.
$^c$For strains which produce capsule in vivo, the amount of polysaccharide present at the start of the assay ($t_o$) is given, and the amount of polysaccharide produced during the assay is indicated in parentheses.

EXAMPLE 15

Biochemical Pathway

Based on the genetic analysis, the homology of the amino acid sequences of the type-specific genes to the sequences of enzymes of known function, the behavior of the mutants in biochemical and immunochemical assays, and previous biochemical characterizations of type 3 strains (Austrian, et al., 1959; Dillard and Yother, 1994; Smith, et al., 1960; Smith, et al., 1961; Bernheimer, 1953), a pathway for the biosynthesis of type 3 capsular polysaccharide is proposed (FIG. 10). The last of the type-specific genes, cps3M, is homologous with phospxhoglucomutases from several bacterial species. Even though maintained in the type 3-specific region, Cps3U and Cps3M may not be required for capsule synthesis, since an insertion internal to cps3U (which has a polar effect on cps3M) does not result in loss of capsule production (FIG. 7 and FIG. 9), as judged by colony morphology on blood agar medium.

EXAMPLE 16

The Downstream Non Type-specific Flanking Region and Mapping Other Capsule Types Southern blots of digested chromosomal DNA from strains 2, 3 and 6B and probed with pJD377 was performed as described in Example 4. Faint bands in addition to the band of interest was observed on Southern blots. This was probably due to the detection of fragments containing the amiA-like genes which have homology to plpA. DNA was either digested with BglII, SacI of Hind III. Other laboratory techniques were as described in Example 1 or Example 8.

Sequence analysis of the 1.2 Kb SacI-HindIII fragment (from plasmid JD377) employed in Example 5 contained the 3' end of cps3M and the 5' half of a gene with 50% identity to the S. pneumoniae amiA (SEQ ID NO:6). The amiA-like sequence has recently also been identified by Pearce et al. and named exp1 (Pearce, et al., 1993), and subsequently renamed plpA (Pearce, et al., 1994). Further Southern hybridizations performed as described in Example 4 showed that the non-type-specific homologous DNA in the 1.2 kb SacI-HindIII fragment is plpA.

A partial copy of a transposase gene was also identified immediately adjacent to and between cpsM and plpA. Previous findings of repetitive elements linked to the capsule locus suggest that the deletions in this region may be the result of a transposition event, possibly one which introduced the type 3-specific cassette.

Figure 11:
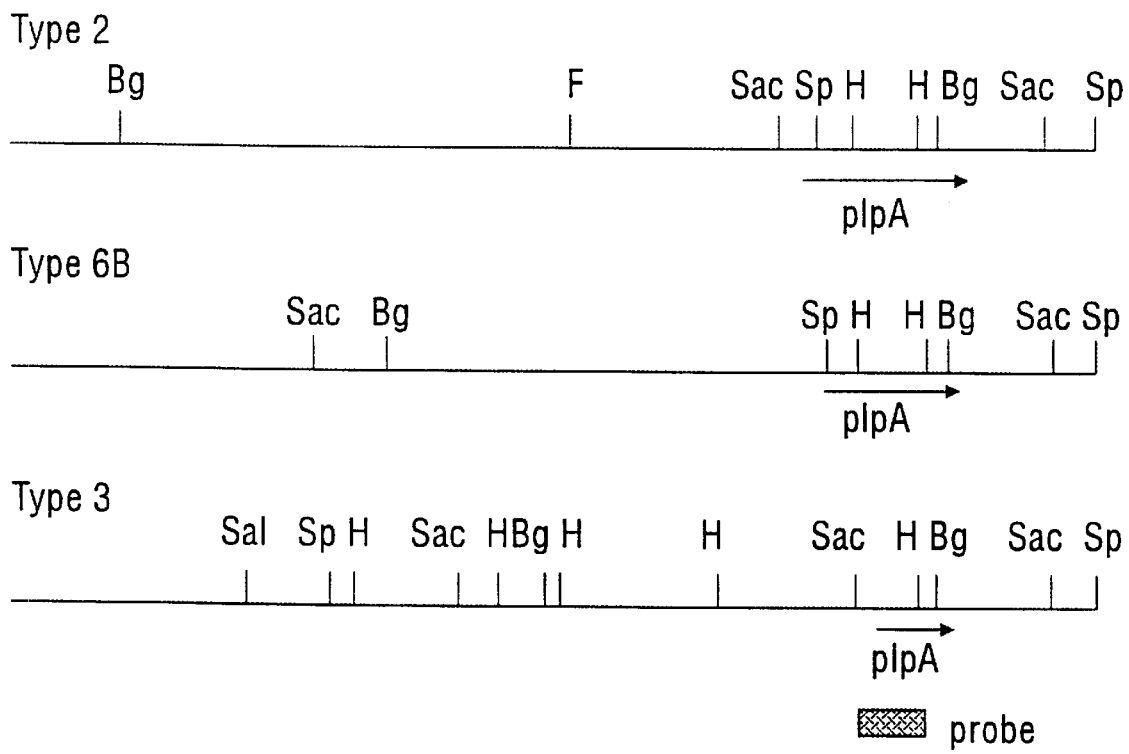
FIG. 11. Chromosome maps of the capsule regions in strains of types 2, 3, and 6B. The SacI-HindIII fragment (pJD377) from type 3 used for the probe is shown below the maps. Restriction sites are Bg, BglII; F, FspI; H, HindIII; S, SalI; Sac, SacI; Sp, SphI.

If, as in type 3, the homologous region is directly adjacent to the type-specific genes in other serotypes, it should be possible to map other type-specific genes using this fragment. This was found to be the case, and the chromosome maps of the capsule regions in strains of types 2, 3, and 6B, from Southern blots, are shown in FIG. 11. It can be seen in FIG. 11 that restriction sites located to the right of the plpA fragment are highly conserved in all three strains. The type 3 strain differs slightly in this region due to a deletion of the 5' end of plpA. The sites located to the left of plpA are divergent among the capsule types. The close linkage of the region to all the necessary type-specific genes for each type, combined with the different restriction maps and the fact that the type 3-specific genes are located directly adjacent to this fragment, suggests that this region contains the type-specific genes in all three capsule types.

EXAMPLE 17

The Upstream Non Type-specific Flanking Region

In order to isolate DNA 5' of the biosynthetic genes, a 1.8 kb fragment extending from the upstream SacI sites to just before the PvuII site in cps3D (nucleotide 1 through 1802 of FIG. 6D and FIG. 6E, nucleotide 1 through 934 of SEQ ID NO:4 and nucleotide 1 through 868 of SEQ ID NO:5) was amplified from the type 3 WU2 chromosome using inverse PCR as described in Example 8. All other materials and methods were as described in Example 1, 4 and 8.

The 1.8 kb fragment was then used to probe HindIII-digested chromosomal DNA from seven S. pneumoniae serotypes (2, 3, 5, 6, 8, 9 and 22). The fragment hybridized strongly with the expected fragments at 2.2 and 2.3 kb in the type 3 strain. However, hybridization was also observed with fragments of 2.6 and 8 kb, along with weak hybridization with several other fragments (3.0, 3.1, and 4.4 kb). Likewise, each of the strains representing other capsule types contained two strongly homologous fragments (4.8 and 8.0 kb for types 2, 6B, 8, 9; 2.2 and 4.8 or 12 for types 5 and 22, respectively) and at least one weakly homologous fragment (4.4 kb). When chromosomal DNAs of types 2, 3, and 6B were digested with PstI, PvuII, or SacI/HindIII, and probed with the 604 bp SacI-HindIII fragment (pJD392) upstream of cps3D (within nucleotides 1 through 610; SEQ ID NO:4, FIG. 6D), 4 to 10 bands were detected in each.

Transformation studies were performed to examine linkage of the repeat upstream region to the type-specific capsule genes. The plasmid (pJD392) containing the 604 bp SacI-HindIII fragment was introduced into the chromosome of the type 3 strain. The insert, located in the 2.2 kb HindIII fragment (FIG. 7) adjacent to the type 3-specfic genes, did not affect capsule production. When the resulting strain was used to transform recipients of types 2 and 6B, greater than 95% of the erythromycin-resistant transformants expressed type 3 capsule. However, when pJD392 was transformed into strains of types 2 and 6B, the plasmid inserted into the 8 kb HindIII fragment, and the type specific genes could not be moved to strains of heterologous types (i.e., 2, 3, or 6B) by transformation and selection for linkage to the erythromycin marker in the insertions. This suggests that this region may be found in more than one location and not necessarily located, adjacent to the cps locus in all other serotypes.

To isolate DNA 5' of the SacI site in the repeat region (SEQ ID NO:4), a 257 nucleotide SacI-MscI fragment internal to the repeat region was used to direct an insertion-duplication event in the type 3 S. pneumoniae WU2 chromosome. The flanking 2.3 kb HindIII fragment was then closed from the chromosome, as described in Example 8. The 1.4 kb SacI fragment from within this HindIII fragment was then used to probe HindIII-digested chromosomal DNA from three S. pneumoniae serotypes (2, 3, and 6B). The fragment hybridized strongly with the expected 2.3 kb band in the type 3 strain. Less intense bands were also observed at 0.8, 3.0 and 8.0 kb. The type 2 and 6B strains each contained a strongly homologous band at 0.8 kb and a strong but less intense band at 9.0 kb. Digestion of types 2, 3, and 6B with other enzymes followed by hybridization with the SacI fragment yielded the results shown in Table 8. The results show that this region is found in only one location in all serotypes examined. The weak bands observed for serotype 3 probably represent hybridization of the 5' end of the repeat region 132 nucleotides upstream of the SacI site (FIG. 7).

TABLE 8

BANDS DETECTED BY SOUTHERN BLOTTING
StraRestriction Enzyme used to digest chromosomal DNA.

|  | BglII | SacI | SphI |
|---|---|---|---|
| type 2 | >12* | 4.0,>12 | 12,>12 |
| type 3 | >12* | 1.4, (weak at 3.5,8.5,>12) | 10 (weak at 12.5,13) |
| type 6B | >12* | 4.0,12 | 12,>12 |

*The BglII fragments were not identical in size. Numbers represent size of bands in kb as observed on southern blots carried out as described in Example 4.

DNA in the 1.4 kb SacI fragment was sequenced using techniques as described in previous Examples, and can be seen, alongside the predicted amino acid sequences, in FIG.

6A, FIG. 6B and FIG. 6C (SEQ ID NO:1, SEQ ID NO:2, SEQ ID NO:3, SEQ ID NO:7, SEQ ID NO:8, SEQ ID NO:9 and SEQ ID NO:10).

EXAMPLE 18

Capsule Type Expression and Virulence in *S. pneumoniae*

In these studies, isogenic strains expressing the type 3 capsule were constructed and the effect on virulence was determined. Strains of types 2, 5, and 6B were used as recipients. The type 2 and 5 strains differ in virulence from the type 3 strain in terms of time required to cause death (shorter with type 2) and $LD_{50}$ (lower with type 5). The type 6B strain is of low virulence in mice. The results showed that expression of the type 3 capsule attenuated the virulence of the type 5 strain, caused the type 6B strain to become highly virulent, and had no effect on the type 2 strain. Thus, in general, the expression of virulence was correlated with the type of capsule expressed.

A. Methods

1. Transformations, serotyping, ELISAs and restriction enzyme fragment patterns.

Transformations ELISAs and DNA manipulations were performed as described previously in Example 1. All transformants and parental strains were serotyped with capsule type-specific antisera (Statens Seruminstitut, Copenhagen, Denmark) in slide agglutination assays. Genomic DNA, was digested with HindIII for 4 h at 37° C. and electrophoresed overnight through 0.7% agarose in Tris-borate-EDTA buffer.

2. Analysis of PspA.

Bacteria were grown in CDM containing 2% choline, a condition that causes release of PspA into the culture medium. Filtered, unconcentrated supernatant fluids (20 µl) were electrophoresed in sodium dodecyl sulfate (SDS)-12% polyacrylamide gels. Western blotting (immuno-blotting) was performed by using a semidry electroblotter (Bio-Rad Laboratories, Richmond, Calif.), and the blots were processed as described previously (Yother et al., 1992). The PspA-specific monoclonal antibodies XiR278, Xi126, and 2A4 were kindly provided by Larry McDaniel (University of Alabama at Birmingham). Silver staining was performed by using the Silver Stain Kit from Stratagene Cloning Systems, Inc. (La Jolla, Calif.).

3. Characterization of morphology and capsule production.

For average chain length determinations, bacteria were grown in THY to an optical density at 600 nm ($OD_{600}$) of ~0.3. Chain lengths were determined microscopically by using a Petroff-Hauser counting chamber (Auther C. Thomas Co., Philadelphia, Pa.). An average of five squares was counted for each strain. Comparisons of average chain lengths were determined by using the two-sample rank test (Zar, 1984).

The number of cells per colony was determined by using bacteria grown on blood agar medium for 18 h at 37° C. in 5% $CO_2$. A plug containing a single colony was obtained with a sterile Pasteur pipette and then resuspended in 50 µl of THY. Tenfold serial dilutions were performed in THY and plated on blood agar medium. Plates were incubated overnight at 37° C. in 5% $CO_2$, and the number of CFU per colony was calculated.

Buoyant density determinations were performed by using bacteria grown on blood agar medium or in THY. Bacteria grown on solid medium were harvested by washing each plate with water, centrifuging the suspension, and then resuspending the pellet to an $OD_{600}$ of ~0.4 with water. Ten-milliliter liquid cultures, grown to an $OD_{600}$ of ~0.5, were harvested by centrifugation for 10 to 15 min at 8,000 to 16,000 x g. Bacteria were washed twice with water prior to being loaded onto 10-ml, continuous, 0 to 50% Percoll (Pharmacia, Piscataway, N.J.) gradients. As standards, 5 µl of density marker beads (Pharmacia) ranging in size from 1.033 to 1.076 g/ml, were also loaded. Gradients were centrifuged for 30 min at 8,000 x g with the brake off. A standard curve based on the migration of the marker beads was generated, and the density of the bacteria was determined by extrapolation.

For determinations of total capsule content, 1.5-ml cultures grown in CDM containing 0.0005% choline were harvested by centrifugation at 8,000 to 16,000 x g for 10 min. Culture supernatant fluids were filtered and saved, and the cells were resuspended in 500 µl of protoplast buffer (20% sucrose, 0.005 M Tris [pH 7.4], 0.0025 M $MgSO_4$). Cell sonicates were produced by three cycles of a 10-s pulse, followed by a 10-s incubation on ice, with a Fisher Sonic Dismembrator model 300 (Fisher Biotechnology, St. Louis, Mo.) with the intensity control set at 30. Culture supernatant fluids and cell sonicates were stored at ~20° C.

For surface localization assays, 1.5-ml cultures grown to an $OD_{600}$ of ~0.5 were heat killed by incubation at 65° C. for 30 min. Bacteria were harvested by centrifugation, and culture supernatant fluids were filtered and saved. After the pellets were washed twice with phosphate-buffered saline (PBS; 137 nM NaCl, 2.7 mM KCl, 4.3 mM $Na_2HPO_4 \cdot 7H_2O$, 1.4 mM $KH_2PO_4$), the pellets were resuspended in 1.5 ml of THY. Samples were stored at 4° C.

4. Virulence assays.

The virulence of the type 3 derivatives was compared with that of the parental strains in BALB/ByJ female mice (Jackson Laboratory, Bar Harbor, Me.). Bacteria were grown to the mid-log phase in THY. Samples were diluted serially in sterile lactated Ringer's solution, and 0.2 ml was used to infect mice intraperitoneally (i.p.) or intravenously (i.v.), as indicated. Fifty percent lethal doses ($LD_{50}$s) were determined by the method of Reed and Muench (1938) and compared by Fisher's exact test (Zar 1984). Median times to death were analyzed by using the two-sample rank test (Zar 1984). The P values were determined by using a two-tailed table.

B. Results

As described in Table 3, strain JD770 contains a non-destructive insertion in the type 3 capsule locus. The amount and cellular localization of the capsular material produced by JD770 is identical to that of its parent strain WU2. Transformation of JD770 chromosomal DNA, and selection for erythromycin resistance, results in isolates that express the type 3 capsule of the donor but not the capsule of the recipient strain (Example 6). Based on this result, JD770 DNA was used to transform type 2, 5, and 6B recipients and selected for erythromycin-resistant isolates (see Table 9). All of the type 2 Ery$^r$ transformants expressed the type 3 capsule but not the type 2 capsule. >95% of the type 5 and type 6B Ery$^r$ transformants expressed the type 3 capsule but not the capsule of the recipient parent. The remainder of the type 5 and 6B transformants expressed the capsular type of the recipient parent only.

TABLE 9

BACTERIAL STRAINS

| Strain | Derivation[a] | Relevant phenotype | Chain length[b] | Reference |
|---|---|---|---|---|
| WU2 | Clinical isolate | Encapsulated type 3 | 2.3 ± 0.14 | Briles et al. 1981b |
| JD770 | pJD330[c] × WU2 | Encapsulated type 3; Em[r] | 2.4 ± 0.19 | This study |
| D39 | Clinical isolate | Encapsulated type 2 | 6.2 ± 0.69 | Avery et al. 1944 |
| JD803 (2/3)[d] | JD770 × D39 | Encapsulated type 3; Em[r] | 6.6 ± 076 | This study |
| JD804 (2/3) | JD770 × D39 | Encapsulated type 3; Em[r] | 5.2 ± 074 | This study |
| DBL5 | Clinical isolate | Encapsulated type 5 | 9.2 ± 080 | Yother et al. 1982 |
| TK5010 (5/3) | JD770 × DBL5 | Encapsulated type 3; Em[r] | 2.1 ± 008[e] | This study |
| TK5011 (5/3) | JD770 × DBL5 | Encapsulated type 3; Em[r] | 2.4 ± 013[e] | This study |
| TK5012 (5/3) | JD770 × DBL5 | Encapsulated type 3; Em[r] | ND[f] | This study |
| DBL1 | Clinical isolate | Encapsulated type 6B | 2.7 ± 11 | Briles et al. 1992 |
| TK3026 (6B/3) | JD770 × DBL1 | Encapsulated type 3; Em[r] | 2.4 ± 15 | This study |
| TK3028 (6B/3) | JD770 × DBL1 | Encapsulated type 3; Em[r] | 3.1 ± 30 | This study |

[a]Crosses were done by transformation. Each derivative is the result of at least three backcrosses with the parental recipient strain.
[b]The numbers of cells per chain (means ± standard errors) were determined during this study by microscopic examination.
[c]pJD330 contains a Sau3AI fragment that is part of the type 3 capsule locus. It was constructed in pJY4163 (Yother et al., 1992) which contains an Em[r] marker. Insertion of pJD330 into the S. pneumoniae chromosome places the Em[r] marker in the type 3 locus but does not affect capsule expression.
[d]For clarity, strains will be listed by strain number, genetic background, and capsule type expressed. For example, JD803 (2/3) represents a strain with a type 2 genetic background expressing a type 3 capsule.
[e]significantly different from recipient parent strain ($P < 0.001$).
[f]ND, not determined.

To produce essentially isogenic strains, two independent transformants from each cross were backcrossed at least three times to their respective parent recipient strains. The final isolates were examined for restriction enzyme fragment patterns, pneumococcal surface protein A (PspA) expression, capsule expression, and morphological characteristics prior to testing in a mouse virulence model.

1. Restriction enzyme fragment patterns.

The HindIII restriction patterns of the strains used in these studies can be easily distinguished. In all cases, the type 3 derivatives constructed here were found to have the HindIII pattern of the recipient strain, indicating that gross alterations in the genomic DNA content had not occurred and that the parent donor strain JD770 had not been inadvertently re-isolated.

2. PspA expression.

PspA varies with respect to molecular weight, antigenic determinants, and strain distribution. PspA serotypes and capsular serotypes do not correlate. The strains used in these studies expressed PspAs that had different molecular weights and reacted with different PspA-specific monoclonal antibodies. In all cases, the PspAs of the type 3 derivatives constructed here were found to have the molecular weight and antibody reactivities of the parent recipient strains.

3. Morphologic characterization and capsule production.

Microscopic examination revealed that alteration of capsular type had no effect on the chain length of the type 2 and type 6B derivative strains. However, the chain lengths of the type 5 derivatives differed significantly from that of the type 5 parental strain and were almost identical to that of the type 3 parent (Table 9).

Figure 12:
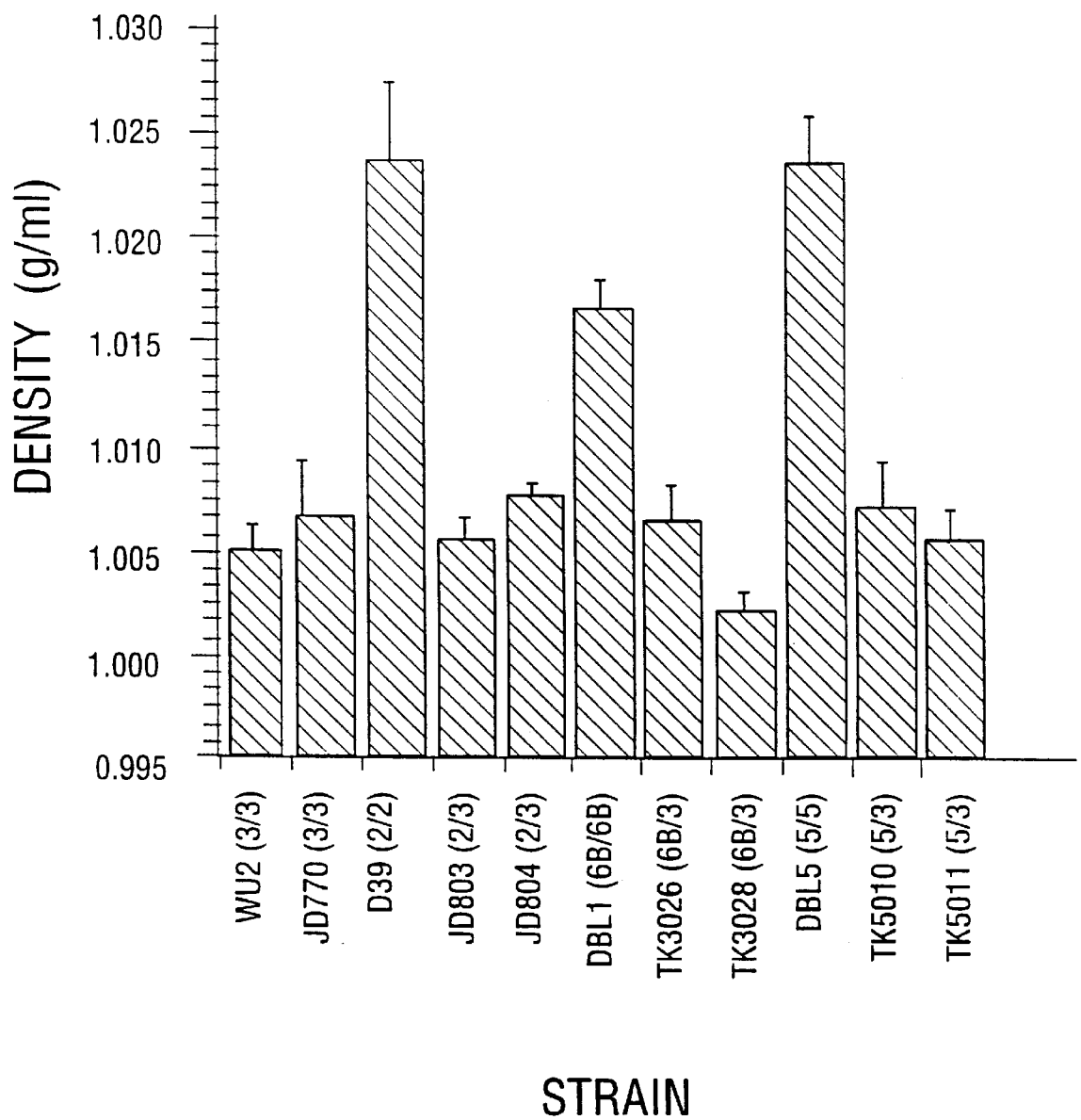
FIG. 12. Production of type 3 capsule. Buoyant densities of parents and derivatives expressing the type 3 capsule. Densities were determined by centrifugation on 0 to 50% Percoll gradients for 30 min at 8,000 x g. Samples were grown in duplicate, and the density of each sample was determined in duplicate gradients. The results shown were obtained with bacteria grown on solid medium. Identical results were obtained from growth in liquid culture.
Figure 13:
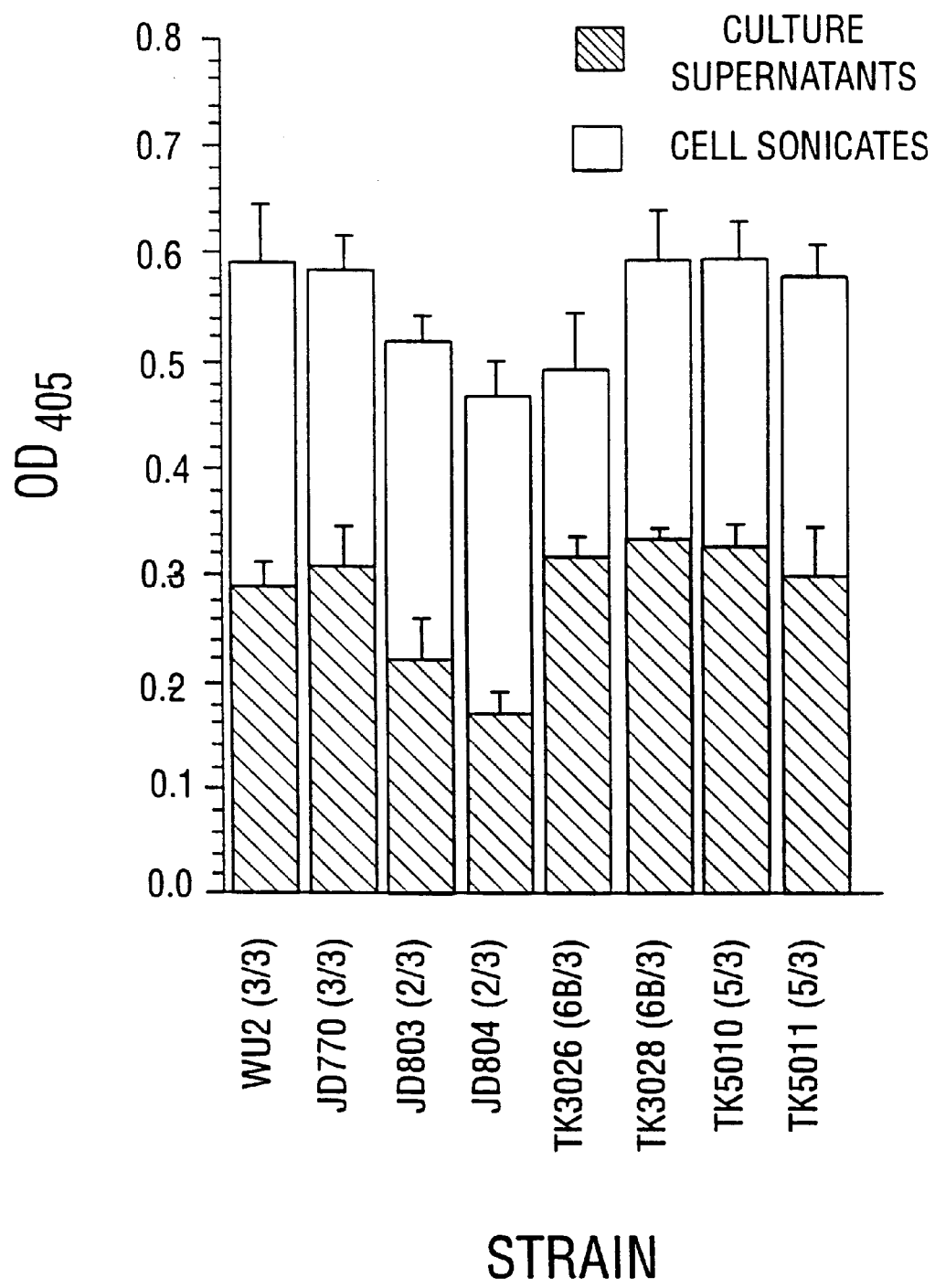
FIG. 13. Total capsule production. Triplicate cultures of each strain were grown to an $OD_{600}$ of ~0.5. Duplicate wells of polyvinyl plates were coated with either supernatant fluids or cell sonicates. Total capsule contents of the type 3 parent and the derivatives were determined by using a monoclonal antibody to type 3 capsule. See Table 2, footnote d, for explanation of strain designations.

Morphologically, type 3 strains exhibit large mucoid capsules when grown on blood agar plates, whereas type 2, 5, and 6B strains have small mucoid capsules. The type 3 derivatives of the type 2, 5, and 6B strains had a similar appearance to the type 3 parent on blood agar plates. The increase in colony size compared with that of the recipient parents did not appear to be due to cell number since similar numbers of cells per colony were observed for all of the parent and derivative type 3 strains (data not shown). To examine capsule production, Percoll density gradients and ELISAs were performed. Percoll density gradient centrifugation has been shown previously to differentiate capsular serotypes and amounts by density (Briles et al., 1992). In this assay, all of the derivatives had densities similar to that of the parent type 3 strain and distinct from that of the recipient parent strains (FIG. 12). Thus, all of the derivatives produced cell-associated, surface-localized type 3 capsule in amounts similar to that of the type 3 parent. The total amounts of capsule material produced, i.e., both cell associated and released, were determined in ELISAs to be similar for both the type 3 parent and each of the derivatives (FIG. 18). ELISAs were also used to confirm that the amounts of surface-accessible capsule were similar in the type 3 parent and the derivatives.

4. Virulence of type 3 derivatives.

Figure 14A:
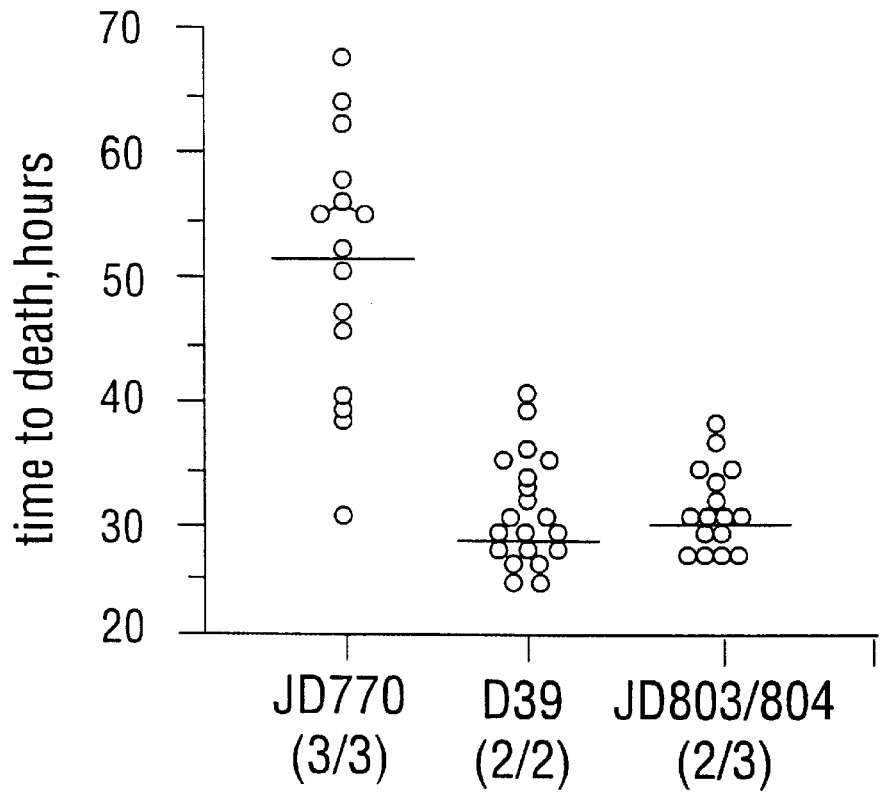
FIG. 14A. All studies were done in BALB/ByJ mice. See Table 7, footnote d, for explanation of strain designations. Virulence of type 2 derivatives. The parental strains JD770 (3/3) and D39 (2/2) and the derivatives JD803 (2/3) and JD804 (2/3) had similar $LD_{50}$s (50 to 75 CFU). For time-to-death studies, groups of mice were infected i.p. with doses approximately 5- to 20-fold above the $LD_{50}$. The observed times to death were not related to the dose received. Each circle represents an individual mouse. The median times to death for D39 (2/2) and for derivatives JD803 (2/3) and JD804 (2/3) were 31.5 and 33.0 h, respectively (not significantly different). All three values differed significantly (P<0.005) from that of the type 3 parent JD770 (52 h). The values for JD803 and JD804 did not differ from each other.
Figure 14B:
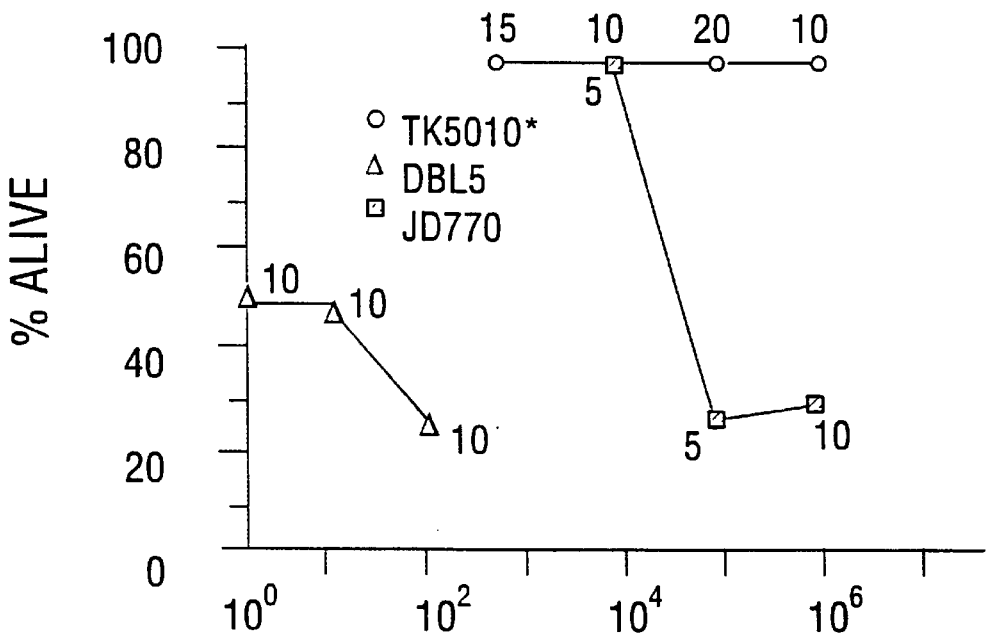
FIG. 14B. All studies were done in BALB/ByJ mice. See Table 7, footnote d, for explanation of strain designations. Virulence of the type 5 derivatives. Mice were infected i.v. with doses of $10^3$ to $10^6$ CFU (10-fold increments) of each type 3 derivative. Doses of $10^0$ to $10^2$ and $10^3$ to $10^6$ CFU were used fro the parental strains DBL5 (5/5) and JD770 (3/3), respectively. The total number of mice used per dose is listed beside each datum point. TK5010* represents the combined data for TK5010 (5/3), TK5011 (5/3), and TK5012 (5/3). The derivatives did not differ from each other but did differ significantly from the parental strains JD770 (P<0.0005) and DBL5 (P<0.0001).
Figure 14C:
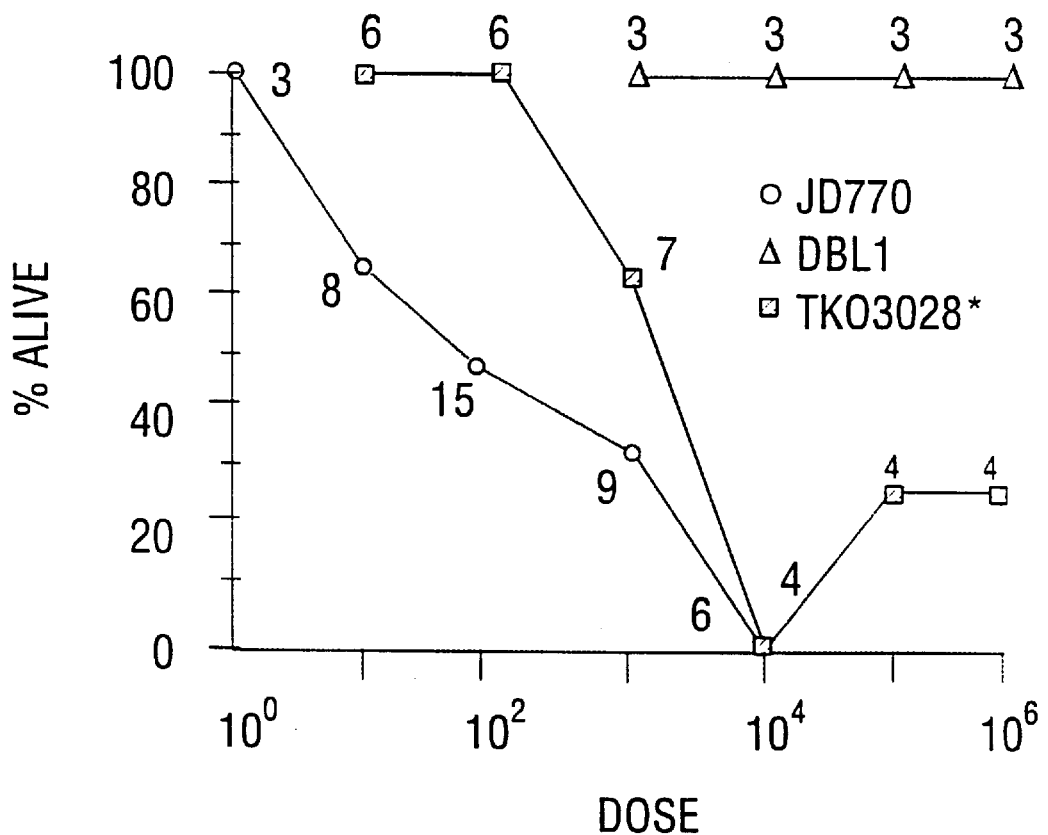
FIG. 14C. All studies were done in BALB/ByJ mice. See Table 7, footnote d, for explanation of strain designations. Virulence of type 6B derivatives. Mice were infected i.p. with doses of $10^1$ to $10^6$ CFU of the type 6B derivatives. Doses of $10^0$ to $10^3$ CFU and of $10^3$ to $10^6$ CFU were examined for the parent strains JD770 (3/3) and DBL1 (6B/6B), respectively. The total number of mice used per dose is listed beside each datum point. TK3028* represents the combined data for TK3026 (6B/3) and TK3028 (6B/3), which did not differ fro each other. However, these strains did differ significantly from the parental strains JD770 (3/3) (P<0.003) and DBL1 (6B/6B) (P<0.0005).

To assess the effect of alteration of capsule type on virulence, BALB/ByJ female mice were infected i.p. or i.v. with the type 3 derivatives and parent strains. Strain JD770, which contains the nondestructive erythromycin resistance marker in the type 3 capsule locus, did not differ from its parent type 3 strain WU2 in terms of median time to death (52 versus 49.5 h, i.p.) or $LD_{50}$ (75 versus 50 CFU, i.p.; $1 \times 10^5$ versus $2 \times 10^5$ CFU, i.v.). Thus JD770 was used in subsequent studies for comparisons with the type 3 derivatives. As expected, the recipient parent strains were significantly different from JD770 with respect to time to death or $LD_{50}$s (FIG. 14). Expression of the type 3 capsule had no apparent effect on the virulence of the type 2 recipient strain; i.e., the time required to cause death was not significantly different from that of the type 2 parent but was significantly different from that of the type 3 parent (FIG. 14A). However, alteration of capsular type had dramatic effects on the virulence of the type 5 and 6B strains. In contrast to the highly virulent type 5 parental strain ($LD_{50}$, ~10 CFU) and the virulent type 3 parental strain ($LD_{50}$, ~$10^5$), the type 3 derivatives were not virulent even at doses of $10^6$ CFU (FIG. 14B). Switching of the type 6B capsule to type 3 resulted in a reduction of the $LD_{50}$ from >1×$10^6$ to ~6×$10^3$ CFU, a value that was similar to but still greater than the 7.5×$10^2$ value observed for the type 3 parent strain (FIG. 14C).

These results may be indicative of the role other factors play in pneumococcal virulence. For example, the type 5 capsule may represent one that results in high virulence with few other factors required, whereas the type 3 capsule may require the presence of other factors to be highly virulent. The introduction of the type 3 capsule into the type 5 genetic background may thus result in the expression of a virulent capsule but, in the absence of other necessary factors, in an avirulent strain. The increase in virulence of the type 6B strain suggests that the type 3 capsule is probably more virulent than the type 6B. However, its failure to become as virulent as the type 3 parent is suggestive of a lack of other virulence factors in the 6B background. The type 2 recipient was only slightly more virulent than the type 3 donor and no significant change was noted in the virulence of its derivatives (FIG. 12). This result may suggest that the type 2 and type 3 capsules are of equal virulence and that the "accessory factors" necessary for full virulence are present in both strains.

Whether the decrease in virulence of type 5 derivatives is related to the alteration of cell chain length is not known. Clearly, the parent type 3 strain is highly virulent with a similar chain length. The alteration in chain length may reflect a general change in the surface structure of the type 5 strains possibly resulting from the change in capsule expression. Because the strains constructed were transformed with chromosomal DNA the inventors cannot rule out the possibility that determinants closely linked to the capsule locus are affecting the outcome of these studies. However, because several backcrosses were performed, and because independent isolates exhibited identical characteristics, it is unlikely that unlinked determinants are responsible for the results.

EXAMPLE 19

Increased Virulence of *S. pneumoniae* type 6B by Inactivation of plpA.

In Example 18, the introduction of the type 3-specific cassette and linked genes into an avirulent type 6B strain resulted in expression of the type 3 capsule and an increase in virulence. To more clearly define the contribution of the capsular serotype to the virulence of *S. pneumoniae*, insertion-duplication mutagenesis was used to insert an erythromycin marker adjacent to the type 6B-specific capsule cassette in the 3' flanking region. Surprisingly, introduction of this insertion resulted in an increase in virulence of the type 6B strain (derivative $LD_{50}$ of $10^3$ versus parental $LD_{50}$ of >$10^6$, intraperitoneal). This enhancement of virulence could be attributed to the 1.2 kb SacI-HindIII fragment from the type 3 strain WU2 (pJD377) that was used to direct the erythromycin marker into the type 6B chromosome. Transformation of the wild type 6B strain with the SacI-HindIII fragment alone, followed by intraperitoneal infection of the transformation mixture into mice resulted in death in less than 24 hours. Identical results were obtained using multiple smaller fragments of the SacI-HindIII fragment. JD377 (Example 5) comprises the 3' end of cps3M and part of the gene plpA. The fragments used contained mutations that, like the original insertion, resulted in a defective plpA in the type 6B strain. These data suggest that avirulence of type 6B observed via the intraperitoneal route is due to expression of plpA, and that the increase in virulence of the type 6B strain expressing the type 3 capsule is the result of inactivation of the linked plpA and not expression of the type 3 capsule.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

ACIP, "Pneumococcal polysaccharide vaccine," *Morbid. Mortal. Weekly,* 30:410–419, 1981.

ACIP, "Pneumococcal polysaccharide vaccine," *Morbid. Mortal. Weekly,* 38:64–76, 1989.

Albright et al., "A 13-amino acid peptide in three yeast glycosyltransferases may be involved in dolichol recognition." *Proc. Natl. Acad. Sci. USA,* 86:7366, 1989.

Appelbaum, "Antimicrobial resistance in *Streptococcus pneumoniae*: an overview," *Clin. Infect. Dis.,* 15:77–83, 1992.

Atkinson and Long, "Homology of Rhizobium meliloti NodC to polysaccharide polymerizing enzymes." *Mol. Plant-Microbe Interact.* 5:439, 1992.

Austrian, "Pneumococcal infections," *In: Ger anier R. ed. Bacterial vaccines*, New York: Academic Press, Inc., 257–288, 1984.

Austrian et al., "Simultaneous production of two capsular polysaccharides by pneumococcus II. The genetic and biochemical bases of binary capsulation," *J. Exp. Med.,* 110:585–602, 1959.

Ausubel et al., *Current Protocols in Molecular Biology*, New York: Wiley, 1987.

Avery et al., Studies on the chemical nature of the substance inducing transformation of pneumococcal types. Induction of transformation by a desoxyribonucleic acid fraction isolated from pneumococcus type III," *J. Exp. Med.,* 79:137–158, 1944.

Bastin et al., "Repeat unit polysaccharides of bacteria: a model for polymerization resembling that of ribosomes and fatty acid synthetase, with a novel mechanism for determining chain length," *Mol. Microbiol.,* 7:725–734, 1993.

Bernheimer, A. W., "Synthesis of type III pneumococcal polysaccharide by suspensions of resting cells." *J. Exp. Med.,* 97:591, 1953.

Bernheimer et al., "Mutation in Pneumococcus type III affecting multiple cistrons concerned with the synthesis of capsular polysaccharide." *J. Bacteriol.,* 96:1099, 1968.

Bernheimer and Wermundsen, "Unstable binary capsulated transformants in pneumococcus," *J. Bacteriol.,* 98:1073–1079, 1969.

Bernheimer et al., "Qualitative differences in the behavior of pneumococcal deoxyribonucleic acids transforming to the same capsular type," *J. Bacteriol.,* 93:320–333, 1967.

Bernheimer and Wermundsen, "Homology in capsular transformation reactions in Pneumococcus," *Molec. Gen. Genet.,* 116:68–83, 1972.

Birnboim and Doly, "A rapid alkaline extraction procedure for screening recombinant plasmid DNA," *Nucleic Acids Res.,* 7:1513–1523, 1979.

Branconier and Odeberg, "Granulocyte phagocytosis and killing of virulent and avirulent serotypes of *S. pneumoniae.*" *J. Lab. Clin. Med.* 100:276–287 1982.

Briese and Hakenbeck, *"The target of penicillin. The murein sacculus of bacterial cell walls, architecture, and growth,"* Berlin, Walter de Gruyter, 1983.

Briles et al., "A strong association between capsular type and mouse virulence among human isolates of *Streptococcus pneumoniae,"* *Infect. Immun.,* 60:111–116, 1992.

Briles et al., "Genetic control of susceptibility to pneumococcal infection," *Curr. Top. Microbiol. Immunol.,* 124:103–120, 1986.

Briles et al., "Mouse IgG3 antibodies are highly protective against infection with *Streptococcus pneumoniae,"* *Nature,* 294:88–90, 1981a.

Briles et al., "Antiphosphocholine antibodies found in normal mouse serum are protective against intravenous infection with type 3 *Streptococcus pneumoniae,"* *J. Exp. Med.,* 153:694–705, 1981b.

Brosius and Holy, "Regulation of ribosomal RNA promoters with a synthetic lac operator." *Proc. Natl. Acad. Sci. USA* 81:6929, 1984.

Burke et al., "Pneumococcal bacteremia: review of 111 cases, 1957–1959, with special references to cases of undetermined focus," *Am. J. Dis. Child.,* 121:353–359, 1971.

Campbell, in Monoclonal Antibody Technology, Laboratory Techniques in Biochemistry and Molecular Biology Vol. 13, Burden and Von Knippenberg, Eds. pp. 75–83, Amsterdam, Elseview, 1984

Centers for Disease Control, "Bacterial meningitis and meningococcemia—United States, 1978," *Morbid. Mortal. Weekly Rep.,* 28:277–279, 1978.

Coffey et al., "Horizontal transfer of multiple penicillin-binding protein genes, and capsular biosynthetic genes, in natural populations of *Streptococcus pneumoniae,"* *Molec. Microbiol.,* 5:2255–2260, 1991.

Crain et al., "Pneumococcal surface protein A (PspA) is serologically variable and is expressed by all clinically important capsular serotypes of *Streptococcus pneumoniae,"* *Infect. Immun.,* 58:3293–3299, 1990.

Dawson, M. H., "The transformation of pneumococcal types. II. The interconvertibility of type-specific *S pneumococci."* *J. Exp. Med.,* 51:123, 1930.

Dawson and Sia, "In vitro transformation of pneumococcal types. I. A technique for inducting transformation of pneumococcal types in vitro," *J. Exp. Med.,* 54:681–699, 1931.

DeAngelis et al., "Isolation of a Streptococcus pyogenes gene locus that directs hyaluronan biosynthesis in acapsular mutants and in heterologous bacteria." *J. Biol. Chem.,* 268:14568, 1993a.

DeAngelis et al., "Molecular cloning, identification, and sequence of the hyaluronan synthase gene from group A *Streptococcus pyogenes."* *J. Biol. Chem.,* 268:19181, 1993b.

Debellé et al., "The Rhizobium, Bradyrhizobium, and Azorhizobium NodC proteins are homologous to yeast chitin synthases." *Mol. Plant-Microbe Interact.,* 5:443, 1992.

Deretic, et al., "Pseudomonas aeruginosa infection in cystic fibrosis: nucleotide sequence of the algD gene." *Nucleic Acids Res.,* 15:4567, 1987.

Dillard and Yother, "Analysis of *Streptococcus pneumoniae* sequences cloned into *Escherichia coli*: effect of promoter strength and transcription terminators," *J. Bacteriol.,* 173:5105–5109, 1991.

Dillard and Yother, "Genetic and molecular characterization of capsular polysaccharide biosynthesis in *Streptococcus pneumoniae* type 3." *Molec. Microbiol.,* 12:959, 1994.

Dougherty and van de Rijn, "Molecular characterization of hasA from an operon required for hyaluronic acid synthesis in group A streptococci." *J. Biol. Chem.,* 269:169, 1994.

Dougherty and van de Rijn, "Molecular characterization of hasB from an operon required for hyaluronic acid synthesis in Group A streptococci," *J. Biol. Chem.,* 268:7118–7124, 1993.

Effrussi-Taylor, "Genetic aspects of transformation of pneumococci," *Cold Spr. Harb. Symp. Quant. Biol.,* 16:445–456, 1951.

Fine, "Pneumococcal type-associated variability in alternate complement pathway activation," *Infect. Immun.,* 12:772–778, 1975.

Finland and Barnes, "Changes in occurrence of capsular serotypes of *Streptococcus pneumoniae* at Boston City Hospital during selected years between 1935 and 1974," *J. Clin. Microbiol.,* 5:154–166, 1977.

Frosch et al., "Molecular characterization and expression in *Escherichia coli* of the gene complex encoding the polysaccharide capsule of *Neisseria meningitidis* group B," *Proc. Natl. Acad. Sci. USA,* 86:1699–1673, 1989.

Garcia et al., "Cloning of a gene involved in the synthesis of the capsular polysaccharide of *Streptococcus pneumoniae* type 3," *Mol. Gen. Genet.,* 239:188–195, 1993.

Gefter et al., *Somatic Cell Genet.* 3:231–236 (1977)

Genetics Computer Group. Program Manual for the GCG Package, Version 7, 1991.

Giebink et al., "Opsonic requirements for phagocytosis of *S. pneumoniae* types VI, XVII, XXIII, and XXV." *Infect. Immun.* 18:291–297, 1977.

Goding, in Monoclonal Antibodies: Principles and Practice, 2d ed., Orlando, Fla., Academic Press, 1986, pp. 60–61, 65–66, 71–74, 1986.

Gordon et al., "Ligand-receptor interactions in the phagocytosis of virulent *Streptococcus pneumoniae* by polymorphonuclear leukocytes," *J. Tnfect. Dis.,* 154:619–626, 1986.

Gray and Dillon, "Clinical and epidemiologic studies of pneumococcal infection in children," *Pediatr. Infect. Dis.,* 5:201–207, 1986.

Harr et al., "Search algorithm for pattern match analysis of nucleic acid sequences." *Nuc. Acids Res.,* 11:2943, 1983.

Hostetter, "Serotypic variation among virulent pneumococci in deposition and degradation of covalently bound C3b: implications for phagocytosis and antibody production," *J. Infect. Dis.,* 153:682–693, 1986.

Jacobs et al., "Emergency of multiply resistant pneumococci," *N. Engl. J. Med.,* 299:735–740, 1978.

Janoff et al., "Pneumococcal disease during HIV infection: epidemiologic, clinical, and immunologic perspectives," *Ann. Intern. Med.,* 117:314–324, 1992.

John et al., "Transmembrane orientation and receptor-like structure of the Rhizobium meliloti common nodulation protein NodC." *EMBO J.,* 7:583, 1988.

Johnson et al., "Immunogold localization of the NodC and NodA proteins of Rhizobium meliloti." *J. Bacteriol.,* 171:4583, 1989.

Johnston and Sell, "Septicemia in infants and children," *Pediatrics.,* 34:473–479, 1964.

Kado and Liu, "Rapid procedure for detection and isolation of large and small plasmids," *J. Bacteriol.,* 145:1365–1373, 1981.

Katsube et al., "Expression in Escherichia coli of UDP-glucose pyrophosphorylase cDNA from potato tuber and functional assessment of the five lysyl residues located at the substrate binding site." *Biochemistry,* 30:8546, 1991.

Kazuta et al., "Identification of lysyl residues located at the substrate-binding site in UDP-glucose pyrophosphorylase from potato tuber: affinity labeling with uridine di- and triphosphopyridoxals," *Biochemistry,* 30:8541, 1991.

Kelleher et al., "Oligosaccharyl transferase activity is associated with a protein complex composed of ribophorins I and II and a 48 kd protein." *Cell,* 69:55, 1992.

Knecht et al., "Some biologic properties of pneumococcus type 37 and the chemistry of its capsular polysaccharide," *J. Exp. Med.,* 132:475–485, 1970.

Koch and Dennison, "Office visits to pediatricians," *National Ambulatory Medical Care Service,* National Center for Statistics, 1974.

Kohler and Milstein, *Nature* 256:495–497, 1975.

Kohler and Milstein, *Eur. J. Immunol.* 6:511–519, 1976.

Kroll et al., "Common organization of chromosomal loci for production of different capsular polysaccharides in *Haemophilus influenzae,*" *J. Bacteriol.,* 171:3343–3347, 1989.

Kyte and Doolittle, "A simple method for displaying the hydropathic character of a protein." *J. Mol. Biol.,* 157(1):105–132, 1982.

Landesman et al., "Infections in children with sickle cell anemia. Special reference to pneumococcal and salmonella infections," *Am. J. Pediatr. Hematol Oncol.,* 4:407–18, 1982.

Langvad-Nielson, "Change of capsule in the pneumococcus," *Acta Path et Microbiol. Scand.,* 21:362–369, 1944.

Lerouge et al., "Symbiotic host specificity of Rhizobium meliloti is determined by a sulphated and acylated glucosamine oligosaccharide signal." *Nature,* 344:781, 1990.

MacLeod, "Pneumococci," In: *Bacterial and mycotic infections of man,* 391–411, Dubose and Hirsch eds., Lippincott, Philadelphia, Pa, 1965.

Morrison et al., "Isolation of transformation-deficient *Streptococcus pneumoniae* mutants defective in control of competence, using insertion-duplication mutagenesis with the erythromycin resistance determinant of pAMb1," *J. Bacteriol.,* 159:870–876, 1984.

Muckerman et al., "Transformation of restriction endonuclease phenotype in *Streptococcus pneumoniae,*" *J. Bacteriol.,* 152:183–190, 1982.

Mulligan and McClure, "Analysis of the occurrence of promoter-sites in DNA." *Nuc. Acids Res.,* 14:109, 1986.

Overturf et al., "Bacterial meningitis and septicemia in sickle cell disease," *Am. J. Dis. Child.,* 131:784–7, 1977.

Pearce et al., "Genetic identification of exported proteins in *Streptococcus pneumoniae.*" *Molec. Microbiol.,* 9:1037, 1993.

Pearce et al., "Peptide permeases modulate transformation in *Streptococcus pneumoniae.*" *Molec. Microbiol.,* 12:881, 1994.

Powars, "Natural history of sickle cell disease—the first ten years," *Semin. Hematol.,* 12:267–85, 1975.

Powars et al., "Pneumococcal septicemia in children with sickle cell anemia. Changing trend of survival," *JAMA,* 245:1839–42, 1981.

Radloff et al., "A dye-buoyant-density method for the detection and isolation of closed circular duplex DNA: the closed circular DNA in HeLa cells," *Proc. Natl. Acad. Sci. USA,* 57:1514–1521, 1967.

Ravin, "Reciprocal capsular transformation of pneumococci," *J. Bacteriol.,* 77:296–309, 1959.

Ravin, "Linked mutations borne by deoxyribonucleic acid controlling the synthesis of capsular polysaccharide in pneumococcus," *Genetics* 45:1387–1403, 1960.

Reed and Muench, "A simple method of estimating fifty percent endpoints," *Am. J. Hyg.* 27:493–497, 1938.

Reeves and Goebel, "Chemoimmunological studies on the soluble specific substance of pneumococcus. V. The structure of the type III polysaccharide," *J. Biol. Chem.,* 139:511–519, 1941.

Ridley, et al., "Mechanism of action of uridine diphosphoglucose dehydrogenase: evidence for a second reversible dehydrogenation step involving an essential thiol group." *J. Biol. Chem.* 250:8761, 1975.

Roberts et al., "Common organization of gene clusters for production of different capsular polysaccharides (K antigens) in *Escherichia coli,*" *J. Bacteriol.,* 170:1305–1310, 1988.

Rubens, et al., "Identification of cpsD, a gene essential for type III capsule expression in group B streptococci." *Molec. Microbiol.,* 8:843, 1993.

Sambrook et al., "Molecular cloning: A laboratory manual," *Cold Springs Harbor Laboratory,* Cold Springs Harbor, N.Y., 1989.

Saunders and Guild, "Properties and transforming activities of two plasmids in *Streptococcus pneumoniae,*" *Mol. Gen. Genet.,* 128:283–290, 1980.

Schiller et al., "UDP-glucose dehydrogenase from *Escherichia coli.* Purification and subunit structure," *Biochim. Biophys. Acta,* 453:418–425, 1976.

Schutzbach, et al., "The purification and characterization of recombinant yeast dolichol-phosphate-mannose synthase. Site-directed mutagenesis of the putative dolichol recognition sequence." *J. Biol. Chem.,* 268:24190, 1993.

Shoemaker and Guild, "Destruction of low efficiency markers is a slow process occurring at a heteroduplex stage of transformation," *Molec. Gen. Genet.,* 128:283–290, 1974.

Smith, et al., "Uridine pyrophosphoglucose dehydrogenase in capsulated and non-capsulated strains of pneumococcus type I." *J. Gen. Microbiol.,* 22:265, 1960.

Smith, et al., "The formation of uridine pyrophosphoglucuronic acid from uridine pyrophosphoglucose by extracts of a noncapsulated strain of pneumococcus." *Biochim. Biophys. Acta,* 28:211, 1958.

Smith et al., "The synthesis of type III pneumococcal capsular polysaccharide from uridine nucleotides by a cell-free extract of *Diplococcus pneumoniae* type III," *J. Biol. Chem.,* 235:1876–1880, 1960.

Smith, et al., "Biosynthesis of pneumococcal capsular polysaccharides: I. Properties of the system synthesizing type III capsular polysaccharide," *J. Biol. Chem.,* 236:2179, 1961.

Sorensen, et al., "Covalent linkage between the capsular polysaccharide and the cell wall peptidoglycan of *Streptococcus pneumoniae* revealed by immunochemical methods," *Microbial. Pathog.*, 8:325, 1990.

Stephens et al., "Classical and alternative complement pathway activation by pneumococci," *Infect. Tmmun.*, 17:296, 1977.

Taylor, "Additive effects of certain transforming agents from some variants of pneumococcus," *J. Exp. Med.*, 89:399–424, 1949.

Tilghman et al., "Cloning specific segments of the mammalian genome: bacteriophage lambda containing mouse globin and surrounding gene sequences," *Proc. Natl. Acad. Sci. USA*, 74:4406–4410, 1977.

van Dam et al., "Immunogenicity and immunochemistry of *Streptococcus pneumoniae* capsular polysaccharides," *Antonie van Leeuwenhoek*, 58:1–47, 1990.

Versalovic et al., "Penicillin-resistant *Streptococcus pneumoniae* strains recovered in Houston: identification and molecular characterization of multiple clones," *J. Infect. Dis.*, 167:850–856, 1993.

Walter et al., "Extension of the separation of types among pneumococci: description of 17 types in addition to types 1 to 32 (Cooper)," *J. Immunol.*, 41:279, 1941.

Wierenga, et al., "Prediction of the occurrence of the ADP-binding bab-fold in proteins, using an amino acid sequence fingerprint," *J. Mol. Biol.*, 187:101, 1986.

Winkelstein et al., "Activation of C3 via the alternative complement pathway results in fixation of C3b to the pneumococcal cell wall," *J. Immunol.*, 124:2502–2506, 1980.

Winkelstein et al., "The role of the capsular polysaccharide in the activation of the alternative pathway by the pneumococcus," *J. Immunol.*, 116:367–370, 1976.

Wood and Smith, "The inhibition of surface phagocytosis by the capsular 'slime layer' of pneumococcus type III," *J. Exp. Med.*, 90:85–96, 1949.

Yother and White, "Novel surface attachment mechanism of the *Streptococcus pneumoniae* protein PspA," *J. Bacteriol.*, 176:2976, 1994.

Yother et al., "Protection of mice from infections with *Streptococcus pneumoniae* by anti-phosphocholine antibody," *Infect. Immun.*, 36:184–188, 1982.

Yother et al., "Truncated forms of PspA that are secreted from *Streptococcus pneumoniae* and their use in functional studies and cloning of the pspA gene," *J. Bacteriol.*, 174:610–618, 1992.

Yother et al., "Transformation of encapsulated *Streptococcus pneumoniae*," *J. Bacteriol.*, 168:1463–1465, 1986.

Zar, "Biostatistical analysis," p. 718. Prentice Hall, Inc., Englewood Cliffs, N.J. 1984.

Zwahlen et al., "The molecular basis of pathogenicity in *Haemophilus influenzae*: comparative virulence of genetically-related capsular transformants and correlation with changes at the capsulation locus cap," *Microbial. Pathog.*, 7:225–235, 1989.

---

What is claimed is:

1. A nucleic acid segment less than 10 kb in length that comprises a non-type specific S. pneumoniae cps gene flanking region of sufficient length to allow for hybridization to a S. pneumoniae cps flanking region, wherein said nucleic acid segment is selected from the group consisting of SEQ ID NO: 1, SEQ ID NO: 2, SEQ ID NO: 3, SEQ ID NO: 4 and SEQ ID NO: 6.

2. The nucleic acid segment of claim 1, wherein the segment encodes a peptide selected from the group consisting of SEQ ID NO:7, SEQ ID NO: 8, SEQ ID NO: 9 and SEQ ID NO: 10.

3. The nucleic acid segment of claim 2, wherein the segment further comprises a non-type specific S. pneumoniae cps gene 5' flanking region having a sequence that comprises to at least a 60 nucleotide long contiguous stretch of SEQ ID NO: 4.

4. The nucleic acid segment of claim 1, wherein the segment comprises a non-type specific S. pneumoniae cps gene 3' flanking region.

5. The nucleic acid segment of claim 4, wherein the segment comprises a non-type specific S. pneumoniae cps gene 3' flanking region having a sequence that corresponds to at least a 15 nucleotide long contiguous stretch of SEQ ID NO:6.

6. The nucleic acid segment of claim 1, further comprising a type specific S. pneumoniae cps gene region of sufficient length to allow for hybridization to a S. pneumoniae cps gene region.

7. An isolated nucleic acid segment, wherein the segment comprises a non-type specific S. pneumoniae cps gene 5' flanking region and a non-type specific S. pneumoniae cps gene 3' flanking region, wherein the segment comprises a 5' flanking region comprising SEQ ID NO: 1, SEQ ID NO: 2 and SEQ ID NO: 3 that encodes for a peptide comprising SEQ ID NO:7, SEQ ID NO:8, SEQ ID NO:9 and SEQ ID NO:10 and a 3' flanking region sequence that comprises at least a 30 nucleotide long contiguous stretch of SEQ ID NO: 6.

8. An isolated nucleic acid cassette less than 20 kb in length that comprises a non-type specific S. pneumoniae cps gene 5' flanking region sequence comprising SEQ ID NO: 1, SEQ ID NO: 2 and SEQ ID NO: 3 and non-type specific S. pneumoniae cps gene 3' flanking region sequence corresponding to at least a 30 nucleotide long contiguous stretch of SEQ ID NO: 6, the flanking region sequences being of sufficient length to allow for hybridization to a S. pneumoniae cps gene flanking region.

* * * * *